US010299958B2

(12) United States Patent
Badawi et al.

(10) Patent No.: US 10,299,958 B2
(45) Date of Patent: May 28, 2019

(54) OCULAR DELIVERY SYSTEMS AND METHODS

(71) Applicant: Sight Sciences, Inc., Menlo Park, CA (US)

(72) Inventors: David Y. Badawi, Glenview, IL (US); Daniel O'Keeffe, San Francisco, CA (US); Paul Badawi, San Francisco, CA (US)

(73) Assignee: Sight Sciences, Inc., Menlo Park, CA (US)

( * ) Notice: Subject to any disclaimer, the term of this patent is extended or adjusted under 35 U.S.C. 154(b) by 725 days.

(21) Appl. No.: 14/675,580

(22) Filed: Mar. 31, 2015

(65) Prior Publication Data

US 2016/0287438 A1 Oct. 6, 2016

(51) Int. Cl.
*A61F 9/00* (2006.01)
*A61M 25/01* (2006.01)
(Continued)

(52) U.S. Cl.
CPC .......... *A61F 9/0017* (2013.01); *A61K 31/728* (2013.01); *A61K 33/14* (2013.01);
(Continued)

(58) Field of Classification Search
CPC ...... A61F 9/0008; A61F 9/0017; A61F 9/007; A61F 9/00736; A61K 31/728; A61K 33/14; A61M 25/0662
(Continued)

(56) References Cited

U.S. PATENT DOCUMENTS 3,159,161 A 12/1964 Ness
4,068,664 A 1/1978 Sharp et al.
(Continued)

FOREIGN PATENT DOCUMENTS

JP 03-168154 A 7/1991
JP 2002-541976 A 12/2002
(Continued)

OTHER PUBLICATIONS

Boyle, E.L. (Feb. 1, 2006). "New Glaucoma Devices Take Different Approaches to IOP Lowering," Ocular Surgery News U.S. Edition, located at <http://www.osnsupersite.com/view.aspx?rid=12436>, last visited on Apr. 23, 2012, 4 pages, revisited on Apr. 19, 2016, 5 pages, total 9 pages.
(Continued)

*Primary Examiner* — Phillip A Gray
(74) *Attorney, Agent, or Firm* — Cooley LLP

(57) ABSTRACT

Described here are systems and methods for accessing Schlemm's canal and for delivering an ocular device, tool, or fluid composition therein. The ocular devices may maintain the patency of Schlemm's canal without substantially interfering with transmural fluid flow across the canal. The fluid composition may be a viscoelastic fluid that is delivered into the canal to facilitate drainage of aqueous humor by disrupting the canal and surrounding trabeculocanalicular tissues. Some systems described here may be configured to cut or tear the trabecular meshwork with the body of an elongate member located within Schlemm's canal. Other tools for disrupting these tissues and minimally invasive methods for treating medical conditions associated with elevated intraocular pressure, including glaucoma, are also described.

26 Claims, 40 Drawing Sheets

US 10,299,958 B2

Page 2

(51) Int. Cl.
  *A61M 25/06* (2006.01)
  *A61K 33/14* (2006.01)
  *A61K 31/728* (2006.01)
  *A61K 9/00* (2006.01)
  *A61F 9/007* (2006.01)

(52) U.S. Cl.
  CPC ..... *A61M 25/0662* (2013.01); *A61F 9/00781* (2013.01); *A61K 9/0051* (2013.01); *A61M 2025/0175* (2013.01); *A61M 2025/0681* (2013.01); *A61M 2210/0612* (2013.01)

(58) Field of Classification Search
  USPC ........................................................ 604/521
  See application file for complete search history.

(56) References Cited

U.S. PATENT DOCUMENTS

| | | | |
|---|---|---|---|
| 4,457,757 A | 7/1984 | Molteno | |
| 4,501,274 A | 2/1985 | Skjaerpe | |
| 4,553,545 A | 11/1985 | Maass et al. | |
| 4,719,825 A | 1/1988 | LaHaye et al. | |
| 4,936,825 A | 6/1990 | Ungerleider | |
| 4,957,505 A | 9/1990 | McDonald | |
| 5,092,837 A | 3/1992 | Ritch et al. | |
| 5,180,362 A | 1/1993 | Worst | |
| 5,284,476 A | 2/1994 | Koch | |
| 5,358,473 A | 10/1994 | Mitchell | |
| 5,360,399 A | 11/1994 | Stegmann | |
| 5,368,572 A | 11/1994 | Shirota | |
| 5,486,165 A | 1/1996 | Stegmann | |
| 5,540,657 A | 7/1996 | Kurjan et al. | |
| 5,558,634 A | 9/1996 | Mitchell | |
| 5,569,197 A | 10/1996 | Helmus et al. | |
| 5,626,558 A | 5/1997 | Suson | |
| 5,639,278 A | 6/1997 | Dereume et al. | |
| 5,792,099 A | 8/1998 | DeCamp et al. | |
| 5,792,103 A | 8/1998 | Schwartz et al. | |
| 5,868,697 A | 2/1999 | Richter et al. | |
| 6,036,678 A | 3/2000 | Giungo | |
| 6,050,970 A | 4/2000 | Baerveldt | |
| 6,050,999 A | 4/2000 | Paraschac et al. | |
| 6,299,603 B1 | 10/2001 | Hecker et al. | |
| 6,309,375 B1 | 10/2001 | Glines et al. | |
| 6,375,642 B1 | 4/2002 | Grieshaber et al. | |
| 6,491,670 B1 | 12/2002 | Toth et al. | |
| 6,494,857 B1 | 12/2002 | Neuhann | |
| 6,508,779 B1 | 1/2003 | Suson | |
| 6,524,275 B1 | 2/2003 | Lynch et al. | |
| 6,533,768 B1 | 3/2003 | Hill | |
| 6,616,996 B1 | 9/2003 | Keith et al. | |
| 6,626,858 B2 | 9/2003 | Lynch et al. | |
| 6,666,841 B2 | 12/2003 | Gharib et al. | |
| 6,726,676 B2 | 4/2004 | Stegmann et al. | |
| 6,730,056 B1 | 5/2004 | Ghaem et al. | |
| 6,736,791 B1 | 5/2004 | Tu et al. | |
| 6,780,164 B2 | 8/2004 | Bergheim et al. | |
| 6,783,544 B2 | 8/2004 | Lynch et al. | |
| 6,840,952 B2 | 1/2005 | Saker et al. | |
| 6,843,792 B2 | 1/2005 | Nishtala et al. | |
| 6,893,415 B2 | 5/2005 | Madsen et al. | |
| 6,955,656 B2 | 10/2005 | Bergheim et al. | |
| 6,962,573 B1 | 11/2005 | Wilcox | |
| 7,094,225 B2 | 8/2006 | Tu et al. | |
| 7,135,009 B2 | 11/2006 | Tu et al. | |
| 7,186,232 B1 | 3/2007 | Smedley et al. | |
| 7,207,980 B2 | 4/2007 | Christian et al. | |
| 7,273,475 B2 | 9/2007 | Tu et al. | |
| 7,297,130 B2 | 11/2007 | Bergheim et al. | |
| 7,331,984 B2 | 2/2008 | Tu et al. | |
| 7,488,303 B1 | 2/2009 | Haffner et al. | |
| 7,713,228 B2 | 5/2010 | Robin | |
| 7,740,604 B2 | 6/2010 | Schieber et al. | |
| 7,806,847 B2 | 10/2010 | Wilcox | |
| 7,850,637 B2 | 12/2010 | Lynch et al. | |
| 7,867,205 B2 | 1/2011 | Bergheim et al. | |
| 7,909,789 B2 | 3/2011 | Badawi et al. | |
| 7,951,155 B2 | 5/2011 | Smedley et al. | |
| 7,967,772 B2 | 6/2011 | McKenzie et al. | |
| 8,034,105 B2 | 10/2011 | Stegmann et al. | |
| 8,075,511 B2 | 12/2011 | Tu et al. | |
| 8,109,896 B2 | 2/2012 | Nissan et al. | |
| 8,123,729 B2 | 2/2012 | Yamamoto et al. | |
| 8,133,208 B2 | 3/2012 | Hetherington | |
| 8,152,752 B2 | 4/2012 | Lynch et al. | |
| 8,172,899 B2 | 5/2012 | Silvestrini et al. | |
| 8,267,882 B2 | 9/2012 | Euteneuer et al. | |
| 8,273,050 B2 | 9/2012 | Bergheim et al. | |
| 8,282,592 B2 | 10/2012 | Schieber et al. | |
| 8,287,482 B2 | 10/2012 | Badawi et al. | |
| 8,333,742 B2 | 12/2012 | Bergheim et al. | |
| 8,337,509 B2 | 12/2012 | Schieber et al. | |
| 8,348,924 B2 | 1/2013 | Christian et al. | |
| 8,366,653 B2 | 2/2013 | Shareef et al. | |
| 8,372,026 B2 | 2/2013 | Schieber et al. | |
| 8,388,568 B2 | 3/2013 | Lynch et al. | |
| 8,403,920 B2 | 3/2013 | Lind et al. | |
| 8,414,518 B2 | 4/2013 | Schieber et al. | |
| 8,425,449 B2 | 4/2013 | Wardle et al. | |
| 8,425,450 B2 | 4/2013 | Wilcox | |
| 8,439,972 B2 | 5/2013 | Badawi et al. | |
| 8,444,589 B2 | 5/2013 | Silvestrini | |
| 8,491,549 B2 | 7/2013 | Conston et al. | |
| 8,512,321 B2 | 8/2013 | Baerveldt et al. | |
| 8,512,404 B2 | 8/2013 | Frion et al. | |
| 8,529,622 B2 | 9/2013 | Badawi et al. | |
| 8,540,659 B2 | 9/2013 | Berlin | |
| 8,540,681 B2 | 9/2013 | Hetherington | |
| 8,545,431 B2 | 10/2013 | Rickard | |
| 8,568,391 B2 | 10/2013 | Kearns et al. | |
| 8,617,094 B2 | 12/2013 | Smedley et al. | |
| 8,657,776 B2 | 2/2014 | Wardle et al. | |
| 8,663,150 B2 | 3/2014 | Wardle et al. | |
| 8,715,266 B2 | 5/2014 | Bos | |
| 8,734,377 B2 | 5/2014 | Schieber et al. | |
| 8,747,299 B2 | 6/2014 | Grieshaber | |
| 8,771,217 B2 | 7/2014 | Lynch et al. | |
| 8,801,648 B2 | 8/2014 | Bergheim et al. | |
| 8,808,222 B2 | 8/2014 | Schieber et al. | |
| 8,827,990 B2 | 9/2014 | Van Valen et al. | |
| 8,852,137 B2 | 10/2014 | Horvath et al. | |
| 8,876,898 B2 | 11/2014 | Badawi et al. | |
| 8,888,734 B2 | 11/2014 | Nissan et al. | |
| 8,894,603 B2 | 11/2014 | Badawi et al. | |
| 8,926,546 B2 | 1/2015 | Wilcox | |
| 8,961,447 B2 | 2/2015 | Schieber et al. | |
| 9,039,650 B2 | 5/2015 | Schieber et al. | |
| 9,044,301 B1 | 6/2015 | Pinchuk et al. | |
| 9,050,169 B2 | 6/2015 | Schieber et al. | |
| 9,066,750 B2 | 6/2015 | Wardle et al. | |
| 9,066,783 B2 | 6/2015 | Euteneuer et al. | |
| 9,095,412 B2 | 8/2015 | Badawi et al. | |
| 9,107,729 B2 | 8/2015 | Sorensen et al. | |
| 9,125,723 B2 | 9/2015 | Horvath et al. | |
| 9,155,655 B2 | 10/2015 | Schieber et al. | |
| 9,192,516 B2 | 11/2015 | Horvath et al. | |
| 9,211,213 B2 | 12/2015 | Wardle et al. | |
| 9,216,109 B2 | 12/2015 | Badawi et al. | |
| 9,220,632 B2 | 12/2015 | Smedley et al. | |
| 9,226,850 B2 | 1/2016 | Baerveldt et al. | |
| 9,226,852 B2 | 1/2016 | Schieber et al. | |
| 9,301,875 B2 | 4/2016 | Tu et al. | |
| 9,326,891 B2 | 5/2016 | Horvath et al. | |
| 9,339,514 B2 | 5/2016 | Bos et al. | |
| 9,351,874 B2 | 5/2016 | Schieber et al. | |
| 9,358,155 B2 | 6/2016 | Sorensen et al. | |
| 9,358,156 B2 | 6/2016 | Wardle et al. | |
| 9,370,443 B2 | 6/2016 | Badawi et al. | |
| 9,381,111 B2 | 7/2016 | Hickingbotham et al. | |
| 9,402,767 B2 | 8/2016 | Schieber et al. | |
| 9,486,361 B2 | 11/2016 | Badawi et al. | |
| 9,492,319 B2 | 11/2016 | Grieshaber et al. | |
| 9,492,320 B2 | 11/2016 | Lynch et al. | |
| 9,510,973 B2 | 12/2016 | Wardle | |

(56) References Cited

U.S. PATENT DOCUMENTS

| | | |
|---|---|---|
| 9,855,167 B2 | 1/2018 | Badawi et al. |
| 9,895,258 B2 | 2/2018 | Badawi et al. |
| 2001/0014788 A1 | 8/2001 | Morris |
| 2002/0013546 A1 | 1/2002 | Grieshaber et al. |
| 2002/0013572 A1 | 1/2002 | Berlin |
| 2002/0055753 A1 | 5/2002 | Silvestrini |
| 2002/0072673 A1 | 6/2002 | Yamamoto et al. |
| 2002/0133168 A1 | 9/2002 | Smedley et al. |
| 2002/0143284 A1 | 10/2002 | Tu et al. |
| 2003/0060447 A1 | 3/2003 | Karakelle et al. |
| 2003/0060873 A1 | 3/2003 | Gertner et al. |
| 2003/0120200 A1 | 6/2003 | Bergheim et al. |
| 2003/0181848 A1 | 9/2003 | Bergheim et al. |
| 2003/0229303 A1 | 12/2003 | Haffner et al. |
| 2003/0236483 A1 | 12/2003 | Ren |
| 2003/0236484 A1 | 12/2003 | Lynch et al. |
| 2004/0044310 A1 | 3/2004 | Suzuki |
| 2004/0193095 A1 | 9/2004 | Shadduck |
| 2004/0193262 A1 | 9/2004 | Shadduck |
| 2004/0210181 A1 | 10/2004 | Vass et al. |
| 2004/0254519 A1 | 12/2004 | Tu et al. |
| 2004/0254520 A1 | 12/2004 | Porteous et al. |
| 2004/0254521 A1 | 12/2004 | Simon |
| 2004/0260228 A1 | 12/2004 | Lynch et al. |
| 2005/0055082 A1 | 3/2005 | Ben Muvhar et al. |
| 2005/0101967 A1 | 5/2005 | Weber et al. |
| 2005/0171507 A1 | 8/2005 | Christian |
| 2005/0192527 A1 | 9/2005 | Gharib et al. |
| 2005/0209549 A1 | 9/2005 | Bergheim et al. |
| 2005/0250788 A1 | 11/2005 | Tu et al. |
| 2005/0266047 A1 | 12/2005 | Tu et al. |
| 2005/0267555 A1 | 12/2005 | Marnfeldt et al. |
| 2005/0277864 A1 | 12/2005 | Haffner et al. |
| 2005/0288619 A1 | 12/2005 | Gharib et al. |
| 2006/0032507 A1 | 2/2006 | Tu |
| 2006/0036207 A1 | 2/2006 | Koonmen et al. |
| 2006/0069340 A1 | 3/2006 | Simon |
| 2006/0074375 A1 | 4/2006 | Bergheim et al. |
| 2006/0084907 A1 | 4/2006 | Bergheim et al. |
| 2006/0149194 A1 | 7/2006 | Conston |
| 2006/0155300 A1 | 7/2006 | Stamper et al. |
| 2006/0173077 A1 | 8/2006 | Cagle |
| 2006/0173397 A1 | 8/2006 | Tu et al. |
| 2006/0173446 A1 | 8/2006 | Dacquay et al. |
| 2006/0195055 A1 | 8/2006 | Bergheim et al. |
| 2006/0195056 A1 | 8/2006 | Bergheim et al. |
| 2006/0195187 A1 | 8/2006 | Stegmann et al. |
| 2006/0200113 A1 | 9/2006 | Haffner et al. |
| 2006/0217741 A1 | 9/2006 | Ghannoum |
| 2006/0241580 A1 | 10/2006 | Mittelstein et al. |
| 2007/0073275 A1 | 3/2007 | Conston et al. |
| 2007/0106236 A1 | 5/2007 | Coroneo |
| 2007/0191863 A1 | 8/2007 | De Juan, Jr. et al. |
| 2007/0260173 A1 | 11/2007 | Boukhny et al. |
| 2007/0276420 A1 | 11/2007 | Sorensen et al. |
| 2007/0298068 A1 | 12/2007 | Badawi et al. |
| 2008/0004596 A1 | 1/2008 | Yun et al. |
| 2008/0058704 A1 | 3/2008 | Hee et al. |
| 2008/0058760 A1 | 3/2008 | Agerup |
| 2008/0082078 A1 | 4/2008 | Berlin |
| 2008/0300574 A1 | 12/2008 | Belson et al. |
| 2009/0036819 A1 | 2/2009 | Tu et al. |
| 2009/0043321 A1 | 2/2009 | Conston et al. |
| 2009/0082862 A1 | 3/2009 | Schieber et al. |
| 2009/0132040 A1 | 5/2009 | Frion et al. |
| 2009/0227934 A1 | 9/2009 | Euteneuer et al. |
| 2009/0247955 A1 | 10/2009 | Yamamoto et al. |
| 2009/0287143 A1 | 11/2009 | Line |
| 2009/0287233 A1 | 11/2009 | Huculak |
| 2010/0019177 A1 | 1/2010 | Luckevich |
| 2010/0087774 A1 | 4/2010 | Haffner et al. |
| 2010/0121248 A1 | 5/2010 | Yu et al. |
| 2010/0173866 A1 | 7/2010 | Hee et al. |
| 2010/0179652 A1 | 7/2010 | Yamamoto et al. |
| 2010/0191329 A1 | 7/2010 | Badawi et al. |
| 2010/0222802 A1 | 9/2010 | Gillespie |
| 2010/0241046 A1 | 9/2010 | Pinchuk et al. |
| 2010/0262174 A1 | 10/2010 | Sretavan et al. |
| 2011/0009874 A1 | 1/2011 | Wardle et al. |
| 2011/0009958 A1 | 1/2011 | Wardle et al. |
| 2011/0098809 A1 | 4/2011 | Wardle et al. |
| 2011/0130831 A1 | 6/2011 | Badawi et al. |
| 2011/0196487 A1 | 8/2011 | Badawi et al. |
| 2011/0224597 A1 | 9/2011 | Stegmann et al. |
| 2011/0238009 A1 | 9/2011 | Meron et al. |
| 2011/0238075 A1 | 9/2011 | Clauson et al. |
| 2011/0306915 A1 | 12/2011 | De Juan, Jr. et al. |
| 2012/0010702 A1 | 1/2012 | Stegmann et al. |
| 2012/0059461 A1 | 3/2012 | Badawi et al. |
| 2012/0123315 A1 | 5/2012 | Horvath et al. |
| 2012/0123434 A1 | 5/2012 | Grabner et al. |
| 2012/0136306 A1 | 5/2012 | Bartha |
| 2012/0165720 A1 | 6/2012 | Horvath et al. |
| 2012/0191064 A1 | 7/2012 | Conston et al. |
| 2012/0197175 A1 | 8/2012 | Horvath et al. |
| 2012/0197176 A1 | 8/2012 | Badawi et al. |
| 2012/0203160 A1 | 8/2012 | Kahook et al. |
| 2012/0220917 A1 | 8/2012 | Silvestrini et al. |
| 2012/0310072 A1 | 12/2012 | Grieshaber |
| 2012/0310137 A1 | 12/2012 | Silvestrini |
| 2013/0041346 A1 | 2/2013 | Alon |
| 2013/0158462 A1 | 6/2013 | Wardle et al. |
| 2013/0245600 A1 | 9/2013 | Yamamoto et al. |
| 2013/0253402 A1* | 9/2013 | Badawi .............. A61F 9/0017 604/8 |
| 2013/0253403 A1 | 9/2013 | Badawi et al. |
| 2013/0253437 A1 | 9/2013 | Badawi et al. |
| 2013/0253438 A1 | 9/2013 | Badawi et al. |
| 2013/0274655 A1 | 10/2013 | Jennings et al. |
| 2013/0345808 A1 | 12/2013 | Badawi et al. |
| 2014/0066833 A1 | 3/2014 | Yaron et al. |
| 2014/0081194 A1 | 3/2014 | Burns et al. |
| 2014/0121584 A1 | 5/2014 | Wardle et al. |
| 2014/0128847 A1 | 5/2014 | Lopez |
| 2014/0135916 A1 | 5/2014 | Clauson et al. |
| 2014/0163448 A1 | 6/2014 | Lind et al. |
| 2014/0171852 A1 | 6/2014 | Khor |
| 2014/0194916 A1 | 7/2014 | Ichikawa |
| 2014/0213958 A1 | 7/2014 | Clauson et al. |
| 2014/0236066 A1 | 8/2014 | Horvath et al. |
| 2014/0276332 A1 | 9/2014 | Crimaldi et al. |
| 2014/0288485 A1 | 9/2014 | Berlin |
| 2014/0309599 A1 | 10/2014 | Schaller |
| 2014/0364791 A1 | 12/2014 | Stegmann et al. |
| 2015/0005623 A1 | 1/2015 | Grover et al. |
| 2015/0011926 A1 | 1/2015 | Reitsamer et al. |
| 2015/0051699 A1 | 2/2015 | Badawi et al. |
| 2015/0065940 A1 | 3/2015 | Rangel-Friedman et al. |
| 2015/0073328 A1 | 3/2015 | Badawi et al. |
| 2015/0080783 A1 | 3/2015 | Berlin |
| 2015/0112372 A1 | 4/2015 | Perez Grossmann |
| 2015/0119787 A1 | 4/2015 | Wardle et al. |
| 2015/0125328 A1 | 5/2015 | Bourne et al. |
| 2015/0133946 A1 | 5/2015 | Horvath et al. |
| 2015/0148615 A1 | 5/2015 | Brennan et al. |
| 2015/0216729 A1 | 8/2015 | Doci |
| 2015/0223981 A1 | 8/2015 | Smedley et al. |
| 2015/0223983 A1 | 8/2015 | Schieber et al. |
| 2015/0250649 A1 | 9/2015 | Euteneuer et al. |
| 2015/0257932 A1 | 9/2015 | Pinchuk et al. |
| 2015/0282982 A1 | 10/2015 | Schieber et al. |
| 2015/0313758 A1 | 11/2015 | Wilcox |
| 2015/0320596 A1 | 11/2015 | Gifford, III et al. |
| 2015/0335481 A1 | 11/2015 | Badawi et al. |
| 2015/0374545 A1 | 12/2015 | Horvath et al. |
| 2016/0022486 A1 | 1/2016 | Clauson et al. |
| 2016/0051408 A1 | 2/2016 | Baerveldt et al. |
| 2016/0095985 A1 | 4/2016 | Novak |
| 2016/0100980 A1 | 4/2016 | Badawi et al. |
| 2016/0106589 A1 | 4/2016 | Mittelstein et al. |
| 2016/0135994 A1 | 5/2016 | Romoda et al. |
| 2016/0143778 A1 | 5/2016 | Aljuri et al. |
| 2016/0151204 A1 | 6/2016 | Haffner et al. |
| 2016/0220417 A1 | 8/2016 | Schieber et al. |

(56) References Cited

U.S. PATENT DOCUMENTS

| | | | |
|---|---|---|---|
| 2016/0220418 A1 | 8/2016 | Sorensen et al. |
| 2016/0256317 A1 | 9/2016 | Horvath et al. |
| 2016/0256323 A1 | 9/2016 | Horvath et al. |
| 2016/0287438 A1 | 10/2016 | Badawi et al. |
| 2016/0287440 A1 | 10/2016 | Badawi et al. |
| 2016/0302965 A1 | 10/2016 | Erickson et al. |
| 2016/0331588 A1 | 11/2016 | Ambati et al. |
| 2016/0346006 A1 | 12/2016 | Hickengbotham et al. |
| 2016/0354248 A1 | 12/2016 | Kahook |
| 2017/0143541 A1 | 5/2017 | Badawi et al. |
| 2017/0202707 A1 | 7/2017 | Badawi et al. |
| 2017/0258507 A1 | 9/2017 | Hetherington |
| 2017/0348152 A1 | 12/2017 | Badawi et al. |
| 2018/0271699 A1 | 9/2018 | Badawi et al. |

FOREIGN PATENT DOCUMENTS

| | | |
|---|---|---|
| JP | 2003-180730 A | 7/2003 |
| JP | 2005-510317 A | 4/2005 |
| JP | 2005-538809 A | 12/2005 |
| JP | 2007-527251 A | 9/2007 |
| WO | WO-00/64393 A1 | 11/2000 |
| WO | WO-03/045582 A1 | 6/2003 |
| WO | WO-2004/026361 A1 | 4/2004 |
| WO | WO-2004/069664 A2 | 8/2004 |
| WO | WO-2004/069664 A3 | 8/2004 |
| WO | WO-2005/105197 A2 | 11/2005 |
| WO | WO-2005/105197 A3 | 11/2005 |
| WO | WO-2005/107664 A2 | 11/2005 |
| WO | WO-2005/107664 A3 | 11/2005 |
| WO | WO-2005/117752 A1 | 12/2005 |
| WO | WO-2006/066103 A2 | 6/2006 |
| WO | WO-2006/066103 A3 | 6/2006 |
| WO | WO-2008/002377 A1 | 1/2008 |
| WO | WO-2009/042596 A2 | 4/2009 |
| WO | WO-2009/042596 A3 | 4/2009 |
| WO | WO-2011/097408 A1 | 8/2011 |
| WO | WO-2011/106781 A1 | 9/2011 |
| WO | WO-2013/141898 A1 | 9/2013 |
| WO | WO-2016/042162 A1 | 3/2016 |
| WO | WO-2016/159999 A1 | 10/2016 |

OTHER PUBLICATIONS

European Search Report dated Apr. 22, 2015, for European Patent Application No. 11740372.5, filed Feb. 3, 2011, six pages.
Final Office Action dated Nov. 1, 2010, for U.S. Appl. No. 11/475,523, filed Jun. 26, 2006, 12 pages.
Final Office Action dated Jul. 19, 2012, for U.S. Appl. No. 13/245,811, filed Sep. 26, 2011, 6 pages.
Final Office Action dated Feb. 1, 2013, for U.S. Appl. No. 13/020,706, filed Feb. 3, 2011, 6 pages.
Final Office Action dated Sep. 15, 2014, for U.S. Appl. No. 13/025,112, filed Feb. 10, 2011, 13 pages.
Final Office Action dated Sep. 20, 2013, for U.S. Appl. No. 13/644,780, filed Oct. 4, 2012, 16 pages.
Final Office Action dated Nov. 12, 2013, for U.S. Appl. No. 13/644,748, filed Oct. 4, 2012, 8 pages.
Final Office Action dated Jan. 8, 2014, for U.S. Appl. No. 13/644,758, filed Oct. 4, 2012, 8 pages.
Final Office Action dated Sep. 3, 2014, for U.S. Appl. No. 13/644,758, filed Oct. 4, 2012, 8 pages.
Final Office Action dated Apr. 23, 2015, for U.S. Appl. No. 14/527,292, filed Oct. 29, 2014, 8 pages.
Final Office Action dated Aug. 19, 2015, for U.S. Appl. No. 13/445,816, filed Apr. 12, 2012, 6 pages.
Final Office Action dated Mar. 9, 2016, for U.S. Appl. No. 14/539,648, filed Nov. 12, 2014, 11 pages.
International Search Report dated Nov. 30, 2007, for PCT Application No. PCT/US2007/013038, filed May 31, 2007, 4 pages.
International Search Report dated Apr. 5, 2011, for PCT Application No. PCT/US2011/023643, filed Feb. 3, 2011, 2 pages.
International Search Report dated Feb. 1, 2013 for PCT Application No. PCT/US2012/058751, filed Oct. 4, 2012, 4 pages.
International Search Report dated Sep. 14, 2015, for PCT Application No. PCT/US2015/023720, filed Mar. 31, 2015, 5 pages.
Non-Final Office Action dated May 17, 2010, for U.S. Appl. No. 11/475,523, filed Jun. 26, 2006, 10 pages.
Non-Final Office Action dated Jan. 26, 2012, for U.S. Appl. No. 12/695,053, filed Jan. 27, 2010, 10 pages.
Non-Final Office Action dated Mar. 15, 2012, for U.S. Appl. No. 13/245,811, filed Sep. 26, 2011, 4 pages.
Non-Final Office Action dated May 11, 2012, for U.S. Appl. No. 13/020,706, filed Feb. 3, 2011, 5 pages.
Non-Final Office Action dated Nov. 9, 2012, for U.S. Appl. No. 13/245,811, filed Sep. 26, 2011, 5 pages.
Non-Final Office Action dated Apr. 24, 2013, for U.S. Appl. No. 13/644,780, filed Oct. 4, 2012, 13 pages.
Non-Final Office Action dated Jun. 12, 2013, for U.S. Appl. No. 13/644,748, filed Oct. 4, 2012, 8 pages.
Non-Final Office Action dated Sep. 9, 2013, for U.S. Appl. No. 13/644,758, filed Oct. 4, 2012, 7 pages.
Non-Final Office Action dated Feb. 7, 2014, for U.S. Appl. No. 13/644,780, filed Oct. 4, 2012, 12 pages.
Non-Final Office Action dated Feb. 24, 2014, for U.S. Appl. No. 13/025,112, filed Feb. 10, 2011, 12 pages.
Non-Final Office Action dated May 15, 2014, for U.S. Appl. No. 13/644,758, filed Oct. 4, 2012, 7 pages.
Non-Final Office Action dated Nov. 28, 2014, for U.S. Appl. No. 13/644,748, filed Oct. 4, 2012, 7 pages.
Non-Final Office Action dated Jan. 14, 2015, for U.S. Appl. No. 13/644,758, filed Oct. 4, 2012, 10 pages.
Non-Final Office Action dated Feb. 4, 2015, for U.S. Appl. No. 13/445,816, filed Apr. 12, 2012, 6 pages.
Non-Final Office Action dated Feb. 23, 2015, for U.S. Appl. No. 13/025,112, filed Feb. 10, 2011, 17 pages.
Non-Final Office Action dated Jul. 10, 2015, for U.S. Appl. No. 13/025,112, filed Feb. 10, 2011, 16 pages.
Non-Final Office Action dated Oct. 7, 2015, U.S. Appl. No. 14/527,292, filed Oct. 29, 2014, 5 pages.
Non-Final Office Action dated Nov. 3, 2015, for U.S. Appl. No. 14/539,648, filed Nov. 12, 2014, 7 pages.
Non-Final Office Action dated Dec. 14, 2015, for U.S. Appl. No. 13/445,816, filed Apr. 12, 2012, 7 pages.
Non-Final Office Action dated Feb. 25, 2016, for U.S. Appl. No. 13/644,769, filed Oct. 4, 2012, 19 pages.
Notice of Allowance dated Feb. 2, 2011, for U.S. Appl. No. 11/475,523, filed Jun. 26, 2006, 6 pages.
Notice of Allowance dated Jun. 11, 2012, for U.S. Appl. No. 12/695,053, filed Jan. 27, 2010, 7 pages.
Notice of Allowance dated Apr. 2, 2013, for U.S. Appl. No. 13/245,811, filed Sep. 26, 2011, 6 pages.
Notice of Allowance dated May 10, 2013, for U.S. Appl. No. 13/020,706, filed Feb. 3, 2011, 8 pages.
Notice of Allowance dated Jul. 7, 2014, for U.S. Appl. No. 14/012,963, filed Aug. 28, 2013, 6 pages.
Notice of Allowance dated Jul. 23, 2014, for U.S. Appl. No. 13/644,780, filed Oct. 4, 2012, 8 pages.
Notice of Allowance dated Mar. 30, 2015, for U.S. Appl. No. 13/644,748, filed Oct. 4, 2012, 5 pages.
Notice of Allowance dated Aug. 10, 2015, for U.S. Appl. No. 13/644,758, filed Oct. 4, 2012, 7 pages.
Notice of Allowance dated Mar. 1, 2016, for U.S. Appl. No. 13/025,112, filed Feb. 10, 2011, 7 pages.
Restriction Requirement dated Sep. 30, 2009, for U.S. Appl. No. 11/475,523, filed Jun. 26, 2006, 9 pages.
Restriction Requirement dated Feb. 23, 2010, for U.S. Appl. No. 11/475,523, filed Jun. 26, 2006, 6 pages.
Restriction Requirement dated Mar. 28, 2012, for U.S. Appl. No. 13/020,706, filed Feb. 3, 2011, 7 pages.
Restriction Requirement dated Sep. 15, 2014, for U.S. Appl. No. 13/445,816, filed Apr. 12, 2012, 6 pages.
Restriction Requirement dated Sep. 25, 2015, for U.S. Appl. No. 13/644,769, filed Oct. 4, 2012, 6 pages.

(56) References Cited

OTHER PUBLICATIONS

Supplementary European Search Report dated Mar. 24, 2016, for European Patent Application No. 12871982.0, filed on Oct. 4, 2012, 7 pages.
Written Opinion dated Nov. 30, 2007, for PCT Application No. PCT/US2007/013038, filed on May 31, 2007, 6 pages.
Written Opinion dated Apr. 5, 2011, for PCT Application No. PCT/US2011/023643, filed on Feb. 3, 2011, 6 pages.
Written Opinion dated Feb. 1, 2013 for PCT Application No. PCT/US2012/058751, filed on Oct. 4, 2012, 6 pages.
Written Opinion dated Sep. 14, 2015 for PCT Application No. PCT/US2015/023720, filed on Mar. 31, 2015, 8 pages.
Extended European Search Report dated Jun. 9, 2016, for European Patent Application No. 16 155 079.3, filed on May 31, 2007, 7 pages.
Extended European Search Report dated May 17, 2011, for European Patent Application No. 11 162 487.0, filed on May 31, 2007, 6 pages.
Final Office Action dated Oct. 3, 2016, for U.S. Appl. No. 13/644,769, filed Oct. 4, 2012, 27 pages.
Non-Final Office Action dated Jun. 7, 2016, for U.S. Appl. No. 14/527,292, filed Oct. 29, 2014, 5 pages.
Non-Final Office Action dated Jan. 18, 2017, for U.S. Appl. No. 14/539,648, filed Nov. 12, 2014, 13 pages.
Corrected Notice of Allowability dated Apr. 25, 2016, U.S. Appl. No. 13/025,112, filed Feb. 10, 2011, 2 pages.
Notice of Allowance dated Jul. 13, 2016, for U.S. Appl. No. 13/445,816, filed Apr. 12, 2012, 7 pages.
Corrected Notice of Allowability dated Sep. 1, 2016, for U.S. Appl. No. 13/445,816, filed Apr. 12, 2012, 2 pages.
U.S. Appl. No. 15/343,147, filed Nov. 3, 2016, by Badawi et al.
U.S. Appl. No. 15/340,911, filed Nov. 1, 2016, by Badawi et al.
Final Office Action dated May 18, 2017, for U.S. Appl. No. 14/539,648, filed Nov. 12, 2014, 14 pages.
Final Office Action dated Jan. 29, 2018, for U.S. Appl. No. 14/973,620, filed Dec. 17, 2015, 19 pages.
Final Office Action dated Apr. 6, 2018, for U.S. Appl. No. 15/683,652, filed Aug. 22, 2017, 11 pages.
Final Office Action dated Jun. 1, 2018, for U.S. Appl. No. 14/816,822, filed Aug. 3, 2015, 6 pages.
Non-Final Office Action dated Mar. 22, 2017, for U.S. Appl. No. 13/644,769, filed Oct. 4, 2012, 31 pages.
Non-Final Office Action dated Aug. 28, 2017, for U.S. Appl. No. 14/973,620, filed Dec. 17, 2015, 6 pages.
Non-Final Office Action dated Nov. 7, 2017, for U.S. Appl. No. 14/816,822, filed Aug. 3, 2015, 14 pages.
Non-Final Office Action dated Dec. 15, 2017, for U.S. Appl. No. 15/343,147, filed Nov. 3, 2016, 12 pages.
Non-Final Office Action dated Aug. 9, 2018, for U.S. Appl. No. 15/182,165, filed Jun. 14, 2016, 9 pages.
Non-Final Office Action dated Aug. 29, 2018, for U.S. Appl. No. 14/973,620, filed Dec. 17, 2015, 11 pages.
Notice of Allowance dated Oct. 25, 2017, for U.S. Appl. No. 13/644,769, filed Oct. 4, 2012, 8 pages.
Notice of Allowance dated Nov. 21, 2017, for U.S. Appl. No. 14/539,648, filed Nov. 12, 2014, 10 pages.
Notice of Allowance dated Aug. 31, 2018, for U.S. Appl. No. 14/816,822, filed Aug. 3, 2015, 7 pages.
Corrected Notice of Allowability dated Nov. 23, 2018, for U.S. Appl. No. 14/816,822, filed Aug. 3, 2015, 2 pages.
Final Office Action dated Oct. 19, 2018, for U.S. Appl. No. 15/683,652, filed Aug. 22, 2017, 8 pages.
Non-Final Office Action dated Sep. 20, 2018, for U.S. Appl. No. 15/340,911, filed Nov. 1, 2016, 7 pages.
Extended European Search Report dated Nov. 20, 2018, for European Patent Application No. 15 888 007.0, filed on Mar. 31, 2015, 9 pages.

* cited by examiner

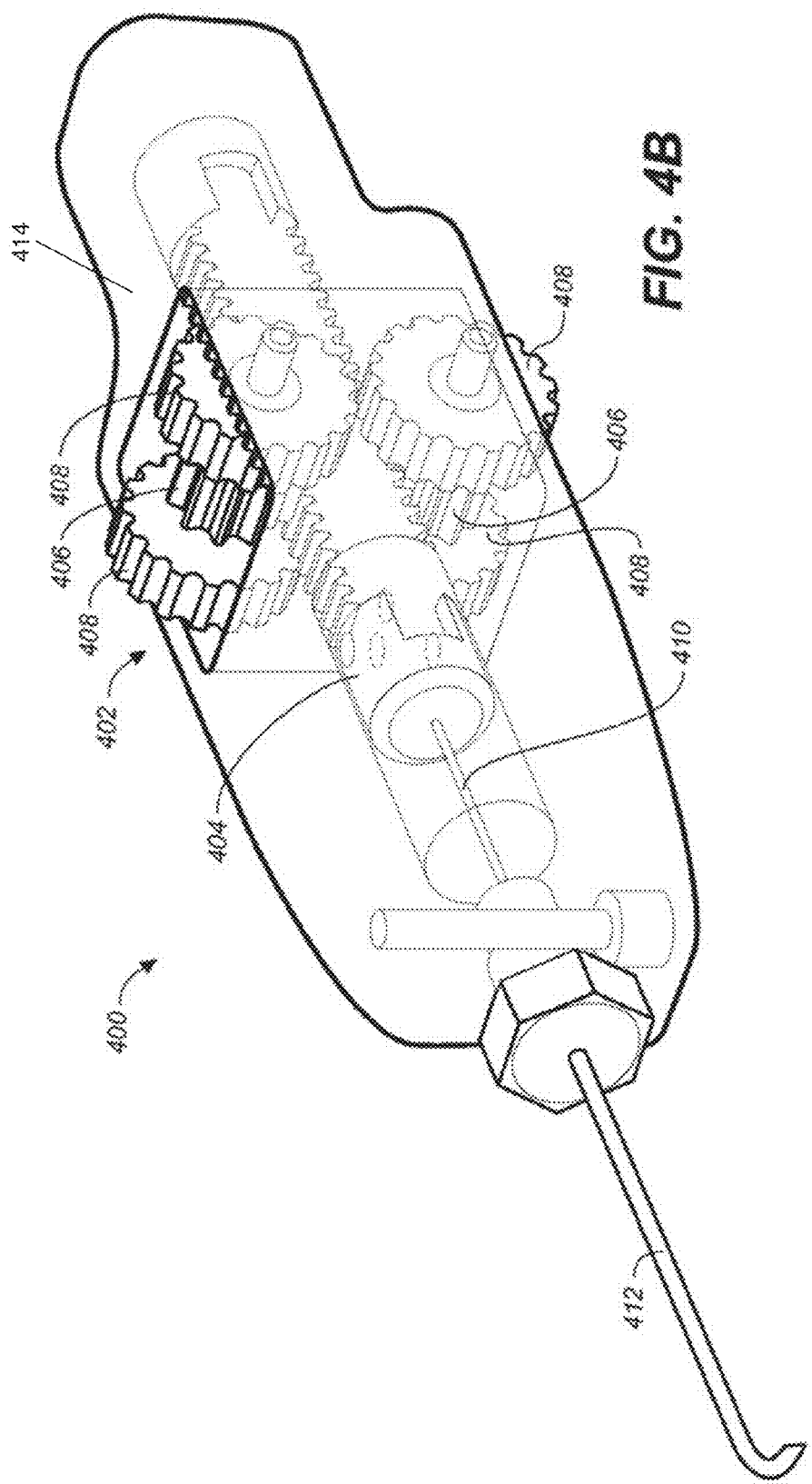

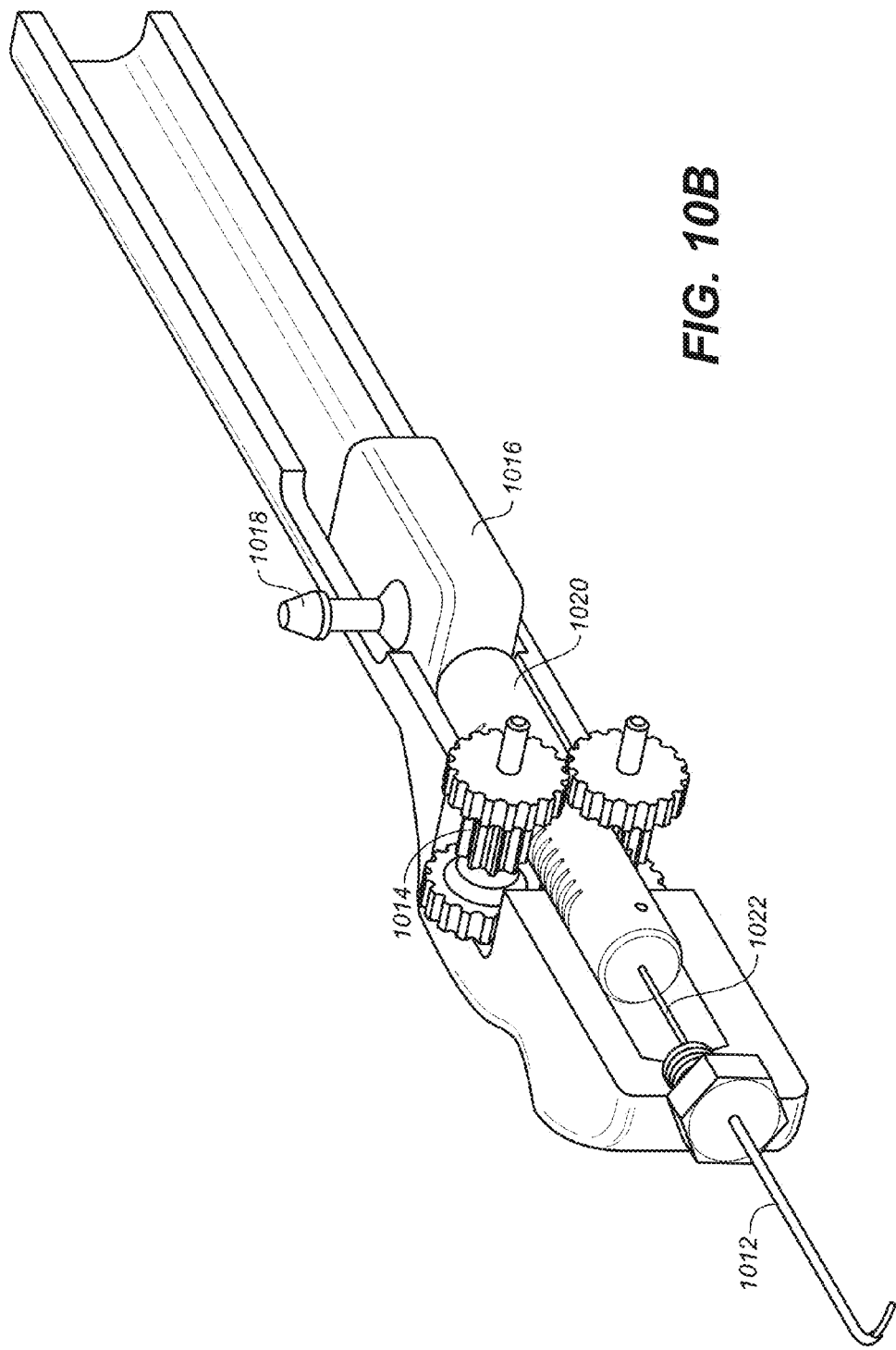

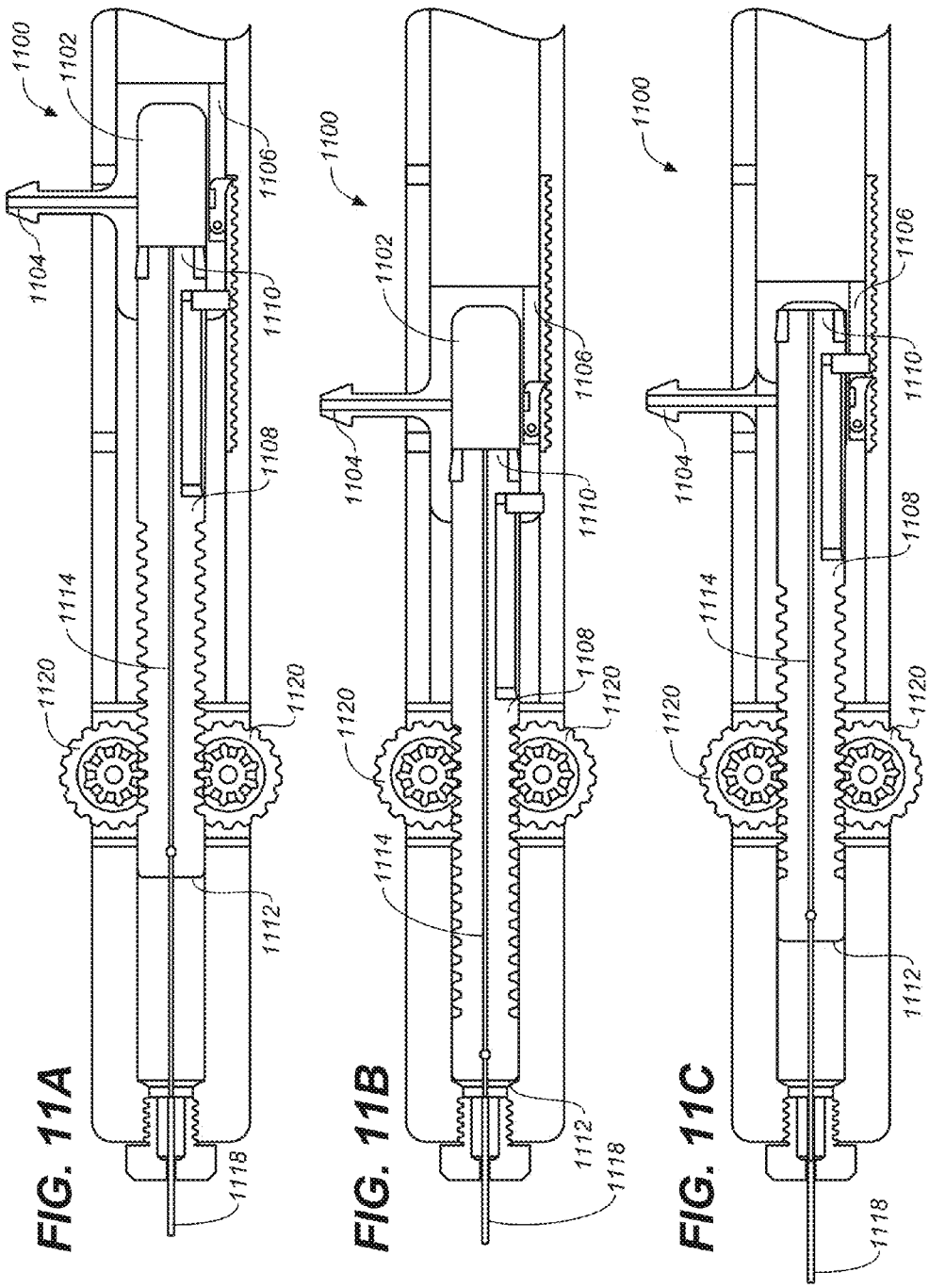

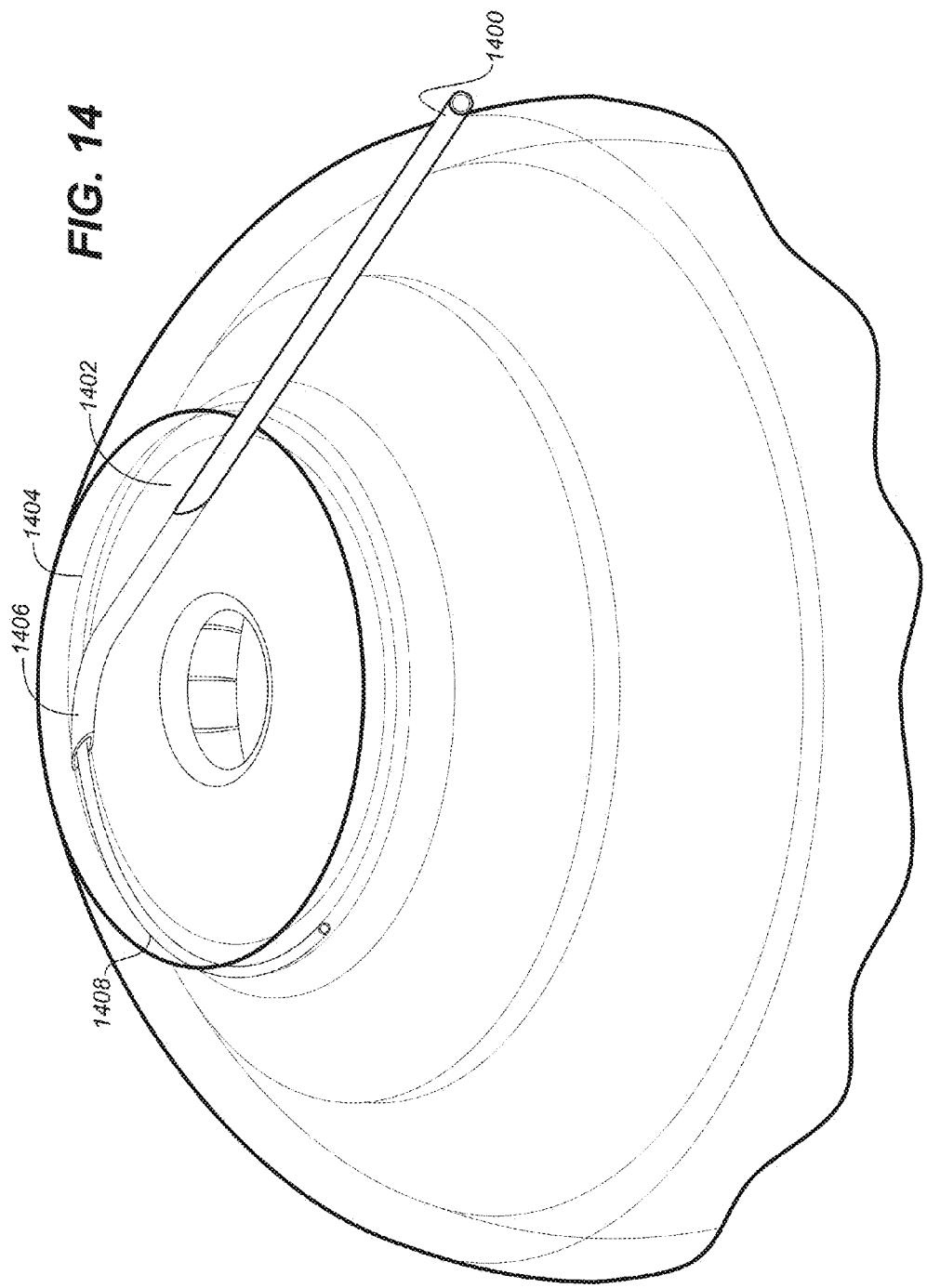

OCULAR DELIVERY SYSTEMS AND METHODS

FIELD

Described here are systems and methods for accessing Schlemm's canal in an eye and for delivering an ocular device, tool, or fluid composition therein. The ocular devices may maintain the patency of Schlemm's canal without substantially interfering with transmural, transluminal, circumferential, or longitudinal aqueous humor fluid flow across the canal. The tools delivered may be used to disrupt the trabecular meshwork. The fluid composition may be a viscoelastic fluid that is delivered into the canal or aqueous collector channels to facilitate drainage of aqueous humor by dilating the canal, disrupting juxtacanalicular meshwork and the adjacent wall of Schlemm's canal, and/or increasing aqueous permeability through the trabeculocanalicular, or transmural, outflow pathway. Minimally invasive methods for treating medical conditions associated with elevated intraocular pressure, including glaucoma, are also described.

BACKGROUND

Glaucoma is a potentially blinding disease that affects over 60 million people worldwide, or about 1-2% of the population. Typically, glaucoma is characterized by elevated intraocular pressure. Increased pressure in the eye can cause irreversible damage to the optic nerve which can lead to loss of vision and even progress to blindness if left untreated. Consistent reduction of intraocular pressure can slow down or stop progressive loss of vision associated with glaucoma.

Increased intraocular pressure is generally caused by sub-optimal efflux or drainage of fluid (aqueous humor) from the eye. Aqueous humor or fluid is a clear, colorless fluid that is continuously replenished in the eye. Aqueous humor is produced by the ciliary body, and then ultimately exits the eye primarily through the trabecular meshwork. The trabecular meshwork extends circumferentially around the eye at the anterior chamber angle, or drainage angle, which is formed at the intersection between the peripheral iris or iris root, the anterior sclera or scleral spur and the peripheral cornea. The trabecular meshwork feeds outwardly into Schlemm's canal, a narrow circumferential passageway generally surrounding the exterior border of the trabecular meshwork. Positioned around and radially extending from Schlemm's canal are aqueous veins or collector channels that receive drained fluid. The net drainage or efflux of aqueous humor can be reduced as a result of decreased facility of outflow, decreased outflow through the trabecular meshwork and canal of Schlemm drainage apparatus, increased episcleral venous pressure, or possibly, increased production of aqueous humor. Flow out of the eye can also be restricted by blockages or constriction in the trabecular meshwork and/or Schlemm's canal and its collector channels.

Glaucoma, pre-glaucoma, and ocular hypertension currently can be treated by reducing intraocular pressure using one or more modalities, including medication, incisional surgery, laser surgery, cryosurgery, and other forms of surgery. In general, medications or medical therapy are the first lines of therapy. If medical therapy is not sufficiently effective, more invasive surgical treatments may be used. For example, a standard incisional surgical procedure to reduce intraocular pressure is trabeculectomy, or filtration surgery. This procedure involves creating a new drainage site for aqueous humor. Instead of naturally draining through the trabecular meshwork, a new drainage pathway is created by removing a portion of sclera and trabecular meshwork at the drainage angle. This creates an opening or passage between the anterior chamber and the subconjunctival space that is drained by conjunctival blood vessels and lymphatics. The new opening may be covered with sclera and/or conjunctiva to create a new reservoir called a bleb into which aqueous humor can drain. However, traditional trabeculectomy procedures carry both short and long term risks. These risks include blockage of the surgically-created opening through scarring or other mechanisms, hypotony or abnormally low intraocular pressure, expulsive hemorrhage, hyphema, intraocular infection or endophthalmitis, shallow anterior chamber angle, macular hypotony, choroidal exudation, suprachoroidal hemorrhage, and others.

One alternative is to implant a device in Schlemm's canal that maintains the patency of the canal or aids flow of aqueous humor from the anterior chamber into the canal. Various stents, shunts, catheters, and procedures have been devised for this purpose and employ an ab-externo (from the outside of the eye) approach to deliver the implant or catheter into Schlemm's canal. This method of placement is invasive and typically prolonged, requiring the creation of tissue flaps and deep dissections to access the canal. Additionally, it is very difficult for many surgeons to find and access Schlemm's canal from this external incisional approach because Schlemm's canal has a small diameter, e.g., approximately 50 to 250 microns in cross-sectional diameter, and it may be even smaller when collapsed. One such procedure, ab-externo canaloplasty, involves making a deep scleral incision and flap, finding and unroofing Schlemm's canal, circumnavigating all 360 degrees of the canal with a catheter from the outside of the eye, and either employing viscoelastic, a circumferential tensioning suture, or both to help maintain patency of the canal. The procedure is quite challenging and can take anywhere from forty-five minutes to two hours. The long-term safety and efficacy of canaloplasty is very promising, but the procedure remains surgically challenging and invasive.

Another alternative is viscocanalostomy, which involves the injection of a viscoelastic solution into Schlemm's canal to dilate the canal and associated collector channels. Dilation of the canal and collector channels in this manner generally facilitates drainage of aqueous humor from the anterior chamber through the trabecular meshwork and Schlemm's canal, and out through the natural trabeculocanalicular outflow pathway. Viscocanalostomy is similar to canaloplasty (both are invasive and ab-externo), except that viscocanalostomy does not involve a suture and does not restore all 360 degrees of outflow facility. Some advantages of viscocanalostomy are that sudden drops in intraocular pressure, hyphema, hypotony, and flat anterior chambers may be avoided. The risk of cataract formation and infection may also be minimized because of reduced intraocular manipulation and the absence of full eye wall penetration, anterior chamber opening and shallowing, and iridectomy. A further advantage of viscocanalostomy is that the procedure restores the physiologic outflow pathway, thus avoiding the need for external filtration, and its associated short and long term risks, in the majority of eyes. This makes the success of the procedure partly independent of conjunctival or episcleral scarring, which is a leading cause of failure in traditional trabeculectomy procedures. Moreover, the absence of an elevated filtering bleb avoids related ocular discomfort and potentially devastating ocular infections, and the procedure can be carried out in any quadrant of the outflow pathway.

However, current viscocanalostomy and canaloplasty techniques are still very invasive because access to Schlemm's canal must be created by making a deep incision into the sclera, creating a scleral flap, and un-roofing Schlemm's canal. In their current forms, these procedures are both "ab-externo" procedures. "Ab-externo" generally means "from the outside" and it is inherently more invasive given the location of Schlemm's canal and the amount of tissue disruption required to access it from the outside. On the other hand, "ab-interno" means "from the inside" and is a less invasive approach because of the reduced amount of tissue disruption required to access it from the inside. Consequently, an ab-interno approach to Schlemm's canal offers the surgeon easier access to the canal, but also reduces risk to the patient's eye and reduces patient morbidity. All of these lead to improved patient recovery and rehabilitation. The ab-externo viscocanalostomy and canaloplasty procedures also remain challenging to surgeons, because as previously stated, it is difficult to find and access Schlemm's canal from the outside using a deep incisional approach due to the small diameter of Schlemm's canal. A further drawback still is that at most, viscocanalostomy typically dilates up to 60 degrees of Schlemm's canal, which is a 360 degree ring-shaped outflow vessel-like structure. The more of the canal that can be dilated, the more total aqueous outflow can be restored.

Accordingly, it would be beneficial to have systems that easily and atraumatically provide access to Schlemm's canal using an ab-interno approach for the delivery of ocular devices, tools, and compositions. It would also be useful to have systems that deliver devices, tools, and compositions into Schlemm's canal expeditiously to decrease procedure time and the risk of infection without compromising safety and precision of the delivery procedure. It would also be useful to have systems that deliver devices, tools, and fluid compositions into Schlemm's canal using an ab-interno approach so that cataract surgery and glaucoma surgery can both be accomplished during the same surgical sitting using the very same corneal or scleral incision. Such incisions are smaller and allow for less invasive surgery and more rapid patient recovery. This approach allows for accessing Schlemm's canal through the trabecular meshwork from the inside of the eye, and thus it is called "ab-interno." Methods of delivering ocular devices, tools, and compositions that effectively disrupt the juxtacanalicular meshwork and adjacent wall of Schlemm's canal, also known as the inner wall of Schlemm's canal, maintain the patency of Schlemm's canal, increase outflow, decrease resistance to outflow, or effectively dilate the canal and/or its collector channels using the systems in a minimally invasive, ab-interno manner would also be desirable.

BRIEF SUMMARY

Described here are systems and methods for easily and reliably accessing Schlemm's canal with minimal or reduced trauma and for delivering an ocular device (e.g., an implant) therein. Other systems and methods may be implant-free, and/or rely on the delivery and removal of a therapeutic (disruptive) tool and/or the delivery of a fluid composition into Schlemm's canal to improve flow through the trabeculocanalicular outflow system, which consists of the trabecular meshwork, juxtacanalicular tissue, Schlemm's canal, and collector channels. When an ocular device is implanted, the ocular device may maintain the patency of Schlemm's canal without substantially interfering with transmural fluid flow across the canal. Transmural flow, or transmural aqueous humor flow, is defined as flow of aqueous humor from the anterior chamber across the trabecular meshwork into the lumen of Schlemm's canal, across and along the lumen of Schlemm's canal, and ultimately into aqueous collector channels originating in the outer wall of Schlemm's canal. When a fluid composition is delivered into the canal, the fluid composition, e.g., a viscoelastic fluid, delivered into the canal may facilitate drainage of aqueous humor by dilating the canal, rendering the trabecular meshwork and inner wall of Schlemm's canal more permeable to aqueous humor, and also dilating aqueous collector channels. When a therapeutic tool is delivered, the tool may facilitate drainage of aqueous humor by dilating the canal, dilating the collector channels, disrupting or stretching the trabecular meshwork, disrupting or stretching the juxtacanalicular tissue, tearing or cutting the trabecular meshwork or juxtacanalicular tissue, or completely removing the trabecular meshwork or juxtacanalicular tissue. Any or all of these actions may reduce resistance to outflow, increase aqueous outflow and drainage, and reduce intraocular pressure.

One of the beneficial features of the system may be a cannula configured with a distal curved portion that defines a radius of curvature, where the radius of curvature directly engages the bevel at the distal tip of the cannula. However, in some variations, the system may comprise a straight cannula. The specific configuration of the handle of the system may also be useful. The handle may be sized and shaped so that it is easily manipulated with one hand. Furthermore, the handle may be designed for universal manipulation. By "universal" it is meant that the handle is ergonomically configured for both right-handed and left-handed use, for use to access any quadrant of the eye, and for use in advancing a cannula or elongate member into Schlemm's canal in a clockwise or counterclockwise fashion. Such a configuration may include a drive assembly that can be easily actuated in a first orientation (e.g., to deliver an implant, tool, and/or fluid in a clockwise fashion) and that can be easily actuated in a second, flipped orientation (e.g., to deliver an implant, tool, and/or fluid in a counterclockwise fashion). Such a configuration may allow the drive assembly to be actuated using either a left hand or a right hand, and may allow the drive assembly to be used with either the left eye or the right eye. Alternatively, in some variations the cannula itself can be rotated to the extent needed (e.g., 180 degrees) to provide ambidextrous ease of use in a clockwise or counterclockwise advancement direction.

The ocular delivery systems described herein generally include a universal handle having a grip portion and a housing that has an interior and a distal end. A cannula is typically coupled to and extends from the housing distal end. The cannula may include a proximal end and a distal curved portion, where the distal curved portion has a proximal end and a distal end, and a radius of curvature defined between the ends. The cannula may also be configured to include a body; a distal tip having a bevel; and a lumen extending from the proximal end through the distal tip. The bevel may directly engage the distal end of the curved portion of the cannula (i.e., the bevel may directly engage the radius of curvature). The systems may also generally include a drive assembly substantially contained within the housing comprising gears that translate rotational movement to linear movement.

When an ocular device is to be implanted into Schlemm's canal, the system may further include a slidable positioning element having a proximal end and a distal end that is coaxially disposed within the cannula lumen. The distal end of the slidable positioning element may comprise an engagement mechanism for positioning (including manipulating) the ocular device within the canal. Exemplary engagement mechanisms that may be employed comprise hooks, jaws, clasps, forceps, or complimentary mating elements for releasable attachment of the ocular devices.

The system may be configured to include a fluid assembly in the handle and an elongate member comprising a lumen coaxially disposed within the cannula lumen when a fluid composition is to be delivered into Schlemm's canal. The fluid composition may be delivered through the distal end of the lumen of elongate member or through openings spaced along the axial length of the elongate member. Additionally, the fluid assembly may be coupled to a loading component configured to transfer fluid compositions into a reservoir at least partially defined by the assembly. Some variations of the system may have the fluid composition preloaded in the reservoir. Exemplary fluid compositions include without limitation, saline, pharmaceutical compounds, and viscoelastic fluids. The viscoelastic fluids may comprise hyaluronic acid, chondroitin sulfate, cellulose, or salts, derivatives, or mixtures thereof. Use of sodium hyaluronate as the viscoelastic fluid may be beneficial. Some systems may be configured to deliver a therapeutic (disruptive) tool to Schlemm's canal, without the delivery of an implant or fluid. In these variations, the handle may or may not include a fluid reservoir, and the tool may have various configurations to disrupt tissue. An exemplary system may comprise an elongate member comprising an atraumatic distal tip configured to be advanced through Schlemm's canal, and configured such that the body of the elongate member tears or cuts through the trabecular meshwork when the system is removed from the eye.

Methods for implanting an ocular device within Schlemm's canal are also described. Using the ocular delivery systems disclosed herein, the method generally includes the steps of creating an incision in the ocular wall that provides access to the anterior chamber of the eye; advancing a cannula of the system through the incision, across a portion of the anterior chamber, to the trabecular meshwork, and piercing the trabecular meshwork; accessing Schlemm's canal with the cannula; and implanting the device within the canal. The cannula will typically comprise a proximal end and a distal curved portion, the distal curved portion having a proximal end and a distal end and a radius of curvature defined between the ends; a body; a distal tip having a bevel, the bevel directly engaging the distal end of the curved portion of the cannula; and a lumen extending from the proximal end through the distal tip. A positioning element slidable within the cannula lumen may be employed during the step of implanting the device within the canal. The device may be implanted to reduce intraocular pressure or to treat a medical condition such as glaucoma, pre-glaucoma, or ocular hypertension.

Methods for delivering a fluid composition into Schlemm's canal are further described. Using the ocular delivery systems disclosed herein, the method generally includes the steps of creating an incision in the ocular wall that provides access to the anterior chamber of the eye; advancing a cannula of the system through the incision to the trabecular meshwork; accessing Schlemm's canal with the cannula; and delivering the fluid composition into Schlemm's canal using a elongate member comprising a lumen andslidable within the cannula lumen. The cannula will typically comprise a proximal end and a distal curved portion, the distal curved portion having a proximal end and a distal end and a radius of curvature defined between the ends; a body; a distal tip having a bevel, the bevel directly engaging the distal end of the curved portion of the cannula; and a lumen extending from the proximal end through the distal tip. The fluid composition may be delivered into Schlemm's canal through the distal end of the elongate member or through openings spaced along the axial length of the elongate member. Fluids such as saline and viscoelastic solutions may be delivered into the canal to dilate the canal and collector channels and/or to disrupt the juxtacanalicular meshwork or inner wall of Schlemm's canal to enhance permeability to aqueous humor, reduce resistance to aqueous outflow, or increase aqueous outflow. Examples of viscoelastic solutions are those that include hyaluronic acid, chondroitin sulfate, cellulose, and derivatives and mixtures thereof. As previously stated, the use of sodium hyaluronate as the viscoelastic solution may be beneficial. Drugs for treating glaucoma, steroids, anti-neovascularization (e.g., anti-vascular endothelial growth factor (anti-VEGF) antibodies and derivatives), anti-inflammatory, or antifibrotic drugs may also be combined with the viscoelastic solutions. The drugs may also be delivered alone without viscoelastic if desired.

When the fluid composition is delivered, the delivery step may include actuation of the drive assembly so that retraction of at least a portion of the gears (or reversal of gear movement) pressurizes the reservoir in an amount sufficient to force the fluid composition through the lumen of the elongate member. The fluid composition may be delivered to dilate Schlemm's canal. The fluid composition may also be delivered to reduce intraocular pressure or to treat a medical condition such as glaucoma.

The systems, devices, and methods described herein may also employ varying degrees of force to disrupt trabeculo-canalicular tissues, e.g., the trabecular meshwork, juxtacanalicular tissue, Schlemm's canal, walls of Schlemm's canal, septae, obstructions, or narrowings inside Schlemm's canal, and collector channels, to improve drainage of aqueous humor and in turn, reduce intraocular pressure and treat conditions of the eye. The disruptive force may be generated by implant-free methods, e.g., by delivering a disruptive volume of viscoelastic fluid which may expand the canal and collector channels and may also stretch the trabecular meshwork, advancing disruptive tools, e.g., cannulas, conduits, catheters, dilation probes, balloons, etc., which may or may not include one or more disruptive components on their distal portions, or both. Depending on factors such as the type or severity of the condition being treated, the disruptive force may be generated to partially cut, tear, stretch, dilate, destroy, or completely destroy and/or remove, the trabecular meshwork and/or juxtacanalicular tissue, and may be adjusted by varying the volume of viscoelastic fluid delivered, or by varying the tool configuration, as further discussed below.

The viscoelastic or aqueous fluid may be delivered using a unitary and single-handed, single-operator controlled system. Advancement of the disruptive tools may also be provided by a unitary and single-handed, single-operator controlled system. By "unitary" it is meant that one systemis employed to advance an elongate member through at least a portion of Schlemm's canal, and in some instances to also deliver a viscoelastic fluid, tool, or implant into Schlemm's canal. By "single-operator controlled" it is meant that all features of the system, e.g., cannula, elongate member, and tool advancement and retraction, ocular device delivery, fluid delivery, etc., can be performed by one user. This is in contrast to other systems that use forceps to advance a delivery catheter into Schlemm's canal and/or devices containing viscoelastic fluid that are separate or independent from a delivery catheter, and which require connection to the delivery catheter during a procedure by an assistant or assistants while the delivery catheter is held by the surgeon. Following delivery of a disruptive volume of fluid or a tool, an implant, e.g., a helical support or scaffold, may be advanced into Schlemm's canal to maintain its patency, or energy delivered to modify the structure of Schlemm's canal and/or the surrounding trabeculocanalicular tissues.

The single-handed, single-operator controlled system for delivering fluids may include a cannula; an elongate member comprising a lumen and slidably disposed within, and advanceable distally from, the cannula; and a handle coupled to the cannula, where a portion of the handle defines a fluid reservoir, and where the handle is capable of being operated with a single-hand to deliver the fluid from the reservoir through the lumen of the elongate member.

Alternatively, a system for delivering viscoelastic fluids may include a cannula; a elongate member comprising a lumen and slidably disposed within, and advanceable distally from, the cannula; a handle coupled to the cannula, where a portion of the handle defines a fluid reservoir; and a linear gear moveable to advance a fluid from the fluid reservoir through the lumen of the elongate member.

The system for delivering viscoelastic fluids may also be configured to include a universal handle having a proximal end and a distal end; a cannula extending from the distal end and having a proximal portion and a distal portion; a slidable elongate member comprising a lumen and disposed within the cannula; a housing having an interior and upper and lower surfaces; and a wheeled drive assembly; where the wheeled drive assembly extends past the upper and lower surfaces of the housing. Such a system having a universal handle may further include a rotating cannula that can be rotated, e.g., from a left to right position, and a wheeled drive assembly that comprises a single wheel (rotatable component) configured to slide the elongate member. Instead of a wheel, a button, slide, foot pedal, or motorized mechanism could also be configured to slide the elongate member.

In all variations of the viscoelastic fluid delivery systems, the elongate member may comprise a lumen and may have an outer diameter ranging from about 25 microns to about 1000 microns, from about 25 microns to about 500 microns, from about 50 microns to about 500 microns, from about 150 microns to about 500 microns, from about 200 microns to about 500 microns, from about 300 microns to about 500 microns, from about 200 microns to about 250 microns, or from about 180 microns to about 300 microns. In some instances it may be beneficial for the elongate member to have an outer diameter of about 240 microns. The elongate member may also comprise a plurality of openings spaced along at least a portion of its axial length or have a distal end with a cut out configured as a half tube.

In addition to disrupting Schlemm's canal and the surrounding trabeculocanalicular tissues using a disruptive volume of viscoelastic fluid, the outer diameter of the elongate member may be sized to disrupt those tissues. For example, an elongate member having an outer diameter ranging from about 200 microns to about 500 microns may be beneficial for disrupting tissues. Furthermore, a distal portion of the elongate member may include a disruptive component, e.g., a notch, hook, barb, balloon, or combinations thereof, that disrupts tissues. However, the systems may not need to include both features, i.e., deliver a disruptive volume of viscoelastic fluid and also have a elongate member sized for disruption. An elongate member configured for disruption of Schlemm's canal and surrounding tissues may be used alone to reduce intraocular pressure, without the delivery of fluids. Such an elongate member may or may not have a lumen. In some variations, the elongate member may be configured such that the body of the elongate member cuts or tears the trabecular meshwork as the system is removed from the eye. Elongate members may also be configured to comprise a balloon or be otherwise inflatable or expandable to a size that disrupts tissues as it is advanced.

The handle of the viscoelastic fluid delivery systems described herein may include a drive assembly capable of causing the fluid to be delivered from the reservoir through the lumen of the elongate member. The drive assembly may be a wheeled drive assembly that includes one rotatable component or a plurality of rotatable components. The reservoir may be preloaded with the viscoelastic fluid. Exemplary viscoelastic fluids may comprise hyaluronic acid, chondroitin sulfate, cellulose, polymers, or salts, derivatives, or mixtures thereof. It may be beneficial to use sodium hyaluronate as the viscoelastic fluid.

In some variations, the systems for introducing a fluid composition into Schlemm's canal described here may comprise a housing, a cannula, a flexible elongate member, a reservoir, and a drive assembly. The cannula may be attached to the distal end of the housing and may comprise a distal tip. The flexible elongate member may comprise a lumen and a distal end, and the distal end may be slidable within the cannula between a retracted position and an extended position. The distal end may be within the cannula in the retracted positioned and distal to the distal tip of the cannula in the extended position. The reservoir may comprise a fluid composition and the reservoir may be fluidly connected to the lumen of the flexible elongate member. The drive assembly may be configured to simultaneously move the flexible elongate member from the extended position to the retracted position and may deliver the fluid composition from the reservoir through the lumen of the flexible elongate member. In some variations, the system may further comprise a lock that may be configured to resist movement of the reservoir relative to the housing. In some instances, the system may be configured to prevent movement of the flexible elongate member toward the extended position after the flexible elongate member has been retracted a fixed cumulative distance. In some of these instances, the fixed cumulative distance may be about 40 mm.

In some instances, the drive assembly may comprise a linear gear. The translation of the linear gear in a first direction may move the flexible elongate member toward the retracted configuration and may deliver the fluid composition from the reservoir through the lumen of the elongate member. In some of these instances, translation of the linear gear in a second direction may move the flexible elongate member toward the extended configuration. The volume of fluid composition delivered from the reservoir may correspond to a distance of movement of the flexible polymeric elongate member toward the extended configuration. In some variations, the drive assembly may further comprise a rotatable component and rotation of the rotatable component may cause translations of the linear gear. In some instances, the volume of fluid composition delivered from the reservoir may correspond to a distance of translation of the linear gear in the first direction.

Also described here is a device for introducing a fluid composition into Schlemm's canal. The device may comprise a housing, a reservoir, a flexible polymeric elongate member, and a drive assembly. The reservoir may hold the fluid composition and may be located within the housing.

The flexible polymeric elongate member may comprise a lumen fluidly connected to the reservoir. The drive assembly may be configured to cause a volume of fluid composition to be delivered from the reservoir to Schlemm's canal via the lumen of the flexible polymeric elongate member and may cause the flexible polymeric elongate member to translate by a distance relative to the housing. The volume of fluid composition delivered may be fixed relative to the distance translated by the flexible elongate member. In some variations, the drive assembly may comprise a rotatable wheel and the volume of fluid composition delivered and the distance translated by the flexible polymeric elongate member may be fixed relative to an amount of rotation of the wheel.

The implant-free methods for treating conditions of the eye may include advancing an elongate member into Schlemm's canal, where the elongate member has been loaded with a volume of viscoelastic fluid, and delivering the viscoelastic fluid into Schlemm's canal at a volume sufficient to disrupt the trabeculocanalicular tissues to reduce intraocular pressure. However, the implant-free methods for treating conditions of the eye may not necessarily include delivery of viscoelastic fluids. In these instances, the method may comprise advancing an elongate member into Schlemm's canal, where the elongate member has a diameter between about 200 and about 500 microns, and where advancement, retraction, or removal of the elongate member into Schlemm's canal disrupts the trabeculocanalicular tissues sufficient to reduce intraocular pressure. In some instances, the method may comprise removing the system from the eye, and in doing so cutting or tearing through the trabecular meshwork with the body of the elongate member.

Other methods for treating conditions of the eye may be single-handed, single-operator methods for introducing viscoelastic fluid into Schlemm's canal that include advancing an elongate member into Schlemm's canal, where the elongate member has been loaded with a volume of viscoelastic fluid, and delivering the viscoelastic fluid into Schlemm's canal, where delivering the volume of viscoelastic fluid is accomplished by a single-handed system used by a single operator.

When viscoelastic fluids are delivered in the methods disclosed herein, the disruptive volume may be between about 2 μl (microliters) to about 16 μl (microliters), or between about 2 μl to about 8 μl. In some variations of the methods, the volume of fluid capable of disrupting trabeculocanalicular tissues is about 2 μl, about 3 μl, about 4 μl, about 5 μl, about 6 μl, about 7 μl, about 8 μl, about 9 μl, about 10 μl, about 11 μl, about 12 μl, 13 μl, about 14 μl, about 15 μl, or about 16 μl. It may be beneficial to deliver a volume of about 4 μl of viscoelastic fluid in certain instances. In yet further variations, the volume of fluid delivered ranges from about 1 μl per 360 degrees of the canal to about 50 μl per 360 degrees of the canal. In yet further variations, the volume of fluid delivered ranges from about 0.5 μl per 360 degrees of the canal to about 500 μl per 360 degrees of the canal. The viscoelastic fluid may be delivered while advancing the elongate member of a single-handed, single-operator controlled system from Schlemm's canal in the clockwise direction, counterclockwise direction, or both, and/or during withdrawal of the elongate member from Schlemm's canal. The volume of viscoelastic fluid delivered may be fixed relative to the distance traveled by the elongate member, and the viscoelastic fluid may be delivered to the same distance around Schlemm's canal as the elongate member is advanced around the canal. As previously stated, the viscoelastic fluid may be delivered to disrupt Schlemm's canal and surrounding trabeculocanalicular tissues. For example, the delivered viscoelastic fluid may cause disruption by dilating Schlemm's canal, increasing the porosity of the trabecular meshwork, stretching the trabecular meshwork, forming microtears or perforations in juxtacanalicular tissue, removing septae from Schlemm's canal, dilating collector channels, or a combination thereof. The elongate member may be loaded with the viscoelastic fluid at the start of an ocular procedure so that a single-operator can use a single hand to manipulate the system (e.g., advance and retract the elongate member or any associated tool) and deliver the fluid into the trabeculocanalicular tissues.

The methods disclosed herein may also include advancement of the elongate member about a 360 degree arc of Schlemm's canal, a 180 degree arc of Schlemm's canal, a 90 degree arc of Schlemm's canal, or other degree arc (e.g., between about a 5 degree arc and about a 360 degree arc). Advancement may occur from a single access point in Schlemm's canal or from multiple access points in the canal. The disclosed methods may also be used to treat a variety of eye conditions, including, but not limited to, glaucoma, pre-glaucoma, and ocular hypertension.

Methods for ab-interno trabeculotomy and goniotomy are also disclosed using the system and steps disclosed herein, including advancing a cannula at least partially through the anterior chamber of the eye, entering Schlemm's canal at a single access point using the cannula, and delivering a volume of a viscoelastic fluid through a lumen of an elongate member slidable within, and extendable from, the cannula, sufficient to disrupt the structure of Schlemm's canal and surrounding trabeculocanalicular tissues to reduce intraocular pressure. Another method that may be useful in treating conditions of the eye includes entering Schlemm's canal using an elongate member extendable from a single-operator controlled handle, the handle comprising a fluid reservoir, and delivering a volume of a viscoelastic fluid from the fluid reservoir through a lumen of the elongate member by increasing pressure within the fluid reservoir, where the volume of delivered viscoelastic fluid is sufficient to disrupt the structure of Schlemm's canal and surrounding tissues to reduce intraocular pressure. Other methods for ab-interno trabeculotomy and goniotomy may include cutting, tearing, and/or removing trabecular meshwork without the delivery of a viscoelastic fluid. In such methods, an elongate member configured to mechanically tear or cut and remove trabecular meshwork may be employed. In some methods, the elongate member is configured to mechanically tear or cut the trabecular meshwork when the delivery system is removed from the eye after advancing the elongate member into Schlemm's canal. In other methods, the elongate member may comprise a larger diameter, cutting features, and/or tool along or at the distal portion of the elongate member. For example, if the trabecular meshwork were being both cut and removed, the conduit might pull excised tissue back into the cannula during retraction.

The methods for treating conditions of the eye described here may comprise advancing an elongate member into Schlemm's canal and retracting the elongate member. The elongate member may comprise a lumen having a distal opening at a distal tip of the elongate member, and retracting the elongate member may include simultaneously delivering a fluid composition out of the distal opening of the lumen. In some variations, retracting the elongate member and delivering the fluid composition may both be actuated by rotation of a wheel. In some instances, the elongate member may be advanced a first length around Schlemm's canal and the fluid composition may be delivered the same first length around Schlemm's canal. In some of the methods described here, the elongate member may be advanced about 180 degrees around Schlemm's canal in a first direction. Some of these methods may further comprise advancing the elongate member about 180 degrees around Schlemm's canal in a second direction, and retracting the elongate member and simultaneously delivering a fluid composition out of the distal opening of the lumen.

In some variations, the methods described here for delivering a fluid composition into Schlemm's canal using a device comprising a reservoir, a plunger comprising a lumen and a proximal end, and a flexible elongate member comprising a lumen, with the reservoir fluidly connected to the lumen of the flexible elongate member via the lumen of the plunger and with the proximal end of the plunger located slidably within the reservoir, may comprise moving the proximal end of the plunger proximally within the reservoir from an extended position to a depressed position within the reservoir such that the plunger displaces fluid composition from the reservoir. The displaced fluid composition may travel through the lumen of the plunger to the lumen of the flexible elongate member.

In other variations, the methods described here for treating conditions of the eye using a delivery system comprising a housing, a drive mechanism comprising a first wheel having a portion extending out of a first side of the housing and a second wheel having a portion extending out of a second side of the housing, a cannula extending form a distal end of the housing, and a slidable elongate member located slidably within the cannula, may comprise piercing trabecular meshwork of the eye with the cannula, proximally moving the portion of the first wheel extending out of the first side of the housing to extend the slidable elongate member distally from a retracted position within the cannula such that it advances around Schlemm's canal in a first direction, and distally moving the portion of the first wheel extending out of the first side of the housing to retract the slidable elongate member proximally back to the retracted position. In some variations, distally moving the portion of the first wheel extending out of the first side of the housing may also cause a fluid composition to be delivered into Schlemm's canal. In some instances, the methods may further comprise proximally moving the portion of the second wheel extending out of the second side of the housing to extend the slidable elongate member distally from the retracted position within the cannula such that it advances around Schlemm's canal in a second direction, and distally moving the portion of the second wheel extending out of the second side of the housing to cause the slidable elongate member to retract proximally back to the retracted position. In some instances, distally moving the portion of the second wheel extending out of the second side of the housing may also cause a fluid composition to be delivered to Schlemm's canal.

Methods for disrupting trabecular meshwork of an eye using a device comprising a cannula, a flexible tool slidable within the cannula between a retracted position within the cannula and an extended position, and a drive assembly, may comprise advancing the cannula into an anterior chamber through a corneal or scleral incision, piercing the trabecular meshwork of the eye with the cannula, extending the flexible tool from the retracted position to the extended position, and retracting the cannula from the anterior chamber without retracting the flexible tool. The drive assembly may be configured to advance the flexible tool a first maximum distance without being retracted and may be configured to limit the cumulative advancement of the flexible tool to a maximum total distance. In some variations, the first maximum distance may be between 15 mm and 25 mm, and the maximum total distance may be between 35 mm and 45 mm.

In some variations, methods for disrupting trabecular meshwork of an eye using a device comprising a cannula, a flexible tool comprising a body and slidable within the cannula between a retracted position within the cannula and an extended position, may comprise advancing the cannula into an anterior chamber through a corneal or scleral incision, piercing the trabecular meshwork of the eye with a distal tip of the cannula, extending the flexible tool from the retracted position to the extended position, and tearing the trabecular meshwork with the body of the flexible tool progressively from a proximal end of the body to a distal end of the body.

The kits described here may comprise a first device and a second device. The first device may comprise a housing, a cannula, a flexible polymeric elongate member, a reservoir, and a drive assembly. The cannula may be attached to the distal end of the housing and may comprise a distal tip. The flexible polymeric elongate member may comprise a lumen and a distal end, and the distal end may be slidable within the cannula between a retracted position and an extended position. The distal end may be within the cannula in the retracted positioned and distal to the distal tip of the cannula in the extended position. The reservoir may comprise a fluid composition and the reservoir may be fluidly connected to the lumen of the flexible polymeric elongate member. The drive assembly may be configured to simultaneously move the flexible polymeric elongate member from the extended position to the retracted position and may deliver the fluid composition from the reservoir through the lumen of the flexible polymeric elongate member.

The second device may also comprise a housing, a cannula, a flexible polymeric elongate member, and a drive assembly. The cannula may be attached to the distal end of the housing and may comprise a distal tip. The flexible polymeric elongate member may comprise a lumen and a distal end. The distal end may be slidable within the cannula between a retracted position and an extended position and the distal end may be within the cannula in the retracted position and distal to the distal tip of the cannula in the extended position. The drive assembly may be configured to move the flexible polymeric elongate member from the extended position to the retracted position. The second device may not comprise a reservoir.

In some variations, the kits described here may comprise a device and a tray. The device may comprise a housing, a cannula, and a flexible polymeric elongate member. The cannula may be attached to the distal end of the housing and may comprise a distal tip. The flexible polymeric elongate member may comprise a lumen and a distal end, and the distal end may be slidable within the cannula between a retracted position and an extended position. The distal end may be within the cannula in the retracted position and distal to the distal tip of the cannula in the extended position. The tray may be configured to removably receive the device. The tray may comprise a first set of pinch points and a second set of pinch points and when the device is in the tray, the cannula may not contact the tray.

In some instances, the device may further comprise a drive assembly and the drive assembly may be configured to advance the flexible polymeric elongate member a first maximum distance without being retracted. The device may be configured to limit the cumulative advancement of the flexible polymeric elongate member to a maximum total distance. In some of these instances, the first maximum distance may be between 15 mm and 25 mm and the maximum total distance may be between 35 mm and 45 mm.

As described here are methods of manufacturing a cannula for accessing Schlemm's canal. The methods may comprise creating a bevel at a distal tip of the cannula, sharpening the cannula, and smoothing a portion of the cannula. The distal tip of the cannula may comprise inner and outer circumferential edges and the cannula may comprise a lumen therethrough. The bevel may traverse the lumen and creating the bevel may create proximal and distal ends of the distal tip. Sharpening the cannula may include sharpening the distal end of the distal tip of the cannula thereby creating a sharpened piercing tip. Smoothing a portion of the cannula may include smoothing a portion of the inner or outer circumferential edges. In some variations, the cannula may comprise stainless steel, Nitinol, or titanium hypodermic tubing.

In some variations, sharpening the distal end of the distal tip may comprise grinding a portion of an external surface of the cannula and/or a portion of the outer circumferential edge. In some variations, the sharpened piercing tip may be configured to pierce trabecular meshwork of an eye. In some instances, the sharpened piercing tip may comprise two angled surfaces. In some of these instances, an angle between the two angled surfaces may be between 50 degrees and 100 degrees.

In some instances, smoothing a portion of the inner or outer circumferential edges may comprise smoothing the inner circumferential edge at the proximal end of the distal tip. In some variations, smoothing a portion of the inner or outer circumferential edges may comprise smoothing the outer circumferential edge at the proximal end of the distal tip. In some instances, smoothing a portion of the inner or outer circumferential edges may comprise smoothing both the inner and outer circumferential edges at the proximal end of the distal tip. In some variations, smoothing a portion of the inner or outer circumferential edges may comprise smoothing the inner circumferential edge at the distal end of the distal tip. In some instances, smoothing a portion of the inner or outer circumferential edges may comprise smoothing the entire inner circumferential edge and smoothing the outer circumferential edges at the proximal end of the distal tip. In any of these variations or instances, smoothing may comprise abrasively blasting with a soda media.

In some variations, the methods of manufacturing may further comprise applying a protective covering to the sharpened piercing tip prior to the smoothing step. In these variations, the sharpened piercing tip may comprise angled surfaces and the angles surfaces may be covered by the protective covering.

In some instances, the methods of manufacturing may further comprise polishing the distal tip. In some of these instances, polishing may comprise electropolishing. In some variations, the methods may further comprise passivating the cannula. In some of these variations, passivating may remove iron oxide from the cannula. Additionally, in some of these variations, passivating may comprise passivating with acid. In some instances, the methods may further comprise roughening at least a portion of the cannula proximal to the distal tip. In some of these instances, roughening may comprise abrasively blasting with a soda media.

In variations of the methods of manufacturing described here the methods may further comprise cutting the cannula to a length between 50 mm and 70 mm. In some of these variations, cutting the cannula may comprise cutting the cannula to a length of 60 mm.

In some instances, the methods of manufacturing may further comprise bending a distal portion of the cannula along a longitudinal axis of the cannula. In some of these instances, bending a distal portion of the cannula may comprise bending the distal portion to an angle between 100 degrees and 125 degrees. In some of these instances, bending the distal portion of the cannula may comprise bending the distal portion to a 118 degree angle.

In some variations, the methods of manufacturing a cannula for accessing Schlemm's canal may comprise cutting a cannula to a working length, roughening an outer surface of the cannula, creating a bevel at a distal tip of the cannula, grinding the distal end of the distal tip, applying a protective covering, smoothing a portion of the cannula, bending the cannula, electropolishing the cannula, and passivating the cannula. In some variations, the cannula may comprise a proximal portion, a central portion, a distal portion, and a lumen therethrough and the distal portion may comprise a distal tip. In some instances, toughening an outer surface of the cannula may include roughening an outer surface of the central portion of the cannula. In some variations, the distal tip of the cannula may comprise inner and outer circumferential edges, and the cannula may comprise a lumen therethrough. In some instances, the bevel may traverse the lumen and creating the bevel may create proximal and distal ends of the distal tip. In some variations, grinding the distal end of the distal tip may thereby further sharpen the distal end of the distal tip to create a sharpened piercing tip. In some instances, applying a protective covering may include applying a protective covering to the sharpened piercing tip and smoothing a portion of the cannula may include smoothing a portion of the inner or outer circumferential edge. In some variations, bending the cannula may include bending the distal portion of the cannula along a longitudinal axis of the cannula and electropolishing the cannula may include electropolishing the distal tip. In some instances, passivating the cannula may include passivating the cannula with acid.

BRIEF DESCRIPTION OF THE DRAWINGS

FIGS. 4A-4B depict perspective views of an exemplary drive assembly. FIG. 4A shows the drive assembly in the handle of the system in a first orientation and FIG. 4B shows the handle in a second, flipped orientation.

FIGS. 10A-10B show an exemplary delivery system for delivering a fluid composition into Schlemm's canal. FIG. 10A is a perspective view of the system. FIG. 10B is a partial cross-sectional view of the system.

FIGS. 11A-11C illustrate an exemplary method of delivering a fluid composition out of the delivery system.

FIG. 14 is a stylized depiction of an ab-interno method for accessing Schlemm's canal with the cannula of an exemplary delivery system.

DETAILED DESCRIPTION

Described here are systems and methods for accessing Schlemm's canal and for delivering an ocular device, tool, and/or fluid composition therein to reduce intraocular pressure and thereby treat conditions of the eye. The fluids and certain components of the system, e.g., the slidable elongate member, may be used to provide a force for disrupting trabeculocanalicular tissues, which include the trabecular meshwork, juxtacanalicular tissue, Schlemm's canal, and the collector channels. As used herein, the term "disrupting" refers to the delivery of a volume of fluid or a system component that alters the tissue in a manner that improves flow through the trabeculocanalicular outflow pathway. Examples of tissue disruption include, but are not limited to, dilation of Schlemm's canal, dilation of collector channels, increasing the porosity of the trabecular meshwork, stretching the trabecular meshwork, forming microtears or perforations in juxtacanalicular tissue, removing septae from Schlemm's canal, cutting, tearing, or removal of trabeculocanalicular tissues, or a combination thereof.

Figure 1:
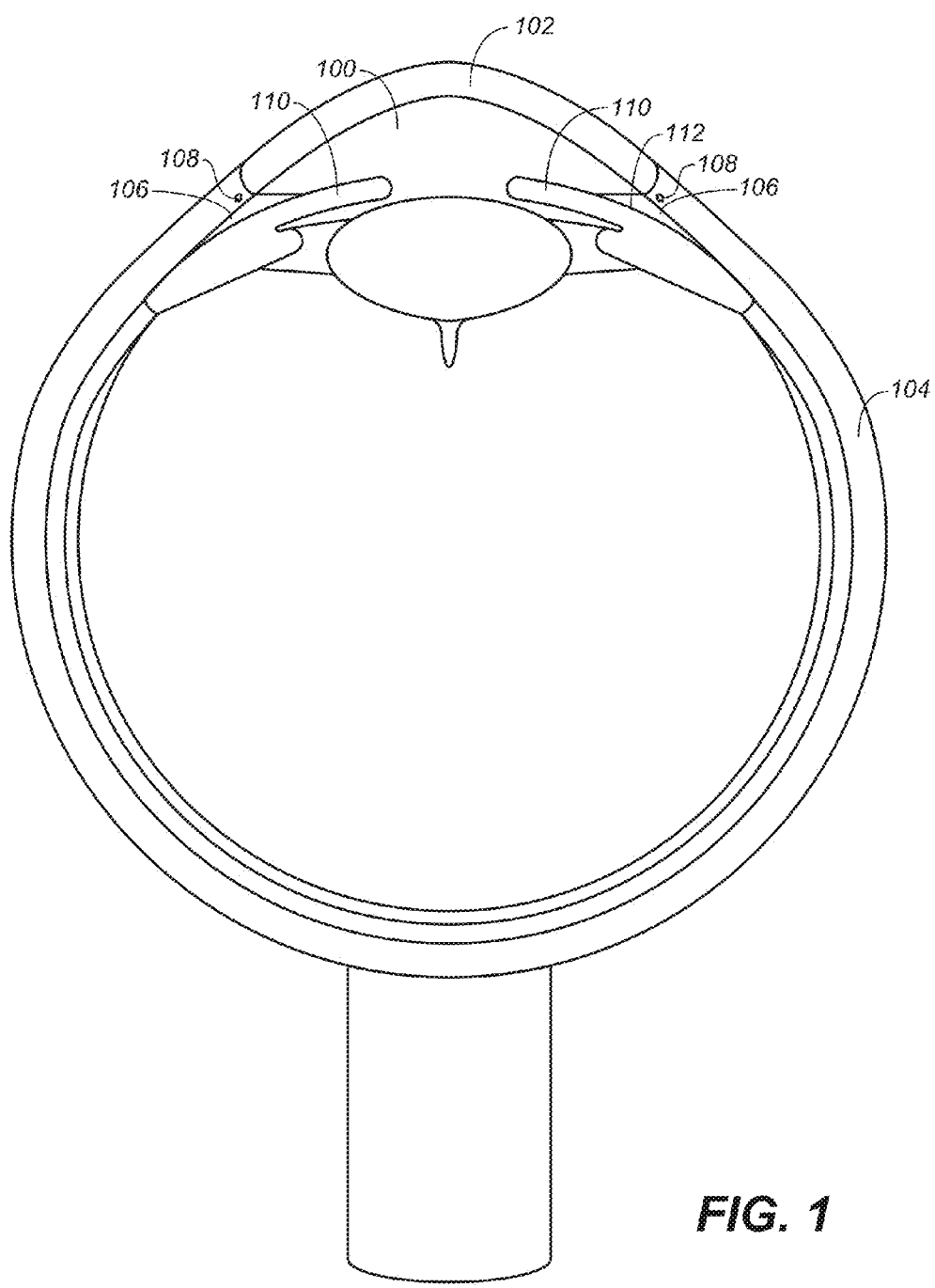
FIG. 1 shows a stylized, cross-sectional view of the eye and some of the structures involved in the flow of aqueous humor out of the eye.

To better understand the systems and methods described here, it may be useful to explain some of the basic eye anatomy. FIG. 1 is a stylized depiction of a normal human eye. The anterior chamber (100) is shown as bounded on its anterior surface by the cornea (102). The cornea (102) is connected on its periphery to the sclera (104), which is a tough fibrous tissue forming the protective white shell of the eye. Trabecular meshwork (106) is located on the outer periphery of the anterior chamber (100). The trabecular meshwork (106) extends 360 degrees circumferentially around the anterior chamber (100). Located on the outer peripheral surface of the trabecular meshwork (106) is Schlemm's canal (108). Schlemm's canal (108) extends 360 degrees circumferentially around the meshwork (106). At the apex formed between the iris (110), meshwork (106), and sclera (104), is the anterior chamber angle (112).

The systems are generally configured for single-handed manipulation and for control by a single operator, and include one or more features useful for easily accessing Schlemm's canal with minimal trauma. Once access to the canal has been obtained, the system may deliver an ocular device, a tool, and/or a fluid composition. In some variations, the system advances a tool that disrupts Schlemm's canal and surrounding tissues without delivery of an ocular device or a fluid composition. For example, the tool may be an elongate member, slidable within, and extendable from, the cannula used to access the canal, having an outer diameter sized to disrupt the canal and surrounding tissues. The body of the elongate member may be in some instances configured to cut or tear through the trabecular meshwork if the system is removed from the eye while the elongate member is within Schlemm's canal, and/or the distal end of the elongate member may be provided with a disruptive component to aid in the disruption of trabeculocanalicular tissues.

When a device is implanted into the canal, it will generally be configured to maintain the patency of Schlemm's canal without substantially interfering with transmural fluid flow across the canal. This may restore, enable, or enhance normal physiologic efflux of aqueous humor through the trabeculocanalicular tissues. Ocular implants such as those disclosed in U.S. Pat. No. 7,909,789, and such as those disclosed in U.S. Pat. No. 8,529,622, each of which is hereby incorporated by reference in its entirety, may be delivered. In some variations, the implants in U.S. Pat. Nos. 7,909,789 and 8,529,622 include a support having a least one fenestration that completely traverses a central core of Schlemm's canal without substantially interfering with transmural fluid flow or longitudinal fluid flow across or along the canal. The ocular device may also disrupt the juxtacanalicular trabecular meshwork or adjacent inner wall of Schlemm's canal. The ocular devices may also be coated with a drug useful for treating ocular hypertension, glaucoma, or pre-glaucoma, infection, or scarring, neovascularization, fibrosis, or inflammation postoperatively. The ocular device may also be formed to be solid, semi-solid, or bioabsorbable.

The systems may also be used to deliver a fluid composition, e.g., saline or a viscoelastic fluid. The saline may be used for irrigation. The viscoelastic fluid may be employed in ab-interno versions of viscocanalostomy or canaloplasty procedures to disrupt the canal and surrounding tissues.

I. Systems/Devices

The systems described herein may be single-handed, single-operator controlled devices that generally include a universal handle having a grip portion and a housing that has an interior and a distal end. A cannula is typically coupled to and extends from the housing distal end. The cannula may include a proximal end and a distal curved portion, where the distal curved portion has a proximal end and a distal end, and a radius of curvature defined between the ends. In other variations, the cannula may be straight and may not comprise a distal curved portion. The cannula may also be configured to include a body; a distal tip having a bevel; and a lumen extending from the proximal end through the distal tip. The bevel may directly engage the distal end of the curved portion of the cannula (i.e., the bevel may directly engage the radius of curvature). The systems may also generally include a drive assembly partially contained within the housing comprising gears that translate rotational movement to linear movement. When an ocular device is to be implanted into Schlemm's canal, the systems may further include a slidable positioning element having a proximal end and a distal end that is coaxially disposed within the cannula lumen. The system may also be configured to include a slidable elongate member comprising a lumen that is coaxially disposed within the cannula lumen. When a fluid composition is to be delivered into Schlemm's canal, the system may also be configured to include a fluid assembly in the handle. Fluid compositions such as saline, viscoelastic fluids, including viscoelastic solutions, air, and gas may be delivered using the system. Suitable markings, colorings, or indicators may be included on any portion of the system to help identify the location or position of the distal end of the cannula, the positioning element, the engagement mechanism, the ocular device, or the slidable elongate member. In some instances, the systems described herein may be used to perform ab-interno trabeculotomy, ab-interno transluminal trabeculotomy, clear corneal trabeculotomy, clear corneal transluminal trabeculotomy, ab-interno canaloplasty, and/or clear corneal canaloplasty, and may be used to deliver a fluid composition into the anterior or posterior segment of the eye.

Figure 2:
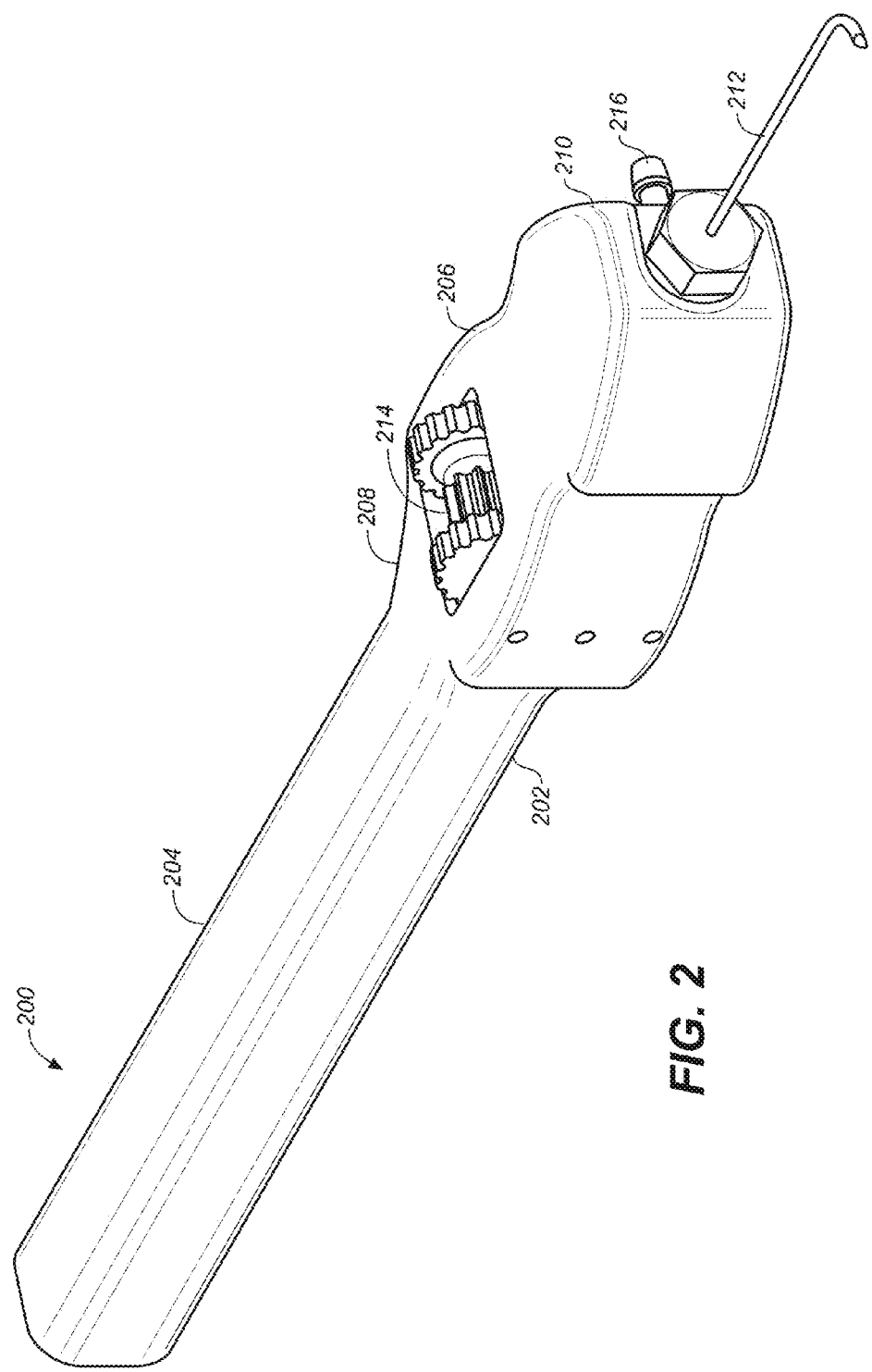
FIG. 2 depicts a perspective view of an exemplary delivery system for implanting an ocular device.

An exemplary ocular delivery system is depicted in FIG. 2. In the figure, delivery system (200) includes a universal handle (202) having a grip portion (204) and a housing (206). The housing has a proximal end (208) and a distal end (210). A cannula (212) is coupled to and extends from the housing distal end (210). A drive assembly (214) is substantially contained within the housing (206) that actuates movement of a positioning element (not shown). Port (216) is provided on the distal end of the housing (210) for removable connection to a source of irrigation fluid.

The delivery systems described herein may in some variations be fully disposable. In other variations, a portion of the delivery system may be reusable (e.g., non-patient contact materials, such as the handle), while a portion of the delivery system may be disposable (e.g., patient-contact materials, such as the cannula and elongate member). In yet other variations, the delivery systems described herein may be fully reusable.

Universal Handle

The ocular delivery systems described herein may include a universal handle capable of single-handed use. For example, the handle may be configured to be capable for use with the left or right hand, for use on the left or right eye, or in the clockwise or counterclockwise direction. That is, the handle may be configured such that the ability to use the delivery system is independent of which hand is used, which eye a procedure is performed on, or which direction around the canal an ocular device, tool, or fluid composition is delivered. For example, the delivery system may be used to deliver an ocular device, elongate member, and/or fluid composition in a clockwise direction in an eye, and then with a simple flip of the handle (or by rotating the cannula itself 180 degrees in another variation) to a second orientation, may be used to deliver an ocular device, elongate member, and/or fluid composition in the counterclockwise direction. However, it should be appreciated that in other variations, the delivery systems described herein may be configured to be used in a particular configuration (e.g., with a single side up, only in a clockwise direction, only in a counterclockwise direction, etc.). The handle generally includes a grip portion and a housing. The grip portion may be raised, depressed, or grooved in certain areas, or textured to improve hold of the handle by the user or to improve comfort of the user. The housing may include an interior portion and a distal end. The interior portion of the housing may contain a drive assembly and a positioning element (both further described below). In some variations, the distal end of the housing includes a fluid port that can provide fluids for irrigation of the operative field or to purge air from the system.

The universal handle may be made from any suitable material, including without limitation, fluoropolymers; thermoplastics such as polyetheretherketone, polyethylene, polyethylene terephthalate, polyurethane, nylon, and the like; and silicone. In some variations, the housing or portions thereof may be made from transparent materials. Materials with suitable transparency are typically polymers such as acrylic copolymers, acrylonitrile butadiene styrene (ABS), polycarbonate, polystyrene, polyvinyl chloride (PVC), polyethylene terephthalate glycol (PETG), and styrene acrylonitrile (SAN). Acrylic copolymers that may be particular useful include, but are not limited to, polymethyl methacrylate (PMMA) copolymer and styrene methyl methacrylate (SMMA) copolymer (e.g., Zylar 631® acrylic copolymer). In variations in which the universal handle is reusable, the handle may be made from a material that can be sterilized (e.g., via autoclaving), such as a heat-resistant metal (e.g., stainless steel, aluminum, titanium).

The length of the universal handle may generally be between about 1 inch (2.5 cm) to about 20 inches (50.8 cm). In some variations, the length of the universal handle may be between about 4 inches (10.2 cm) and 10 inches (25.4 cm). In some variations, the length of the universal handle is about 7 inches (17.8 cm).

Cannula

The cannula of the ocular delivery system is typically coupled to and extends from the housing distal end, and is generally configured to provide easy and minimally traumatic access to Schlemm's canal using a minimally invasive ab-interno approach. The cannula may be fixedly attached to the distal end of the housing, or in other variations it may be rotatably attached to the distal end of the housing. In variations of the delivery systems where the handle is reusable and the cannula is disposable, the cannula may be removably attached to the distal end of the housing. Some variations of the cannula may include a proximal end and a distal curved portion, where the distal curved portion has a proximal end and a distal end, and a radius of curvature defined between the ends. However, it should be appreciated that in other variations the cannula may be straight and may not comprise a distal curved portion. The cannula may also be configured to include a body; a distal tip having a bevel and a sharpened piercing tip; and a lumen extending from the proximal end through the distal tip. When the cannula comprises a distal curved portion, the bevel may directly engage the distal end of the curved portion of the cannula (i.e., the bevel may directly engage the radius of curvature). In some variations, the sharpened piercing tip may comprise one or more angled surfaces, as is described in more detail below.

The cannula may be made from any suitable material with sufficient stiffness to allow it to be advanced through the eye wall and anterior chamber. For example, the cannula may be formed of a metal such as stainless steel, nickel, titanium, aluminum, or alloys thereof (e.g., Nitinol metal alloy), a polymer, or a composite. Exemplary polymers include without limitation, polycarbonate, polyetheretherketone (PEEK), polyethylene, polypropylene, polyimide, polyamide, polysulfone, polyether block amide (PEBAX), and fluoropolymers. In some instances, it may be advantageous to coat the cannula with a lubricious polymer to reduce friction between the ocular tissue and the cannula during the procedure. Lubricious polymers are well known in the art, and include, without limitation, polyvinyl alcohol, polyethylene glycol, polyvinyl pyrrolidone, fluorinated polymers (including polytetrafluoroethylene (PTFE or Teflon®)), and polyethylene oxide. In variations in which the cannula is reusable, the cannula may be made from a material that can be sterilized (e.g., via autoclaving), such as a heat-resistant metal (e.g., stainless steel, aluminum, titanium).

The cannula generally has an outer diameter sized to gain access to the lumen of Schlemm's canal while minimally obstructing the surgeon's view. Accordingly, the outer diameter may range from about 50 microns to about 1000 microns. In some variations, the outer diameter may range from about 150 microns to about 800 microns. The cannula also has an inner diameter, which may range from about 50 microns to about 400 microns. The cannula may also be formed to have any suitable cross-sectional profile, e.g., circular, elliptical, triangular, square, rectangular, etc.

The cannula may be configured to include multiple portions or parts. A cannula having a body, a distal curved portion having a proximal end and a distal end, a radius of curvature defined between the ends, and a bevel at the distal tip of the cannula that directly engages the distal end of the curved portion of the cannula may be particularly useful for accessing the lumen of Schlemm's canal. Here the body (straight portion of the cannula) may have a length ranging from about 5 mm to about 50 mm, about 10 mm to about 30 mm, or from about 14 mm to about 20 mm. In some variations, the body may have a length of about 18 mm. The distal curved portion of the cannula may be uniform in cross-sectional shape or it may taper closer to the distal end to facilitate entry into Schlemm's canal. The radius of curvature of the distal curved portion may be adapted to facilitate tangential entry, as well as precise and minimally traumatic entry into Schlemm's canal, and may range from about 1 mm to about 10 mm or from about 2 mm to about 5 mm. In one variation, the radius of curvature is about 2.5 mm. The cannula may also have an angular span suitable for facilitating entry into Schlemm's canal, and may range from about 70 degrees to about 170 degrees, or about 100 degrees to about 150 degrees. In one variation, the angular span is about 120 degrees.

The size, shape, geometry, and the like, of the bevel at the distal end of the curved portion of the cannula may be beneficial in allowing easy and minimally traumatic access to Schlemm's canal. In this respect, and as described in further detail below, having a bevel that directly engages the radius of curvature of the distal end of the cannula may be particularly useful.

In other variations, the cannula may include a short straight segment coupled to the distal end of the distal curved portion of the cannula (e.g., at the end of the radius of curvature). Here the bevel engages the straight segment and not the radius of curvature. The length of the straight segment may range from about 0.5 mm to about 5 mm. In some variations, the length of the straight segment ranges from about 0.5 mm to about 3 mm, or from about 0.5 mm to about 1 mm. The length of the straight segment may also be less than about 0.5 mm, e.g., it may be about 0.1 mm, about 0.2 mm, about 0.3 mm, or about 0.4 mm. In variations where the bevel directly engages the distal end of the curved portion of the cannula (i.e., the bevel directly engages the radius of curvature), the cannula lacks a straight segment (length of the straight segment is zero).

It may also be useful to have a bevel that is sharp and short to minimize the distance that any ocular device will have to travel when being implanted into the canal. Exemplary bevel angles may range from about 10 degrees to about 90 degrees. In some instances, the bevel angle may range from about 10 degrees to about 50 degrees. In one variation, the bevel angle is about 35 degrees, while in another variation the bevel is about 25 degrees. The bevel may also be oriented in any suitable direction. For example, the bevel may be oriented so that it opens up towards the surgeon, or it may be reversed to open away from the surgeon or in any plane in between.

Figure 15:
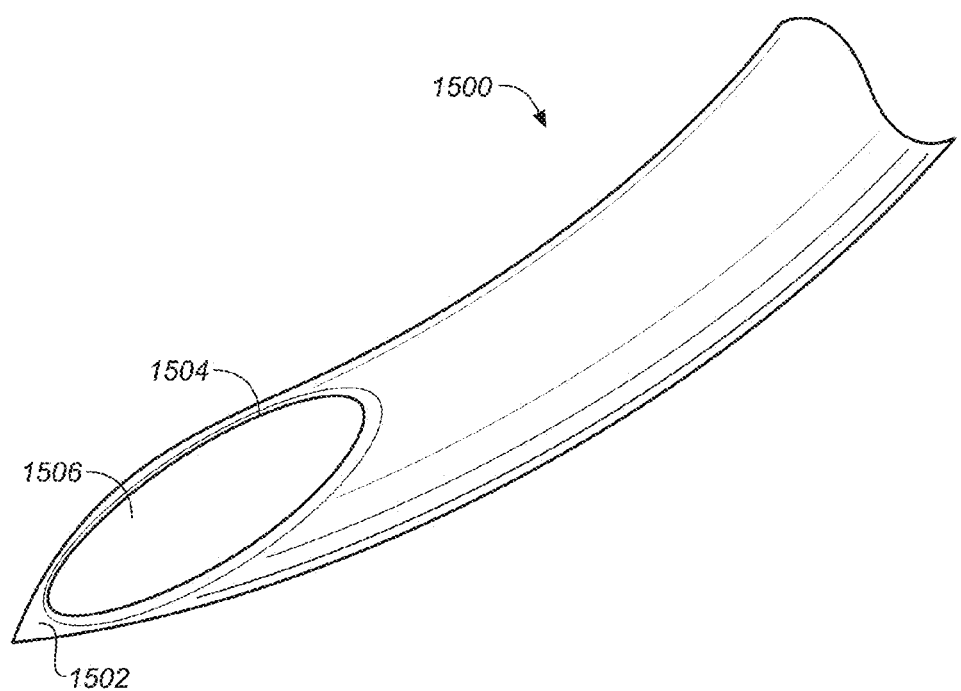
FIG. 15 depicts an exemplary cannula according to another variation.

As is described in more detail below, in yet some variations, the cannula is configured to include one section that is sharp, and another section that is blunt (e.g., deburred). The dual surface configuration of such a cannula may be advantageous, since it may provide easier canal access by piercing the meshwork while also providing a gentle, dispersed force on the elongate member during elongate member retraction into the cannula to avoid cutting or breaking the elongate member due to retraction force. For example, as shown in FIG. 15, the distal end of cannula (1500) may have a sharpened piercing tip (1502) and a smooth edge (1504) that define portions of opening (1506), through which a slidable elongate member (not shown) may be advanced and retracted. As is described in more detail with respect to FIGS. 19, 20A-20B, and 21, the sharp tip (1502) may be formed by compounding multiple bevels, and the smooth edge (1504) may be created by smoothing or deburring inner and/or outer circumferential edges of the distal tip. Additionally, in some embodiments, the internal and/or external surfaces of the elongate member adjacent to the opening (1506) may also be smoothed. Methods of making the cannula are described in more detail below.

Figure 3:
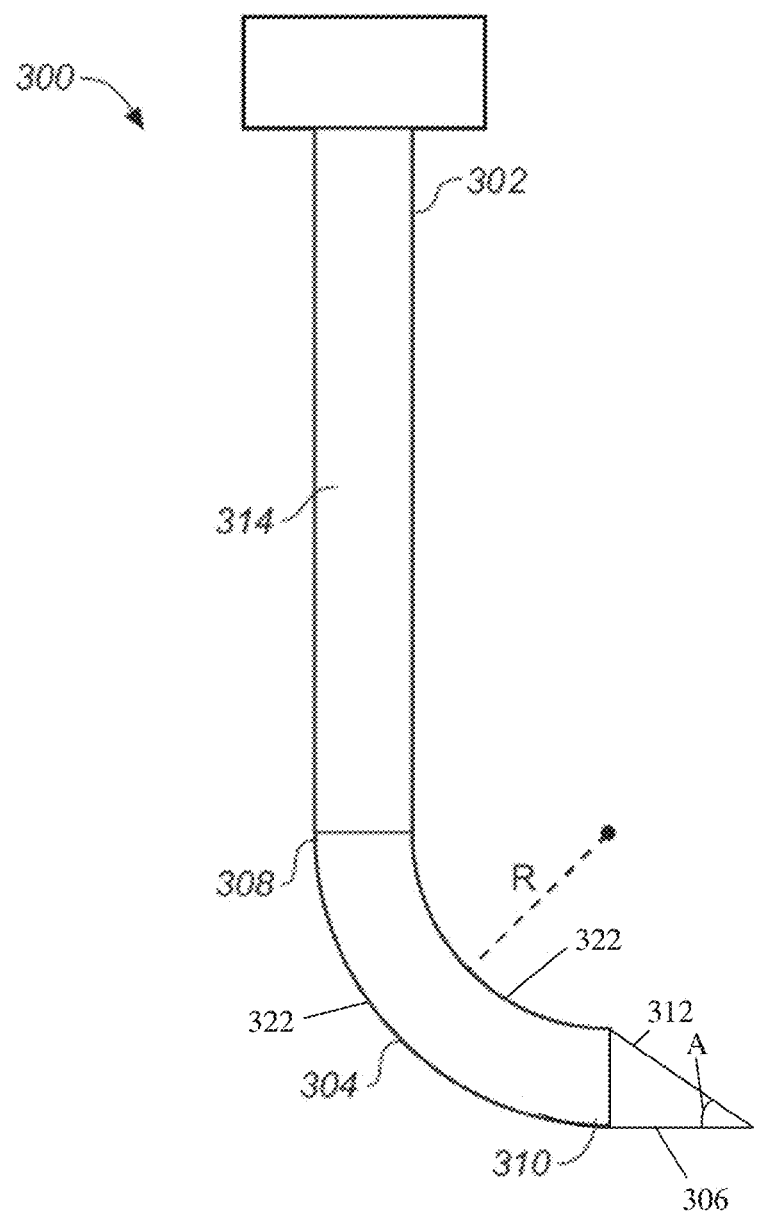
FIG. 3 depicts a side view of an exemplary cannula of the delivery system.

The cannula of an exemplary delivery system is shown in more detail in FIG. 3. Here the cannula (300) comprises a proximal end (302) a distal curved portion (304), a body (314), and a distal tip (306). The distal curved portion (304) has a proximal end (308) and a distal end (310), and a radius of curvature (R) that is defined between the ends (308, 310). The distal curved portion (304) also has an inner radius (320) defined by the surface of the cannula closest to the center of the radius of curvature (R), and an outer radius (322) defined by the surface of cannula further away from the center. A bevel (312) at the distal tip (306) directly engages the distal end of the curved portion of the cannula (310). In other words, the bevel (312) may be contiguous with the distal end of the curved portion of the cannula (310). As previously stated, this configuration of the distal curved portion (304) and bevel (312) may be beneficial or advantageous for allowing easy, atraumatic, and controlled access into Schlemm's canal. The angle of the bevel may also be important. In general, a short bevel may be beneficial. The bevel (312) may comprise an angle (A) between about 5 degrees and about 85 degrees. In some variations, the angle (A) may be about 5, 10, 15, 20, 25, 30, 35, 40, 45, 50, 55, 60, 65, 70, 75, 80, or 85 degrees. In some variations, the angle (A) may be between about 23 degrees and about 27 degrees. In the variation shown in FIG. 3, the bevel angle (A) is about 25 degrees.

Figure 20:
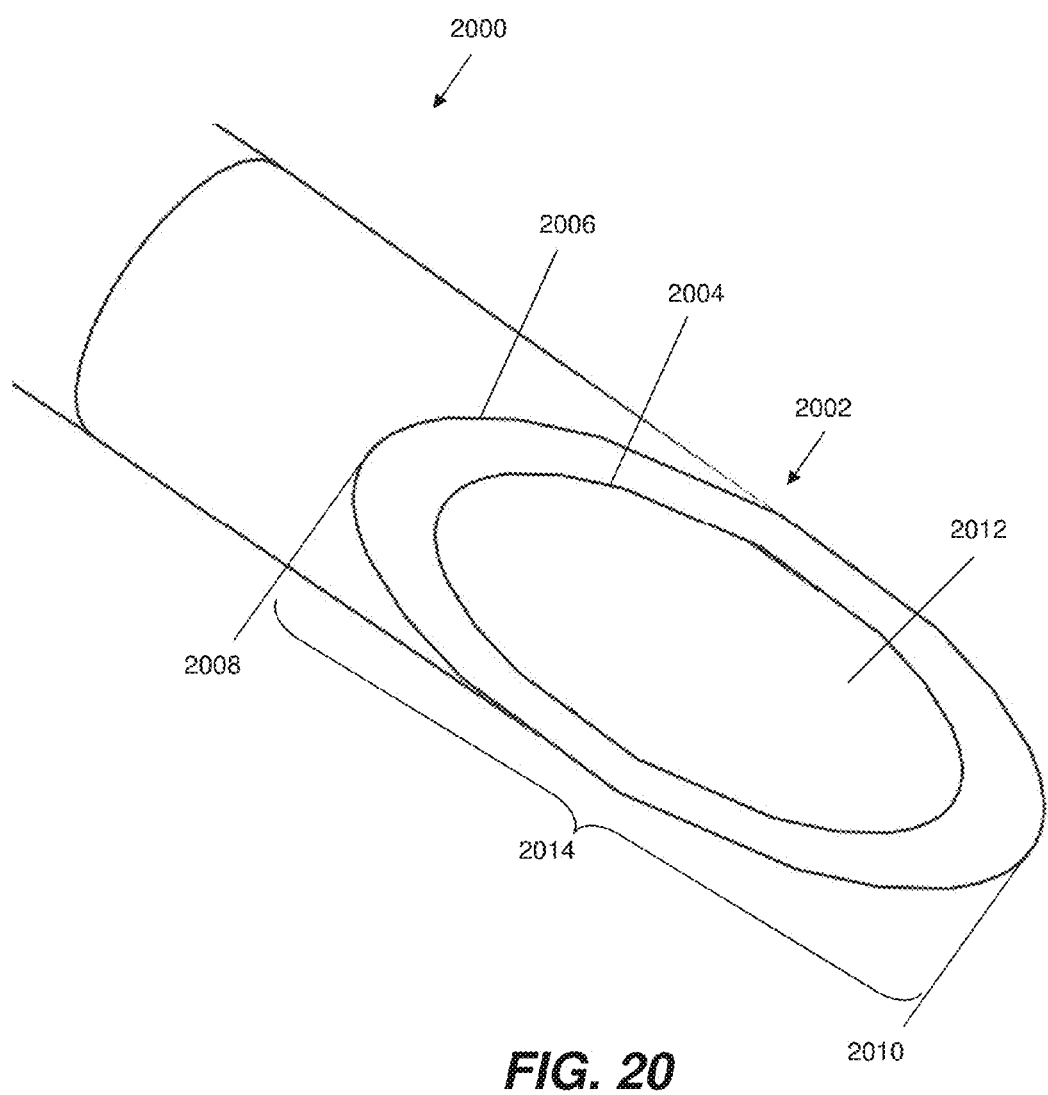
FIG. 20 is a perspective view of a variation of a distal tip of a cannula.

FIG. 20 depicts a perspective view of a distal tip (2002) of a cannula (2000) comprising a bevel (2014). The distal tip (2002) may be cut or ground at an angle to create the bevel (2014). As shown, the beveled distal tip (2002) comprises a proximal end (2008), a distal end (2010), and an elongated opening (2012) having an elliptical, rather than a circular, shape. The distal tip (2002) may comprise an elliptical shaped lumen opening that is angled such that the top of the elliptical opening is closer to the proximal portion of the cannula than the bottom of the elliptical opening. Also shown in FIG. 20 are inner and outer circumferential edges (2004, 2006).

Figure 21A:
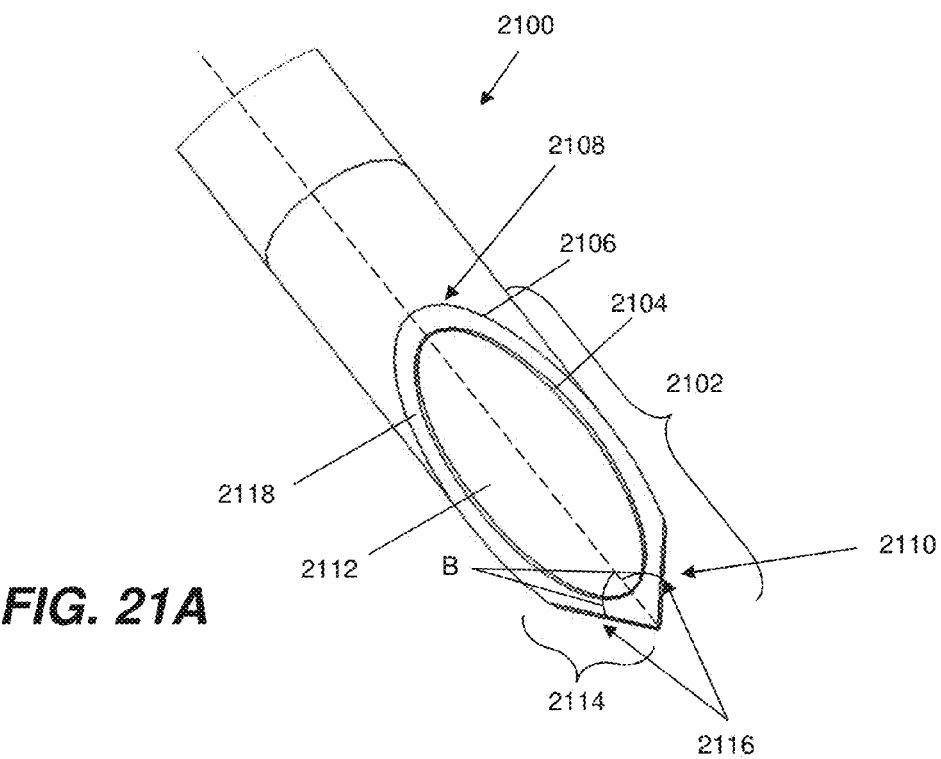
FIGS. 21A and 21B are perspective and front views, respectively, of a variation of a distal tip of a cannula.
Figure 21B:
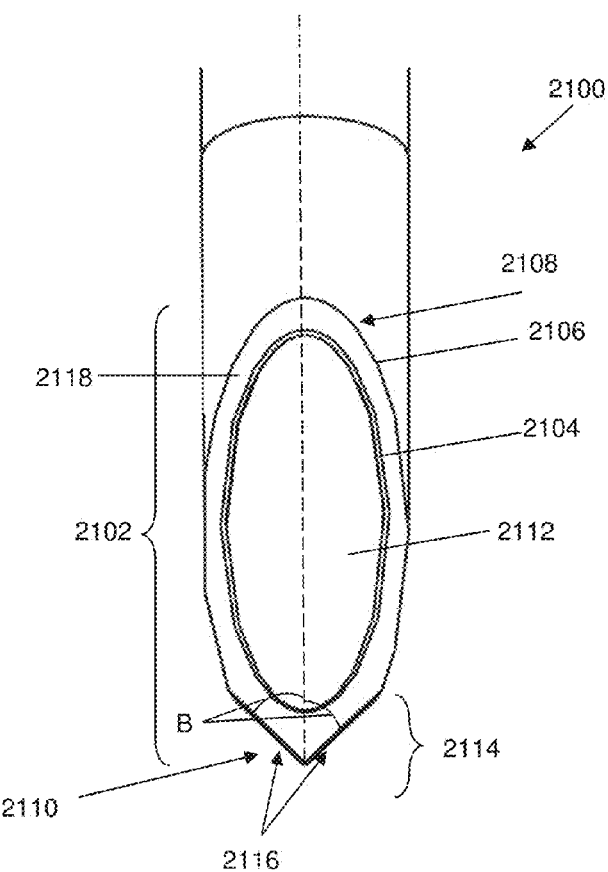

FIGS. 21A and 21B depict perspective and front views, respectively, of a variation of a distal tip (2100) of a cannula comprising a bevel (2102) and a sharpened piercing tip (2114). As shown there, the distal tip (2100) also comprises a proximal end (2108), a distal end (2110), inner and outer circumferential edges (2104, 2106), and a lumen opening (2112). The sharpened piercing tip (2114) may comprise two angled surfaces (2116) that converge to form a sharp point. The angled surfaces (2116) may have any suitable angle that results in a sharpened piercing tip (2114). For example, in some instances, the angle surfaces (2116) may have an angle (B) relative to the longitudinal axis of the distal tip (2100) of about 20, 25, 30, 35, 40, 45, or 50 degrees, between about 25 and about 50 degrees, or between about 37.5 and about 42.5 degrees. In some instances, the angle (B) may be about 40 degrees. Accordingly, in some variations, the angle between the two angled surfaces (2116) may be between about 50 and about 100 degrees, and in some instances, the angle between the two angled surfaces (2116) may be about 80 degrees. It should be appreciated that although the distal tip (2100) is depicted with two angled surfaces, a distal tip with a single angled surface may also be used.

Elongate Member

The delivery systems described herein may comprise a slidable elongate member coaxially disposed within the cannula lumen. The elongate member employed with the systems described herein may be of various configurations, and may or may not comprise a lumen. The elongate member may or may not be configured to deliver a fluid composition.

The elongate member may be coaxially disposed and slidable within the cannula lumen of the delivery systems described here. When the elongate member is in a retracted position relative to the cannula, the distal end of the elongate member may be located within (i.e., proximal to) the distal tip of the cannula. When the elongate member is in an extended position relative to the cannula, the distal end of the elongate member may be located outside of (i.e., distal to) the distal tip of the cannula. The length of extension of the elongate member beyond the distal tip of the cannula may correspond to the distance around Schlemm's canal that may be traversed by the elongate member (e.g., in order to disrupt Schlemm's canal and/or surrounding trabeculocanalicular tissues, and/or to deliver a fluid composition). In variations in which the delivery system is configured to deliver a fluid composition, the length traversed by the elongate member may correspond to the length around Schlemm's canal to which the fluid composition is delivered. In variations in which the delivery system is configured to tear or cut the trabecular meshwork, the length traversed by the elongate member may correspond to the length of trabecular meshwork that is cut or torn. In some variations, this length may be between about 1 mm and about 50 mm. In some of these variations, the length may be between about 10 mm and about 40 mm, between about 15 mm and about 25 mm, between about 16 mm and about 20 mm, between about 18 mm and about 20 mm, between about 19 mm and about 20 mm, between about 18 mm and about 22 mm, about 20 mm, between about 30 mm and about 50 mm, between about 35 mm and about 45 mm, between about 38 mm and about 40 mm, between about 39 mm and about 40 mm, or about 40 mm. The elongate member may be moved between extended and retracted positions using a drive assembly of the delivery system, described in more detail below.

The elongate member may be sized so that it can be advanced through the cannula and into a portion of Schlemm's canal (e.g., 0 to 360 degrees of the canal) to disrupt trabeculocanalicular tissues, stent, and/or apply tension to the canal, and/or to deliver a fluid composition. The elongate member may be made from any suitable material that imparts the desired flexibility and pushability for introduction through the eye wall, accessing Schlemm's canal, and/or navigation through other ocular tissue structures. For example, the elongate member may comprise a polymer (e.g., nylon, polypropylene); a polymer reinforced with metal wire, braid or coil; composites of polymers and metal; or metals such as stainless steel, titanium, shape-memory alloy (e.g., Nitinol), or alloys thereof. In variations in which the elongate member is reusable, the elongate member may be made from a material that can be sterilized (e.g., via autoclaving), such as a heat resistant metal (e.g., stainless steel, aluminum, titanium). The elongate member may be straight with enough flexibility and pushability to navigate the ring-shaped Schlemm's canal or may be pre-shaped to about a 2-10 mm radius of curvature or about a 6 mm radius of curvature (i.e., the approximate radius of curvature of Schlemm's canal in an adult human) to more easily circumnavigate Schlemm's canal, partially or in its entirety. In some variations, the elongate member may be configured to be advanced over or along a guidewire.

It may in some variations be desirable for the elongate member to have one or more features to improve visualization of the elongate member. For example, the elongate member may be colored (e.g., red, orange, yellow, green, blue, purple, etc.). Additionally or alternatively, visualization may be improved using an illuminated beacon, a fiber optic, side illuminating fiber optic, luminescence, fluorescence, or the like. For example, a fiber optic may travel along the body of the elongate member to deliver light to the distal tip of the elongate member, which may improve visualization of the distal tip of the elongate member as it is advanced or retracted about Schlemm's canal.

In some variations, the elongate member may be sized to have an outer diameter sufficient to disrupt Schlemm's canal and surrounding trabeculocanalicular tissues. The outer diameter may range from about 25 microns to about 1000 microns, from about 25 microns to about 500 microns, from about 50 microns to about 500 microns, from about 150 microns to about 500 microns, from about 200 microns to about 500 microns, from about 300 microns to about 500 microns, from about 200 microns to about 250 microns, from about 150 microns to about 200 microns, or from about 180 microns to about 300 microns. In some instances it may be beneficial for the elongate member to have an outer diameter of about 240 microns.

In some variations, the distal end of the elongate member may be configured as a blunt bevel, an atraumatic tip, an enlarged atraumatic tip, or the like, to help the elongate member be advanced through Schlemm's canal. In some of these variations, the distal end may comprise a blunt parasol-shaped atraumatic tip. In other variations, a distal portion of the elongate member may optionally include a disruptive component, e.g., a notch, hook, barb, a rough surface, or combination thereof, to disrupt the juxtatrabecular portion of Schlemm's canal or juxtatrabecular meshwork. One or more projections emanating from the elongate member may further disrupt the juxtatrabecular portion of Schlemm's canal or juxtatrabecular meshwork and thus increase permeability of aqueous humor through the trabecular meshwork into Schlemm's canal. In some instances, the elongate member may also deliver energy to the trabeculocanalicular tissues (e.g., ultrasonic energy, radiofrequency energy (e.g., for electrocautery, electroablation), electromagnetic radiation, light energy (e.g., via a fiber optic)).

In some instances, the elongate member may comprise a filament (e.g., a filament comprising nylon, polypropylene, metal, or the like). For example, the elongate member may comprise a nylon monofilament. An exemplary range of filament size may range from about 50 microns to about 300 microns. The filament may be configured to be advanced through all or a portion of Schlemm's canal. In some instances the body of the filament may be configured to cut or tear through the trabecular meshwork when the cannula is removed from the eye. In other instances the filament may be configured to disrupt trabeculocanalicular tissue upon advancement into or retraction from Schlemm's canal. In yet other instances the filament may be configured to be left within the canal to continuously deliver tension on the meshwork and maintain patency of the canal.

Figure 12:
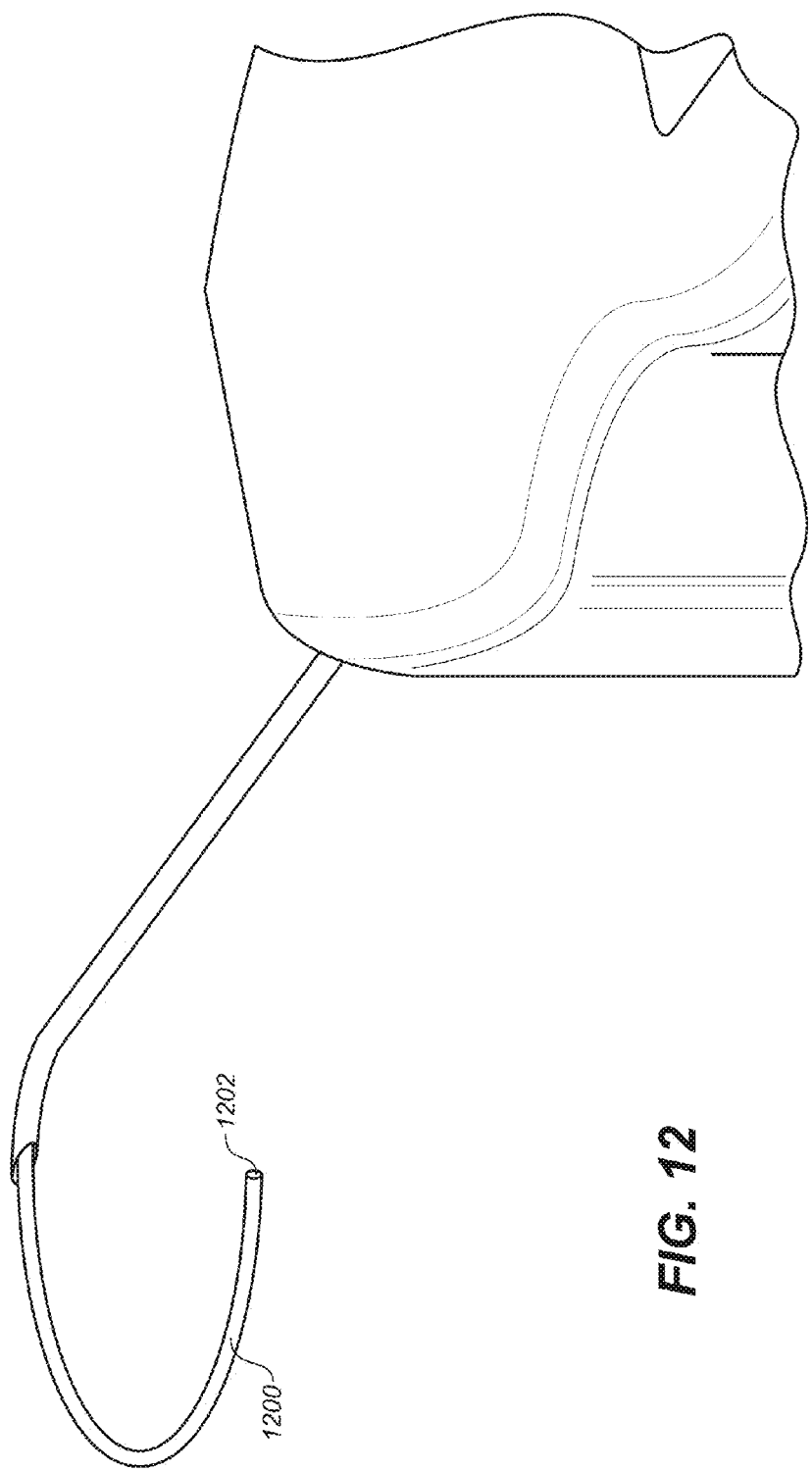
FIG. 12 depicts an exemplary slidable elongate member for delivering a fluid composition.

In some variations the elongate member may comprise a lumen. For example, in one variation the elongate member may comprise a microcatheter (e.g., a nylon microcatheter). In some of the instances in which the elongate member comprises a lumen, the elongate member may be configured to deliver a fluid composition. The fluid composition may travel through a lumen of the elongate member and may be delivered through an opening of the lumen. For example, as shown in FIG. 12, the elongate member (1200) may be a flexible tube having a lumen in fluid communication with an opening at the distal tip (1202). In some variations, the distal end of the elongate member may be configured or modified to aid delivery of the fluid composition into Schlemm's canal. For example, the distal end of the elongate member may comprise a cut out configured as a half tube. Additionally or alternatively to an opening at the distal tip, the elongate member may optionally comprise a plurality of openings through its wall that are spaced along the axial length of the elongate member. In this variation, the fluid composition may be delivered from the reservoir through the openings in the elongate member and into Schlemm's canal. This lateral ejection of fluid (e.g., a viscoelastic fluid) may in some instances enhance disruption of outflow tissues and enhance permeability to aqueous humor. It is understood that the openings can be of any suitable number, size and shape, and spaced along the axial length of the elongate member (including the distal tip) in any suitable manner.

Drive Assembly

The delivery systems generally include a drive assembly. The drive assembly of the delivery system is generally configured to move an ocular device, elongate member, and/or fluid composition into Schlemm's canal. The drive assembly may also in some variations be configured to position an ocular device within the canal, including advancing the device into the canal and retracting the device from the canal. The drive assembly may be at least partially contained within the housing and may include any suitable component or combination of components capable of providing the handle with universal functionality.

The drive assembly may convert an external input (e.g., motion of a user's thumb or finger) into motion of one or more components of the delivery system. More specifically, the drive assembly may cause a slidable elongate member to be extended distally out of a cannula, and/or it may cause a slidable elongate member to be retracted proximally into a cannula. The drive assembly may also optionally cause a fluid composition to be delivered from a reservoir through the elongate member and/or cannula.

Two or more of these effects (i.e., extension of the slidable elongate member, retraction of the slidable elongate member, and/or delivery of a fluid composition) may be actuated using the same actuation mechanism. This may allow for single-handed use of the delivery system. For example, if the actuation mechanism comprises a rotatable element (such as one or more wheels, as in variations described herein), rotating the rotatable element in a first direction may cause extension of the slidable elongate member, and rotating the rotatable element in a second direction may cause retraction of the slidable elongate member. If the delivery system is configured to deliver a fluid composition, rotating the rotatable element (e.g., in the second direction) may also cause delivery of a fluid composition. The delivery of the fluid composition may be simultaneous with movement (e.g., retraction) of the slidable elongate member. In some of these instances, the fluid composition may be delivered to the portion of Schlemm's canal in which the slidable elongate member is advanced; that is, the fluid composition may be delivered to the same angle and length of Schlemm's canal as the extension of the elongate member. When the fluid composition is simultaneous with retraction of the elongate member, fluid composition may take the place of the slidable elongate member as it is retracted and may dilate Schlemm's canal and/or the collector channels at that location in Schlemm's canal. Furthermore, the quantity of fluid delivered may be tied to the amount of movement of the elongate member; that is, a certain predetermined, fixed volume of fluid composition may be delivered via the elongate member (e.g., delivered out of the distal end of the elongate member) for a fixed amount of movement of the elongate member (e.g., a retraction distance) and for a fixed amount of rotation of the rotatable element.

In some variations, the drive mechanism may be configured to allow the delivery system to be used only once—that is, the drive mechanism may prevent, for example, re-extension of the slidable elongate member after a predetermined amount of extension and/or retraction. Exemplary mechanisms by which external input may be converted into motion of one or more components of the delivery system are described in more detail below.

In some variations, the drive assembly includes components that translate rotational motion into linear motion. For example, the drive assembly may include a linear gear and a pair of pinion gear mechanisms. The linear gear may have teeth on its surface that engage corresponding teeth on the pinion gears. Each of the pinion gear mechanisms may also be coupled to a rotatable component (e.g., a wheel). Such coupling may be accomplished with a pin that can be threaded through a central opening in the rotatable component and pinion gear, and a nut that secures the rotatable component and pinion gear in a manner so that rotation of the rotatable component also rotates the pinion gear and vice versa. The wheels may be attached to the pinion gear by one of the following methods, for example: 1) the wheels and pinion gears are molded as one part using plastic injection molding technology; 2) the wheels slide onto the pinion gear and are secured with adhesive; or 3) the wheels slide on the pinion gear and are mechanically fixed with a fastener or a "press fit," where the wheels are forced onto the pinion gear and friction holds them secure. In all of the mentioned situations, the wheels and pinion gears may rotate coaxially, in the same direction, and at the same angular rate. In some variations, each of the pinion gear mechanisms is coupled to at least two rotatable components. In other variations, the drive assembly may be configured to include a single rotatable component, a plurality of rotatable components, or no rotatable component. The wheel may have markings or colorings to indicate degree of advancement or direction of advancement.

One variation of the drive assembly useful to include in the universal handle comprises a linear gear, a pair of pinion gear mechanisms, and two rotatable components coupled to each pinion gear (for a total of four rotatable components). In other variations, the drive assembly includes a linear gear and a single pinion gear mechanism with two associated wheels. In variations with a pair of pinion gear mechanisms, the pinion gear mechanisms and associated wheels would be disposed on either side of the linear gear. The pinion gears and linear gear would contact each other, i.e., the teeth of the pinion gears would directly engage corresponding teeth on the linear gear, and the wheels on one side of the linear gear would contact the wheels on the opposite side of the linear gear. At least a portion of the wheels on each side of the linear gear would extend outside of the housing. In this variation, the drive assembly can be manipulated with one hand when in a first configuration, and then manipulated with the same or the other hand when flipped over to a second configuration. A drive assembly having such flexible capability can be easily used by a surgeon who is right hand dominant or left hand dominant, and may also be used in a procedure in which the handle is flipped during a procedure such that the cannula is facing a first direction in a first portion of the procedure, and facing a second direction in a second portion of the procedure. In a further variation, the drive assembly may include one rotatable component on one side of the handle and the "universal" feature of the handle provided by a cannula that itself can rotate instead of flipping the handle.

Figure 4A:
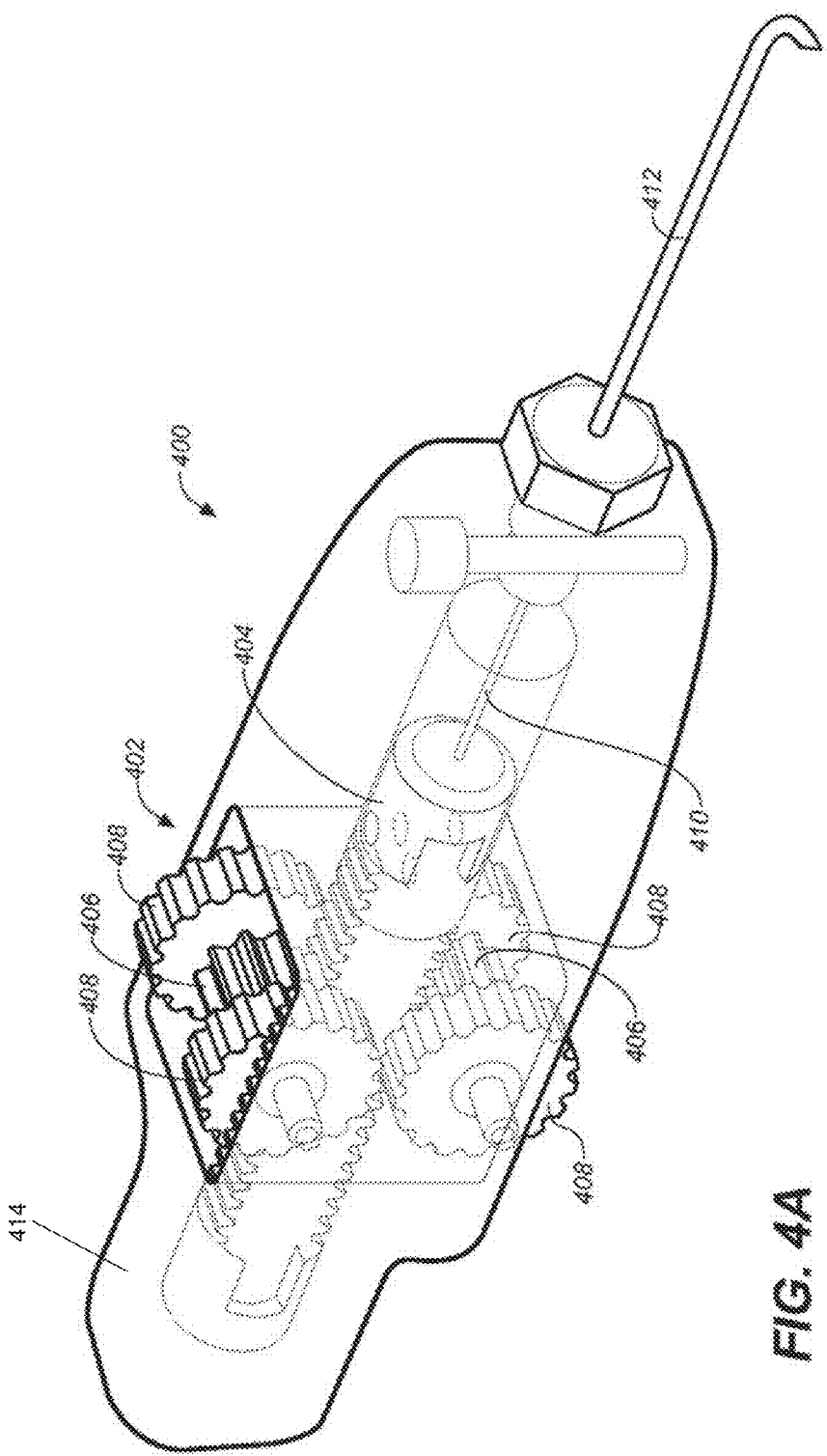

In the variation shown in FIG. 4A, delivery system (400) includes a drive assembly (402) having a linear gear (e.g., a rack) (404) and a pair of pinion gear mechanisms (406). Both the linear gear and the pinion gear mechanisms have teeth that engage each other to translate rotational motion (of the pinion gear mechanisms (406)) to linear motion (of the linear gear (404)). Each of the pinion gear mechanisms (406) is coupled to two rotatable components, shown in the figure as wheels (408), for a total of four rotatable components. The wheels (408) extend outside of the housing (414) of the delivery system (400), and as such, may be rotated by one or more of the surgeon's fingers to correspondingly rotate the pinion gear mechanism (406) and thus advance or retract the linear gear (404). The wheels (408) are coaxial with the pinion gear mechanism (406) and rotate in unison with the pinion gear mechanism. Movement of the linear gear (404) advances or retracts a positioning element (410) that is coaxially disposed and slidable within cannula (412). FIG. 4B shows the system of FIG. 4A in a second, flipped orientation. In the orientation of FIG. 4A, the cannula is oriented with the curvature facing clockwise, while in the orientation of FIG. 4B, the cannula is oriented with the curvature facing counterclockwise. The extension of wheels (408) outside of the housing (414) on either side may allow the delivery system (400) to be used in either orientation, with either hand, and on either of the patient's eyes. That is, the orientation of FIG. 4B can be used with the opposite hand or the same hand as the orientation of FIG. 4A, but when a different direction of cannulation is desired (e.g., clockwise cannulation if counterclockwise cannulation was performed with the system in FIG. 4A).

Figure 22A:
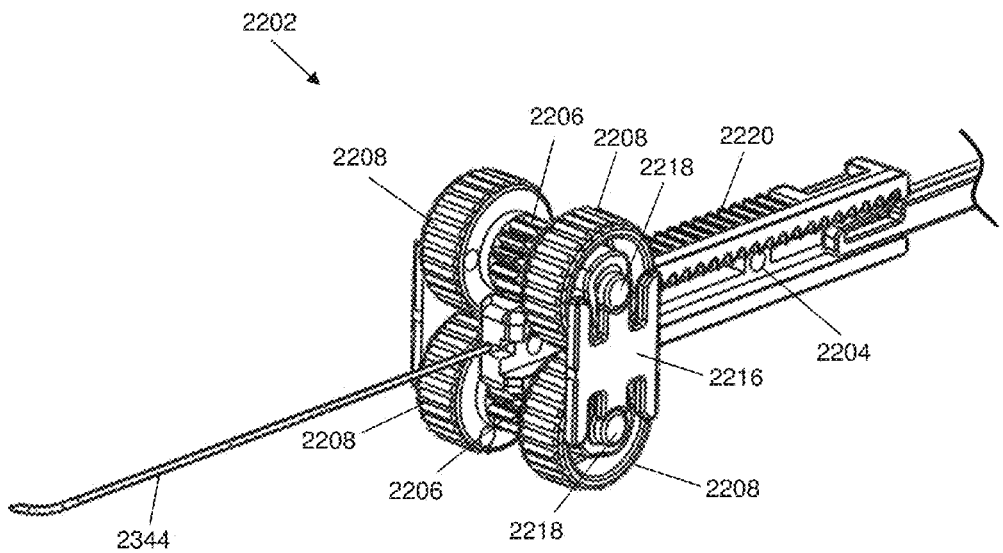
FIGS. 22A-22B depict perspective views of an exemplary drive assembly of a delivery system.
Figure 22B:
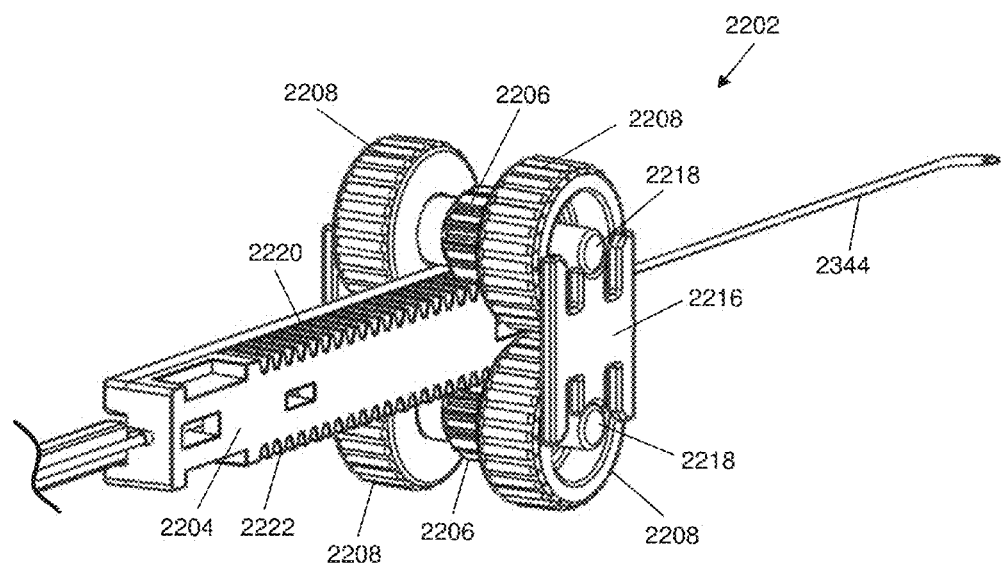

Another variation of a drive assembly is shown in two different perspective views in FIGS. 22A-22B. As depicted there, a drive assembly (2202) may comprise a linear gear (e.g., a rack) (2204) and a pair of pinion gear mechanisms (2206). Both the linear gear and the pinion gear mechanisms have teeth that engage each other to translate rotational motion (of the pinion gear mechanisms) to linear motion (of the linear gear). More specifically, the linear gear (2204) may comprise teeth on both a first side (2220) and a second side (2222), where the teeth on the first side engage the first pinion gear mechanism, and the teeth on the second side engage the second pinion gear mechanism. Each of the pinion gear mechanisms (2206) is coupled to two rotatable components, shown in the figure as wheels (2208), for a total of four rotatable components. The wheels (2208) are coaxial with the pinion gear mechanisms (2206) and rotate in unison with the pinion gear mechanisms. The drive assembly may comprise one or more features to stabilize the pinion gear mechanisms or otherwise keep them in place. For example, the drive assembly (2202) may comprise wheel spacers (2216) configured to sit between axles (2218) of the pinion gear mechanisms. Rotation of one or more wheels (2208) may cause translation of the linear gear (2204).

Figure 22C:
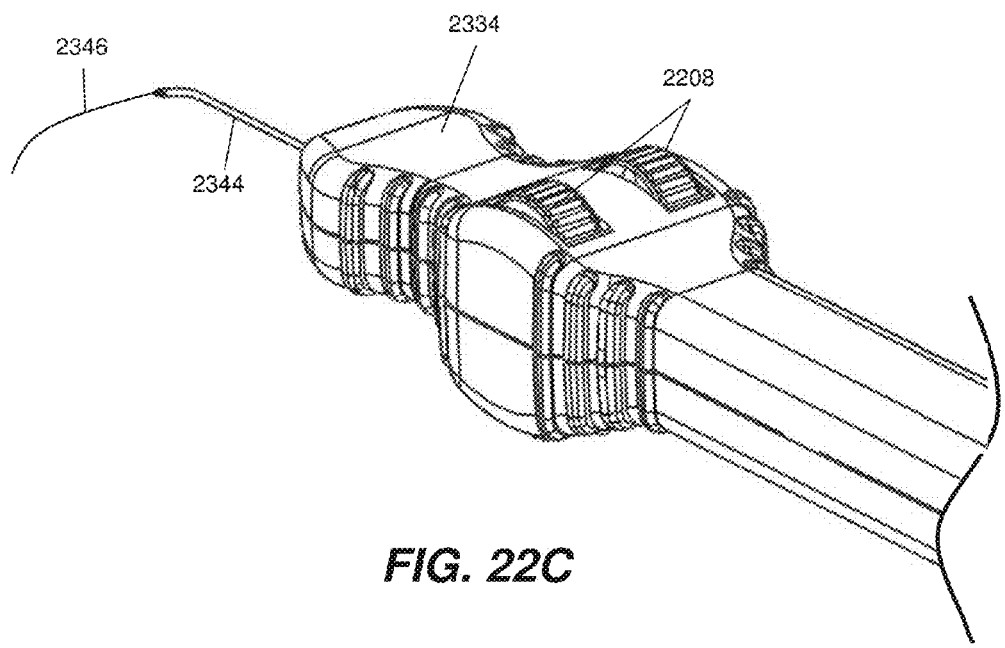
FIG. 22C shows a perspective view of the delivery system with an extended slidable elongate member.
Figure 23A:
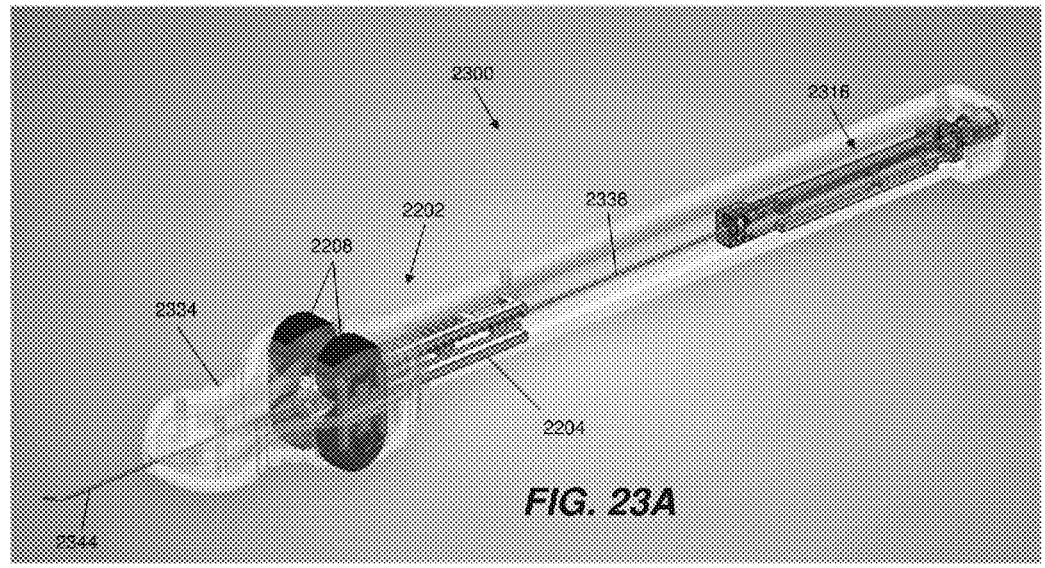
FIG. 23A shows a perspective view of an exemplary delivery system for delivering a fluid.
Figure 23B:
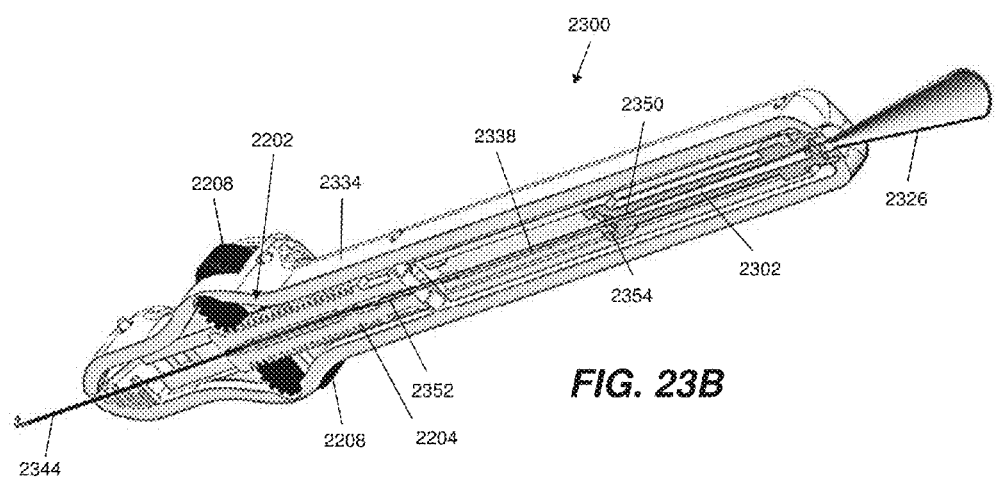
FIG. 23B shows a cutaway view of the delivery system of FIG. 23A.
Figure 23C:
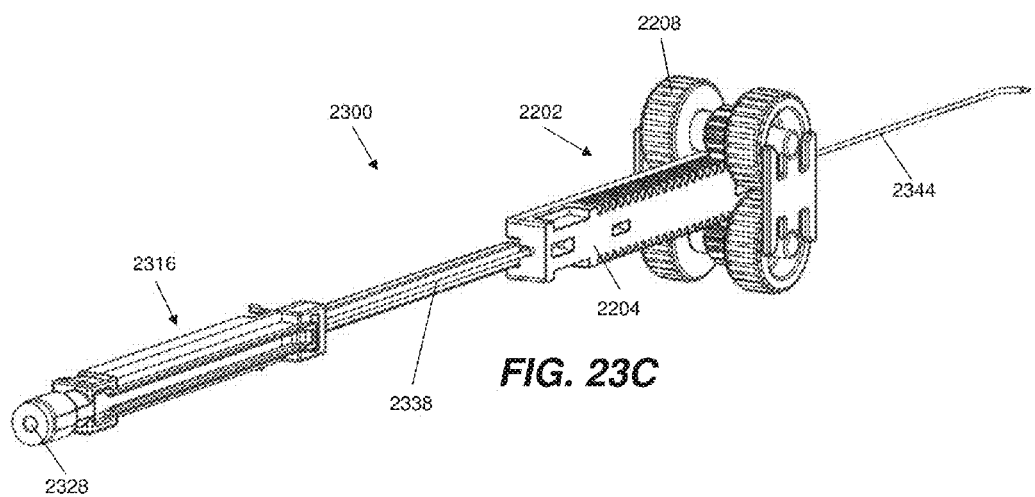
FIGS. 23C-23D show perspective views of the delivery system of FIG. 23A without the housing.

As shown in FIGS. 22C and 23A-23B, the wheels (2208) may extend out of the housing (2334) of the delivery system, such that the wheels may be rotated by a surgeon to correspondingly rotate the pinion gear mechanisms (2206) and thus advance or retract the linear gear (2204). The cannula (2344) may be slidable within the linear gear (2204), such that the cannula and wheels are fixed relative to each other and relative to the housing (2334), while the linear gear (2204) translates relative to the housing. Because linear motion of the linear gear (2204) may be generated by rotational motion of either of the two pinion gear mechanisms (2206), which may in turn be generated by rotating any of the wheels (2208) extending from the housing (2334), the delivery system (2300) may be easily operated using a single hand with either the first side or the second side facing upwards, and thus with the cannula (2344) facing a first direction or a second direction.

In other variations, one or both pinion gear mechanisms may be able to be disengaged from the linear gear by biasing their position off axis from the linear gear. This action de-couples the pinion gear teeth to the linear gear teeth to prevent linear gear movement. The pinion gear mechanism may also be able to be locked to prevent rotation by engaging an intersecting pin or feature that prevents wheel rotation.

Further variations of the drive assembly may not employ translation of rotational motion to linear motion. For example, a slide (e.g., a finger slide) on the handle that is fixed or detachably coupled to a gear within the housing of the handle (e.g., a linear gear as previously described). Here the drive assembly may be configured so that advancement or retraction of the slide causes advancement or retraction of an ocular device and/or elongate member, and/or delivery of a fluid composition into Schlemm's canal. In yet further variations, a button that can be pressed or squeezed could be employed instead of a slide, or a foot pedal could be employed to deliver an ocular device, tool, and/or fluid composition.

Extending and Retracting the Elongate Member

In some variations, a proximal end of the elongate member may be fixed relative to a portion of a drive assembly (e.g., the linear gear (2204)), while the distal end may be slidably and coaxially disposed within the cannula lumen. When the elongate member does not comprise a lumen (e.g., is a filament), the elongate member may in some instances be attached to the drive assembly via crimping. When the elongate member comprises a lumen, the elongate member may in some instances be bonded to the drive assembly (e.g., via an adhesive) in order to leave the lumen of the elongate member unobstructed. The cannula, in turn, may be fixedly attached to the housing. In variations of the delivery systems in which the handle is reusable and the cannula and elongate member are disposable, a disposable assembly comprising the elongate member pre-loaded within the cannula may be attached to the reusable handle via any suitable mechanism, such as a threaded fastener or snap-in feature.

Figure 22D:
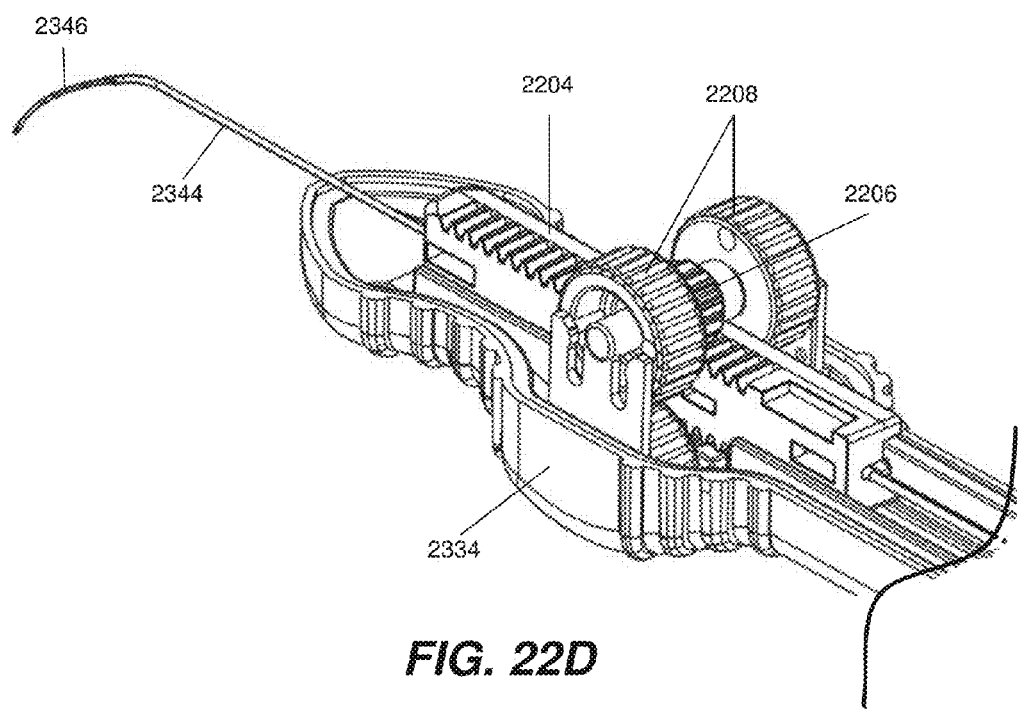
FIG. 22D shows a perspective view of the delivery system without a top portion of the housing with an extended slidable elongate member.

When the portion of the drive assembly is moved proximally or distally within the housing, this may cause corresponding movement of the elongate member relative to the cannula. That is, movement of the portion of the drive assembly toward the cannula (i.e., toward the distal end of the housing) may cause the elongate member to move from a retracted position to an extended position, and movement of the portion of the drive assembly away from the cannula (e.g., toward the proximal end of the housing) may cause the elongate member to move from an extended position to a retracted position. An example of an elongate member in an extended position is shown in FIGS. 22C-22D. As shown in the view in FIG. 22D with the top portion of the housing (2334) removed, the linear gear (2204) is in a distal position. As such, the elongate member (2346) is extended from cannula (2344).

Reservoir

The systems generally include a reservoir when a fluid composition is to be delivered into Schlemm's canal. The reservoir may contain various fluid compositions for delivery. Exemplary fluid compositions include saline and viscoelastic fluids. The viscoelastic fluids may comprise hyaluronic acid, chondroitin sulfate, cellulose, derivatives or mixtures thereof, or solutions thereof. In one variation, the viscoelastic fluid comprises sodium hyaluronate. In another variation, the viscoelastic composition may further include a drug. For example, the viscoelastic composition may include a drug suitable for treating glaucoma, reducing or lowering intraocular pressure, reducing inflammation, and/or preventing infection, fibrosis, scarring, clotting, thrombosis, bleeding, or neovascularization. Drugs such as anti-metabolites, vasoconstrictors, anti-VEGF agents, steroids, heparin, anti-inflammatories, nonsteroidal anti-inflammatories (NSAIDs), other anticoagulants, fibrinolytic compounds, biologic agents, and gene therapy drugs may also be delivered in combination with the viscoelastic composition. Examples of glaucoma drugs include prostaglandins, beta blockers, miotics, alpha adrenergic agonists, or carbonic anhydrase inhibitors. Anti-inflammatory drugs such as NSAIDs, corticosteroids or other steroids may be used. For example, steroids such as prednisolone, prednisone, cortisone, cortisol, triamcinolone, or shorter acting steroids may be employed. Examples of antimetabolites include 5-fluoruracil or mitomycin C. Examples of drugs or antibodies that prevent neovascularization include bevacizumab, ranibizumab, and others. In still another variation, the system delivers the drug alone, without the viscoelastic composition. Saline solution may also be the fluid employed. In yet other variations, the system may be configured to deliver a gas, such as but not limited to air, an expansile gas (e.g., SF6, C3F8).

In some variations, the reservoir may be at least partially defined by a fluid assembly and the housing, and the linear gear within the handle. The fluid assembly may be made from any suitable material previously mentioned for the cannula and the housing. The volume of fluid (in microliters) contained within the reservoir may range from about 2 µl to about 1000 µl, or from about 2 µl to about 500 µl. In some variations, the reservoir volume may range from about 50 µl to about 100 µl.

The fluid composition may be preloaded in the reservoir or loaded into the reservoir prior to use of the system, e.g., at the start of an ocular procedure, so that the fluid can be delivered by a single device and by a single user. Again, this is in contrast to other systems that use forceps or other advancement tools to advance a fluid delivery catheter into Schlemm's canal and/or devices containing viscoelastic fluid that are separate or independent from a delivery catheter or catheter advancement tool, and which require connection to the delivery catheter or catheter advancement tool during a procedure by, e.g., an assistant, or by the hand of the surgeon while the delivery catheter or catheter advancement tool is held by another hand of the surgeon. For example, a loading component may be provided on the fluid assembly for transfer of a fluid composition into the reservoir. The loading component may have any suitable configuration that provides reversible securement of a fluid container, e.g., a syringe, cartridge, etc., to the system, and loading of a fluid composition into the reservoir. The loading component may be a luer fitting or include a one-way valve.

Figure 23D:
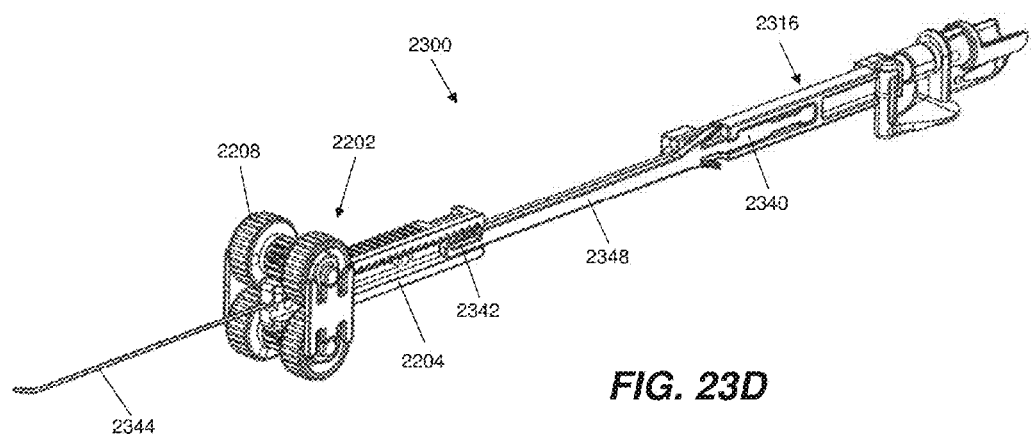
Figure 23E:
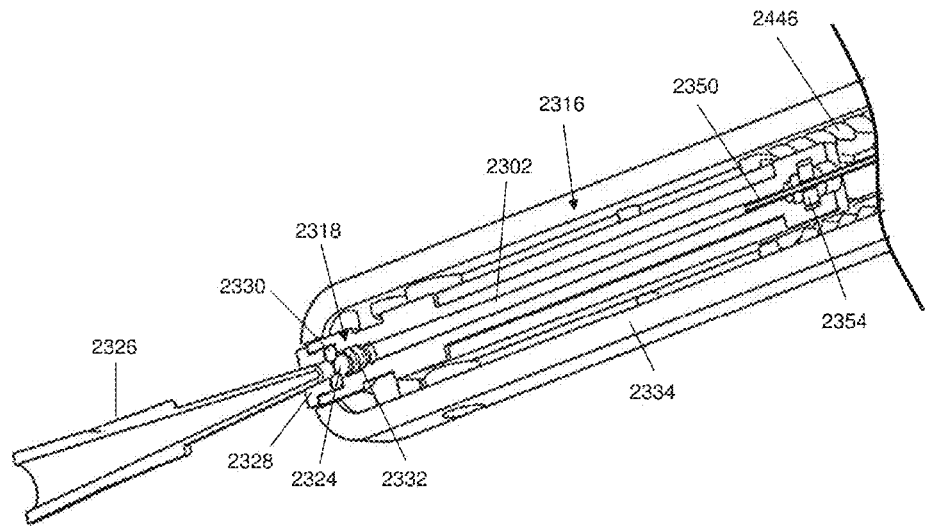
FIG. 23E shows a close-up cutaway view of the proximal end of the delivery system of FIG. 23A.

An exemplary delivery system comprising a reservoir is shown in FIGS. 23A-23F. Shown there with (FIGS. 23A, 23B, and 23E), without (FIGS. 23C and 23D), and partially without (FIG. 23F) a housing (2334), the delivery system (2300) comprises a fluid assembly (2316) comprising a reservoir (2302). In an exemplary method, a fluid composition may be loaded into the reservoir (2302) through a proximal opening (2328) via a proximal seal (2318). As best shown in FIG. 23E, the distal end of the reservoir (2302) may be formed by a plunger (2338) (explained in more detail below) and a distal seal (2354).

The proximal seal (2318) may be a mechanical seal located at the proximal end of the reservoir (2302) and comprising a ball bearing (2324) spring-biased against an o-ring or gasket (2330) to seal closed the reservoir. A loading tool (2326) (e.g., a nozzle) may be used to open the seal by pressing against the ball bearing (2324) to move it proximally toward an open position. While the proximal seal (2318) is open, the fluid composition may be loaded into the reservoir. After loading of the fluid composition, the loading tool (2326) may be removed, allowing the ball bearing (2324) to return to its closed position. The close-up cross-sectional view in FIG. 23E shows the proximal opening (2328) and ball bearing (2324). An o-ring or gasket (2330) sits between the ball bearing (2324) and a spring (2332), such that force from the spring presses the ball bearing into the gasket to form a seal between the ball bearing and gasket in the closed position. The loading tool (2326) is configured to fit into the proximal opening (2328) to press against the ball bearing (2324). The distally oriented force against the ball bearing (2324) moves it distally into the open position, compressing the spring (2332), and creating an opening between the ball bearing and the gasket (2330), through which the fluid composition may flow. When the loading tool (2326) is removed from the proximal opening (2328), the spring (2332) pushes the ball bearing (2324) proximally back into the closed position.

Figure 24:
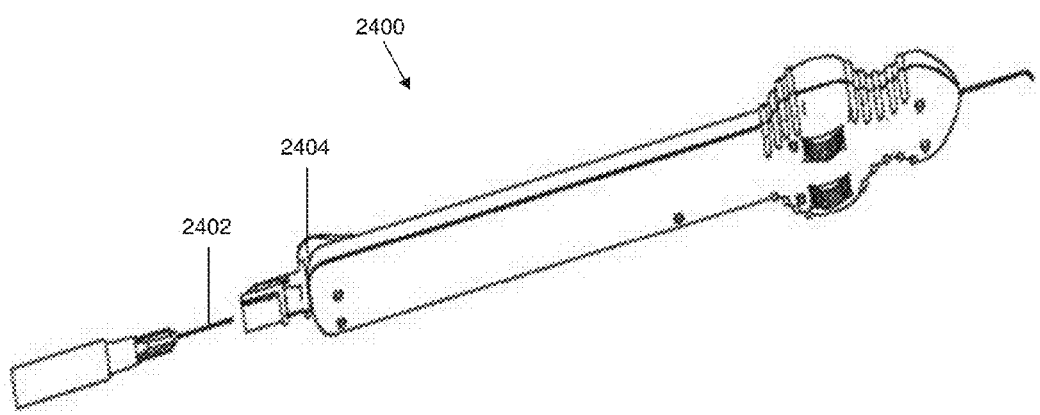
FIG. 24 depicts a perspective view of another exemplary delivery system for delivering a fluid.

It should be appreciated that in other variations, the reservoir may comprise other types of seals allowing a fluid composition to be loaded into the reservoir. For example, FIG. 24 depicts an alternative variation of a delivery system (2400), wherein the seal comprises a membrane (e.g., a silicone membrane). As shown, a fluid composition may be loaded (after movement of the optional lock (2404)) into the reservoir by puncturing the membrane with a needle (2402) (e.g., a 25 gauge needle). In yet other variations, the delivery systems described herein may be configured to receive a prefilled cartridge comprising a fluid composition. For example, the handle and fluid assembly may be configured such that a prefilled cartridge can be inserted into the fluid assembly.

In order to load the reservoir, it may be desirable to at least temporarily secure the fluid assembly in place in order to allow application of distal force to the seal. In some variations, the delivery system may comprise a lock configured to hold the fluid assembly in place while a fluid composition is injected into the reservoir. However, it should be appreciated that in other variations the delivery system may not comprise a lock. In variations having a lock, it may be desirable for the lock to be removable from the delivery system (or to otherwise release the fluid assembly) in order to allow the fluid assembly to translate relative to the housing after the reservoir is loaded. Translation of the fluid assembly may allow for extension of the slidable elongate member and/or injection of the fluid composition during the procedure, as is described in more detail herein.

In variations of the delivery systems having a lock, the lock may optionally additionally act as a cap to protect a distal opening to the reservoir. In these variations, the lock may comprise a first configuration in which it both holds the reservoir in place and covers the proximal opening to the reservoir, and a second configuration in which it holds the reservoir in place but allows the proximal opening to the reservoir to be accessed, such that the reservoir can be loaded with a fluid composition. In some instances, the lock may rotate from the first position to the second position.

Figure 25A:
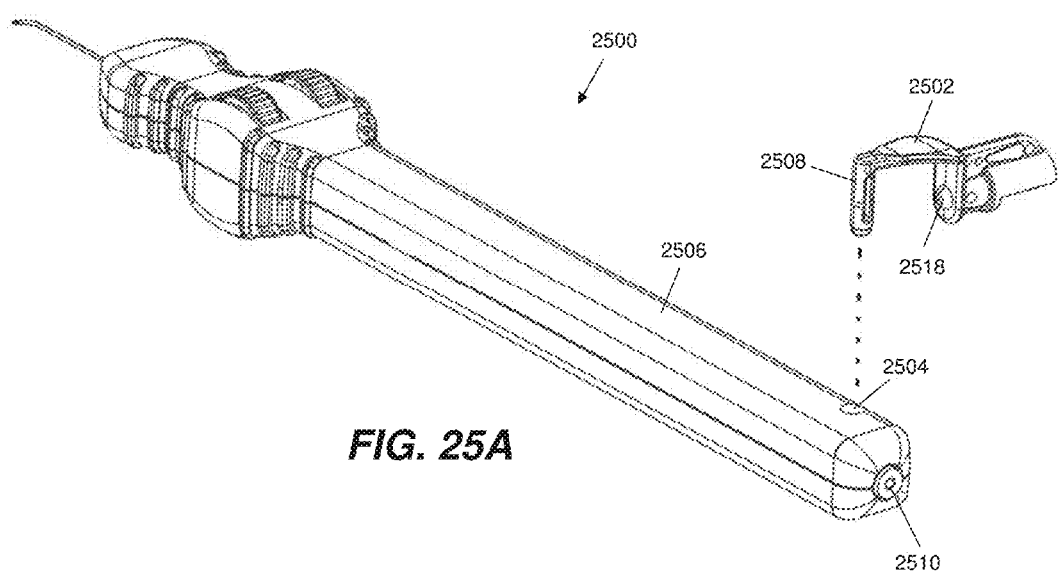
FIGS. 25A-25B depict perspective views of an exemplary delivery system with a lock removed (FIG. 25A) and inserted (25B) into the handle.
Figure 25B:
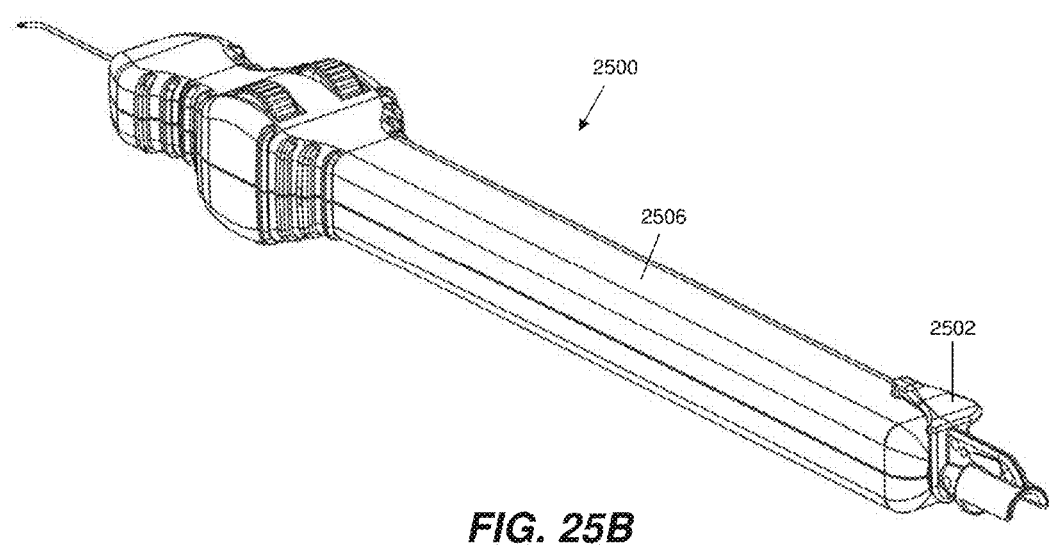
Figure 25C:
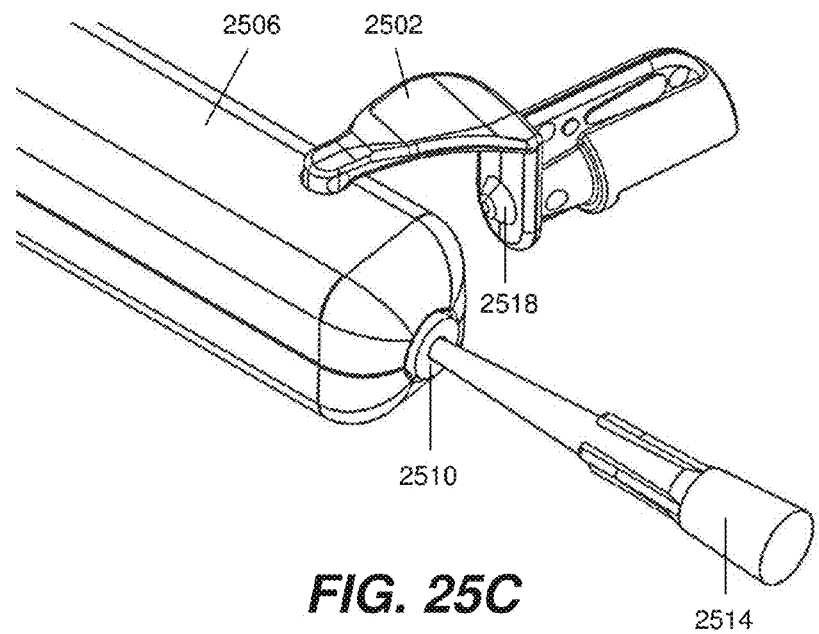
FIGS. 25C-25D show perspective and cutaway views, respectively, of the lock rotated to allow loading of the reservoir.
Figure 25D:
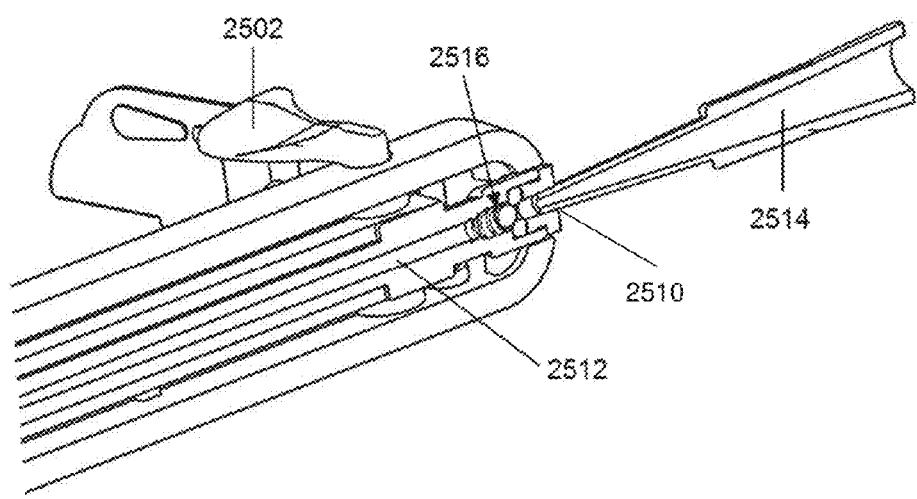

FIGS. 25A-25D illustrate an exemplary lock (2502). As shown there, the lock (2502) may comprise a pin (2508) configured to fit into an opening (2504) in the handle (2506) of the delivery system (2500). In a first configuration, shown in FIG. 25B, the lock (2502) may be inserted into the opening (2504) in the handle and may cover the proximal opening (2510). The lock (2502) may comprise a protrusion (2518) configured to interface with the proximal opening (2510) to stabilize the lock in the first configuration. In a second configuration, shown in FIGS. 25C-25D, the lock (2502) may remain inserted into the opening (2504) but may pivot within the opening to expose the proximal opening (2510) to allow loading of the reservoir (2512). When the pin (2508) is inserted into the opening (2504), the pin may restrict movement of the reservoir (2512) relative to the housing. This may allow a loading tool (2514) to apply force through the proximal opening (2510) to open the proximal seal (2516) of the reservoir (2512), without the reservoir sliding distally within the handle (2506). Restricting movement of the reservoir (2512) relative to the handle (2506) may prevent motion of the reservoir or other internal components of the delivery system before use (e.g., during transit). Once loading of the reservoir (2512) is complete, the lock (2502) may be removed from the opening (2504), as shown in FIG. 25A, at which point the reservoir (2512) may no longer be restricted by the lock from moving relative to the housing.

Delivering a Fluid Composition

The delivery systems described herein may be configured to deliver fluid to Schlemm's canal. The fluid may be delivered in a volume that provides sufficient force to disrupt Schlemm's canal and surrounding trabeculocanalicular tissues. Exemplary disruptive volumes may be about 1 µl, about 2 µl, about 3 µl, about 4 µl, about 5 µl, about 6 µl, about 7 µl, about 8 µl, about 9 µl, about 10 µl, about 11 µl, about 12 µl, about 13 µl, about 14 µl, about 15 µl, about 16 µl, about 17 µl, about 18 µl, about 19 µl, or about 20 µl. In some variations, the disruptive volume fluid may range from about 1 µl to about 50 µl, or from about 20 µl to about 50 µl.

As mentioned above, a elongate member may be coaxially disposed within the cannula lumen. In variations of the delivery system configured to deliver a fluid composition, the elongate member may comprise a lumen. The lumen of the elongate member may be operatively connected to a reservoir for delivery of a fluid composition into Schlemm's canal. The elongate member generally has a proximal end, a distal end, and a wall that defines the lumen extending therethrough. However, in some instances, the delivery system lacks an elongate member conduit, and the fluid composition is delivered solely through the cannula. In other instances, two elongate members may be employed that each simultaneously advance through the canal in both clockwise and counterclockwise directions to more rapidly cannulate Schlemm's canal and deliver therapy.

Figure 10A:
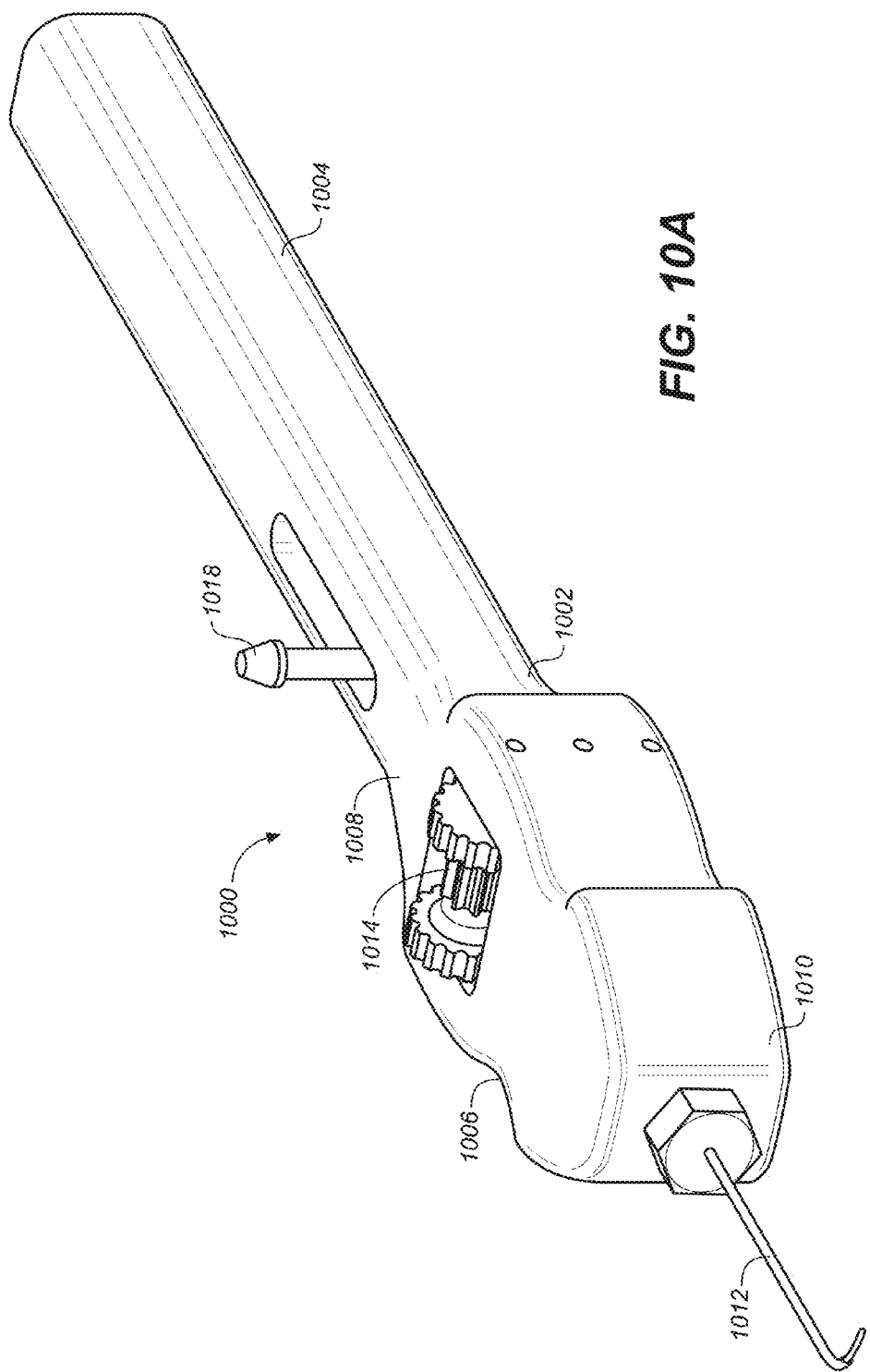

When the delivery systems are employed to deliver a fluid composition, the fluid composition may be preloaded in a reservoir of the system or loaded into the reservoir prior to use of the system. An exemplary delivery system for delivering a fluid composition into Schlemm's canal is shown in FIGS. 10A and 10B. Referring to FIG. 10A, delivery system (1000) includes a universal handle (1002) having a grip portion (1004) and a housing (1006). Housing (1006) has a proximal end (1008) and a distal end (1010). A cannula (1012) is coupled to and extends from the housing distal end (1010). A drive assembly (1014) is substantially contained within the housing (1006) that actuates movement of a slidable elongate member (not shown). The cannula (1012) and drive assembly (1014) have the same configuration as that shown and described in FIGS. 3 and 4A-4B for the system tailored for ocular device implantation, and thus are not described in detail here.

The delivery system (1000) also includes a fluid assembly (1016) (shown in FIG. 10B) within the handle (1002) having a loading component (1018) that is configured to allow transfer of a fluid composition from an external source into a reservoir defined by the fluid assembly and linear gear (1020). A slidable elongate member (1022) is coaxially disposed within the cannula lumen that is in fluid communication with the reservoir. As previously stated, in a tool-based system that does not deliver an implant or a fluid, the system may not include a reservoir.

In an exemplary method, as illustrated by FIGS. 11A-11C, a fluid composition may be transferred into a reservoir (1102) of system (1100) via loading through loading component (1104). As shown in the figures, reservoir (1102) is defined by the fluid assembly (1106) and the linear gear (1108). Linear gear (1108) has a proximal end (1110) and a distal end (1112), and a lumen (1114) extending from the proximal end (1110) to the distal end (1112). Lumen (1114) is in fluid communication with the lumen (not shown) of the slidable elongate member (1118). To deploy the fluid composition out of the reservoir (1102), linear gear (1108) is retracted in the direction of the arrow (FIG. 11B) so that reservoir (1102) becomes pressurized. Retraction can be accomplished by rotation of pinion gear mechanisms (1120). Once a sufficient amount of pressure has been created in the reservoir (1102) the fluid composition contained therein is injected through linear gear lumen (1114) and the lumen of elongate member (1118) into Schlemm's canal.

Figure 13A:
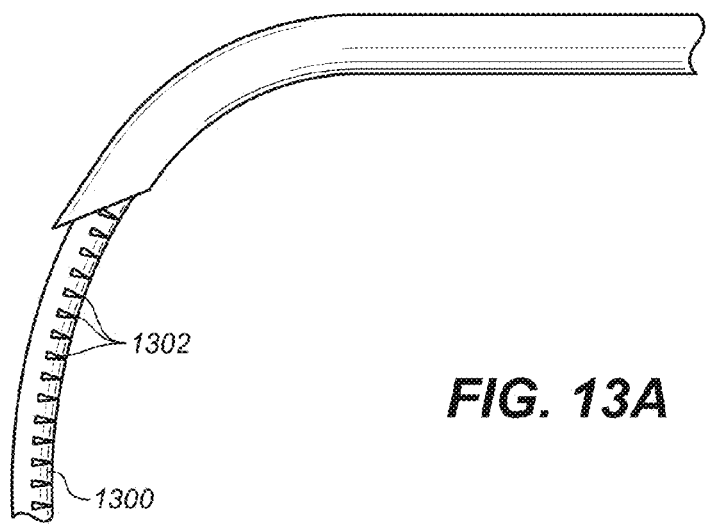
FIGS. 13A-13C show side or perspective views of slidable elongate members according to other variations.
Figure 13B:
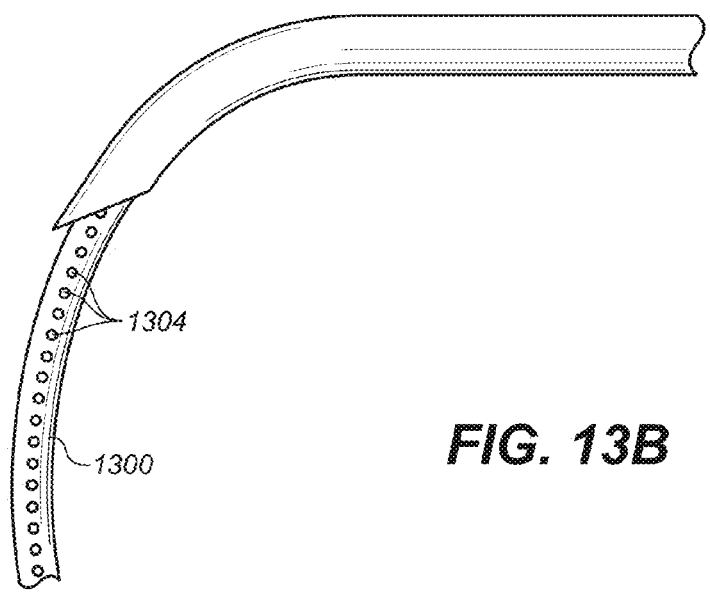
Figure 13C:

Here, any fluid that is delivered flows through the distal end (1202) to reach Schlemm's canal. In other variations, the slidable elongate member (1300) may be configured to include a plurality of openings spaced along its axial length. The openings may have any suitable shape, e.g., slots (1302) (FIG. 13A) or circles (1304) (FIG. 13B). Fluid compositions delivered using the elongate members depicted in FIG. 13A and FIG. 13B may partially flow out of the elongate member through the openings and partially out through the distal end of the elongate member. The distal end of the elongate member may also be configured as a half tube (1306) (FIG. 13C).

Some variations of the fluid assembly include a locking mechanism for preventing movement of the assembly within the handle, e.g., when the linear gear is being advanced or retracted. The locking mechanism may comprise a ratchet pawl, a combination of ratchet pawls or any other suitable mechanism that can be locked to prevent movement of the fluid assembly, and unlocked to allow movement of the fluid assembly.

Referring back to FIGS. 23A-23F, another exemplary delivery system (2300) for delivering a fluid composition into Schlemm's canal shown there may comprise a housing (2334) and a cannula (2344) extending from the distal end of the housing. A drive assembly (2202) (described above with respect to FIGS. 22A-22D) may be located within the housing (2334), as may be a fluid assembly (2316) (described in more detail above). As described above, the drive assembly (2202) may comprise a linear gear (2204) and a pair of pinion gear mechanisms (2206) coupled to wheels (2208). The delivery system (2300) may comprise a slidable elongate member (2336). A proximal end of the elongate member may be fixed relative to the linear gear (2204), while the distal end of the elongate member may be slidably and coaxially disposed within the lumen of the cannula (2334). A reservoir (2302) of the fluid assembly (2316) may be fluidly connected to a lumen of the elongate member. For example, a plunger (2338) comprising a lumen may fluidly connect the reservoir (2302) to the lumen of the elongate member. The proximal end (2350) of the plunger (2338) may be located slidably within the reservoir (2302), and the distal end (2352) of the plunger may be fixedly attached to the linear gear (2204) of the drive assembly (2202).

The fluid assembly (2316) and the drive assembly (2202) may be connected via a linkage (2348), as best shown in FIG. 23D. (The delivery system (2300) is shown without the linkage assembly in FIG. 23A in order to better show other components.) The linkage (2348) may be configured to allow the fluid assembly (2316) and drive assembly (2202) to be moved as a unit, and may allow limited movement of the fluid assembly and drive assembly relative to each other. In some variations, the linkage (2348) may allow the fluid assembly (2316) to be moved closer but not farther from the drive assembly (2202). For example, as best shown in FIG. 23D, the proximal end (2340) of the linkage (2348) may be fixedly attached to the fluid assembly (2316). The distal end (2342) of the linkage (2348) may be attached via a one-way ratchet to the linear gear (2204) of the drive assembly (2202). The distal end (2342) may be able to be moved distally along a track in the linear gear (2204), but teeth in the track may resist proximal movement of the distal end (2342) along the track. As such, the fluid assembly (2316) may be able to be moved distally toward the linear gear (2204), such that the fluid assembly and linear gear are brought closer together (via shortening of the portion of the linkage (2348) between the fluid assembly and the linear gear), but the fluid assembly may not be able to be moved proximally away from the linear gear. It should be appreciated that in other variations, a linkage may be fixedly attached to the linear gear and slidably attached to the fluid assembly.

Thus, the linear gear (2204) and the fluid assembly (2316) may be movable relative to each other and may be movable within the housing (2334). Movement of the linear gear (2204) and fluid assembly (2316) relative to each other, as well as relative to the housing (2334), may cause one or more effects, including extension and retraction of the slidable elongate member and/or delivery of a fluid composition. More specifically, because the proximal end (2350) of the plunger (2338) may be located slidably within the reservoir (2302) and the distal end (2352) of the plunger may be fixedly attached to the linear gear (2204), movement of the reservoir closer to linear gear may cause proximal movement of the plunger within the reservoir. This may cause the length of the plunger (2338) located within the reservoir (2302) to increase. The portion of the plunger (2338) within the reservoir (2302) may displace fluid within the reservoir. The displaced fluid may move distally through the lumen of the plunger (2338), through the lumen of the elongate member (2336), and may be delivered out through a distal opening of the lumen of the elongate member.

Additionally, as mentioned above, movement of the linear gear (2204) relative to the housing (2334) may cause the slidable elongate member (2336) to extend or retract. The linear gear (2204) may be moveable between proximal and distal positions via rotation of the wheels (2208), while the wheels (2208) remain fixed relative to the housing (2334). Because the proximal end of the elongate member may be fixed relative to the linear gear (2204) and the distal end of the elongate member may be slidable within the lumen of the cannula (2344), when the drive assembly (2202) is in a proximal position, the elongate member may correspondingly be in a retracted position relative to the cannula (2344). When the elongate member is in the retracted position, the distal end of the elongate member may be located within the cannula (2344) (e.g., proximal to the distal tip of the cannula). When the drive assembly (2202) is in a distal position, the elongate member may correspondingly be in an extended position relative to the cannula (2344). When the elongate member (2336) is in the extended position, the distal end of the elongate member may extend out of the cannula (e.g., distal to the distal tip of the cannula).

Figure 23F:
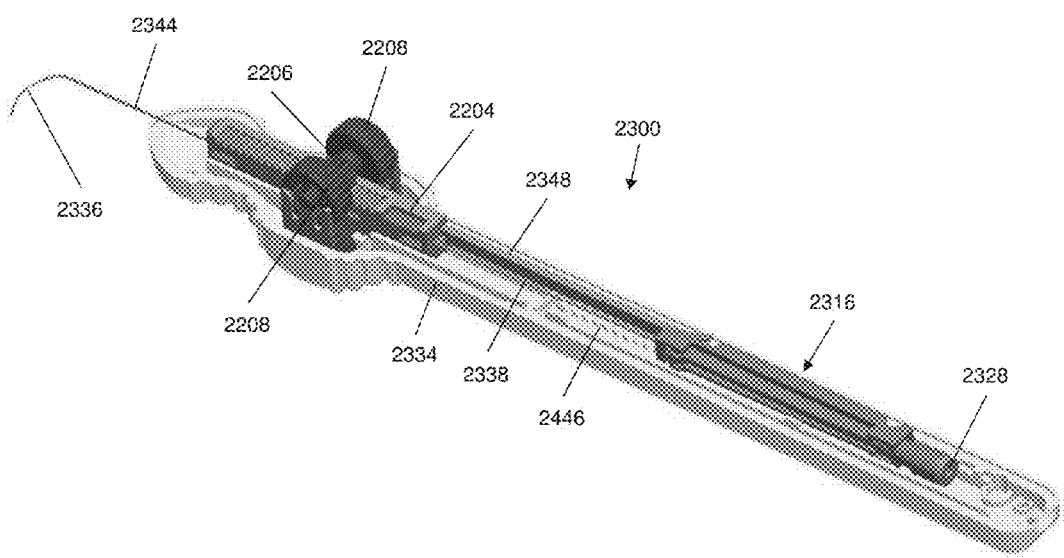
FIG. 23F shows a perspective view of the delivery system of FIG. 23A without a top portion of the housing with an extended slidable elongate member.

Relative motion of the drive assembly (2202), fluid assembly (2316), and housing (2334) may thus be used to extend the slidable elongate member (2336) within Schlemm's canal, and to retract the elongate member within Schlemm's canal while simultaneously delivering fluid. The delivery system (2300) may start in a configuration where the fluid assembly (2316) and linear gear (2204) are separated by the full distance of the linkage (2348), the fluid assembly is located at the proximal end of the housing (2334), and the slidable elongate member is in a retracted position within the cannula (2344). This configuration is shown in FIGS. 23A-23D. The wheels (2208) may be rotated in a first direction to advance the linear gear (2204) distally within the housing (2334). The linkage (2348) may cause the fluid assembly (2316) to move an equal distance distally within the housing, maintaining the spacing between the fluid assembly and linear gear (2204). As the linear gear (2204) advances, the elongate member (2336) may move from the retracted position to an extended position. This may cause the elongate member (2336) to travel though Schlemm's canal. This configuration is shown in FIG. 23F, which depicts the delivery system (2300) without a top portion of the housing (2334) to show the linear gear (2204) in a distal position. As can be seen there, the elongate member (2336) is in an extended position relative to the cannula (2344), and the fluid assembly (2316) is also in a distal position within the housing (2334).

The wheels (2208) may then be rotated in a second direction to retract the linear gear (2204) proximally within the housing (2334). This may cause the slidable elongate member (2336) to move from the extended position to the retracted position. However, the fluid assembly (2316) may not correspondingly move proximally within the housing (2334). The housing (2334) may comprise interior teeth (2446) near the fluid assembly (2316) configured to engage exterior teeth on the fluid assembly. These teeth may allow the fluid assembly (2316) to move distally within the housing (2334) but not proximally within the housing. As such, when the linear gear (2204) is retracted within the housing (2334), the fluid assembly (2316) may remain fixed relative to the housing. The linear gear (2204) and fluid assembly (2316) may therefore move closer together, with the linkage (2348) moving distally along a track in the linear gear (2204) to accommodate this movement. As the linear gear (2204) and fluid assembly (2316) move closer together, the plunger (2338) may displace fluid within the reservoir (2302), as described in more detail above. The fluid may then travel through a lumen of the plunger (2338) and be delivered through the lumen of the elongate member (2336).

In this way, as the elongate member is retracted, fluid may be delivered simultaneously out of the elongate member. The fluid may take the place of the elongate member as it is retracted, and as such, the fluid may be delivered to an angle and length of Schlemm's canal that is the same as the angle and length about which the elongate member was advanced. A fixed, predetermined volume of fluid may be delivered for a given amount of retraction of the elongate member, due to displacement of the fluid in the reservoir by the plunger, and both the retraction of the elongate member and the delivery of a fluid composition may be effectuated by a single user motion (rotation of a wheel (2208)). In some instances, full retraction of the elongate member may result in the delivery of between about 2 µl and about 9 µl of fluid. In some of these instances, full retraction of the elongate member may result in the delivery of about 4.5 µl of fluid. As the elongate member (2336) is retracted, the delivery system (2300) may produce audible and/or tactile clicks at increments. These clicks may, for example, be due to the ratcheting of the distal end (2342) of the linkage (2348) distally relative to the linear gear (2204). Each click may correspond to a fixed, predetermined volume of fluid, in some cases, about 0.5 µl.

In some variations, the delivery systems may be configured to allow for a fixed cumulative amount of extension and/or retraction of the slidable elongate member. The fixed cumulative amount of extension/retraction may correspond, for example, to the full circumference of Schlemm's canal, two full circumferences of Schlemm's canal, or any desired distance. Exemplary fixed cumulative amounts may be, but are not limited to, about 39 mm to about 41 mm, about 38 mm to about 40 mm, about 35 mm to about 45 mm, about 78 mm to about 82 mm, about 76 mm to about 80 mm, or about 70 mm to about 90 mm. The delivery systems may additionally or alternatively be configured to allow for a fixed cumulative delivery of fluid (e.g., in some variations about 9 µl of fluid). For example, in delivery system (2300), as described above the fluid assembly (2316) may be able to move distally within the housing (2334) but not proximally within the housing, and the fluid assembly may be able to be moved toward but not away from the linear gear (2204). As such, with each extension of the slidable elongate member, the linear gear (2204) and the fluid assembly (2316) may move distally; but with each retraction of the elongate member, the linear gear may move proximally while the fluid assembly remains fixed. The delivery system (2300) may comprise a stop (e.g., a protrusion on the interior wall of the housing) that may prevent the fluid assembly (2316) from moving distally beyond a certain point. Once the fluid assembly (2316) has reached its distal-most position, neither the fluid assembly nor the linear gear (2204) may be moved distally or proximally, and the wheels (2208) may no longer rotate. The distance between the initial position of the fluid assembly (2316) and its final distal-most position may dictate the fixed cumulative amount of extension/retraction of the slidable elongate member and the fixed cumulative delivery of fluid. It should be appreciated, however, that other variations of the delivery systems may not have a limited cumulative amount of extension and/or retraction of the elongate member; that is, some delivery systems may be able to be repeatedly extended and retracted without a fixed limit.

It should be appreciated that the delivery system (2300) may allow the slidable elongate member to be advanced and retracted multiple times, so long as the total, cumulative amount is below the limit. Indeed, in some variations, the maximum amount that the elongate member may be advanced without retraction may be less than that total, cumulative amount. For example, the elongate member may be advanced a first time approximately halfway around Schlemm's canal (i.e., 180 degrees, or approximately 19 mm to about 20 mm) in a first direction, which may be the maximum amount that the elongate member may be advanced without retraction. The elongate member may then be fully retracted (during which fluid may be delivered). After this first extension, the fluid assembly (2316) may have moved half of its maximum distance, and its distance to the linear gear (2204) may have decreased by approximately half of its total possible decrease. The delivery system (2300) may then be rotated about the handle, and the elongate member may be advanced a second time approximately halfway around Schlemm's canal in a second direction. The elongate member may then be retracted (during which fluid may be delivered). At the conclusion of the second extension, the fluid assembly (2316) may be located as its distal-most position, and its distance to the linear gear (2204) may be at its minimum. At this point, the elongate member may no longer be advanced, no further fluid may be deliverable, and the wheels may no longer rotate.

Devices not Configured to Deliver a Fluid

It should be appreciated that not all delivery systems described herein may be configured to deliver a fluid composition. Devices not configured to deliver a fluid composition may operate similarly to delivery systems configured to deliver a fluid composition, but retraction or advancement of the elongate member may not cause simultaneous delivery of a fluid composition. In some instances, the delivery systems may be identical to those configured to deliver a fluid composition, but may not be loaded with fluid composition. In other instances, the elongate member of delivery systems not configured to deliver a fluid composition need not comprise a lumen. Similarly, delivery systems not configured to deliver a fluid composition need not comprise a reservoir or plunger. In place of the reservoir, the delivery system may comprise a solid placeholder component having a similar exterior shape to the fluid assembly. The placeholder component may be connected to the linear gear of the delivery system via a linkage, which may or may not be integral to the placeholder component. This may allow many of the components between delivery systems configured to deliver a fluid composition and not configured to deliver a fluid composition to be interchangeable, which may simplify manufacturing. Thus, like delivery systems configured to deliver a fluid, systems not configured to deliver a fluid may or may not be configured to allow for a fixed cumulative amount of extension and/or retraction, as described in more detail herein.

Some delivery systems not configured to deliver a fluid composition may be configured such that the elongate member disrupts the trabecular meshwork. In some variations, the elongate member may be configured such that advancement and/or retraction of the elongate member may disrupt the trabecular meshwork, and the elongate member may comprise one or more features to promote disruption of the trabecular meshwork upon advancement or retraction, such as disruptive components on the distal end of the elongate member, such as barbs, hooks, balloons, or the like. In other variations, the elongate member may be configured such that the body of the elongate member is configured to cut or tear the trabecular meshwork. For example, the delivery system may be configured such that the elongate member may be advanced out of the cannula and around Schlemm's canal; if the cannula is then removed from the eye without retracting the elongate member, the body of the elongate member may cut or tear the trabecular meshwork as the cannula is removed. The body of the elongate member may be configured to "unzip" the meshwork, cutting or tearing from a first location of the trabecular meshwork close to the cannula tip (i.e., at the proximal end of the elongate member) and continuing around the trabecular meshwork toward the distal end of the elongate member. The elongate member may be configured to apply a disruptive force to cut or tear the meshwork at one location of the meshwork at a time, sequentially around Schlemm's canal, rather than a disruptive force that simultaneously cuts or tears the meshwork throughout all of the trabecular meshwork being cut or torn.

Implanting an Ocular Device

The cannula of the systems described herein may also deliver various surgical tools by ab-interno methods. For example, catheters, wires, probes, and other tools may also be employed ab-interno to access Schlemm's canal and then to create holes, partial thickness disruptions, or perforations in discreet locations or all along the trabecular meshwork or inner wall of Schlemm's canal. The surgeon may also advance the tools all the way across the canal and through the collector channel outer wall to access the sclera and subconjunctival space (again all from an ab-interno approach) to make incisions that create a scleral lake into which aqueous can drain to the scleral veins or subconjunctival space or to deliver an ocular device ab-interno that resides and drains into the scleral lake or sub conjunctival space from the anterior chamber or Schlemm's canal.

When the delivery system is used to implant an ocular device, the cannula may have a slidable positioning element coaxially disposed within the cannula lumen. The slidable positioning elements generally include an engagement mechanism for manipulating, e.g., releasably engaging, advancing and/or retracting, an ocular device. Exemplary engagement mechanisms are depicted in FIGS. 5-9.

Figure 5A:
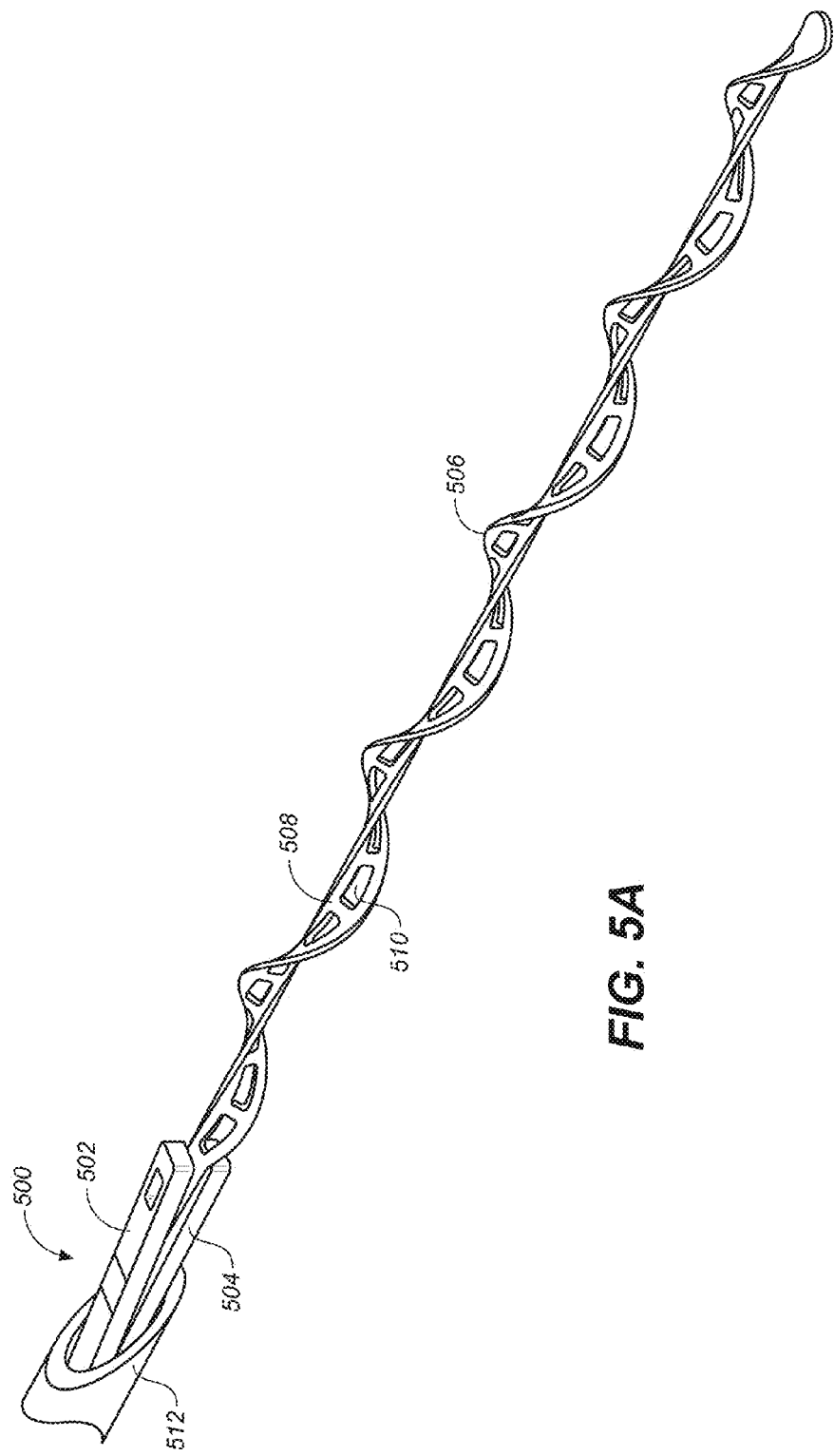
FIGS. 5A-5B show perspective views of an exemplary engagement mechanism for delivery of an illustrative ocular implant.
Figure 5B:
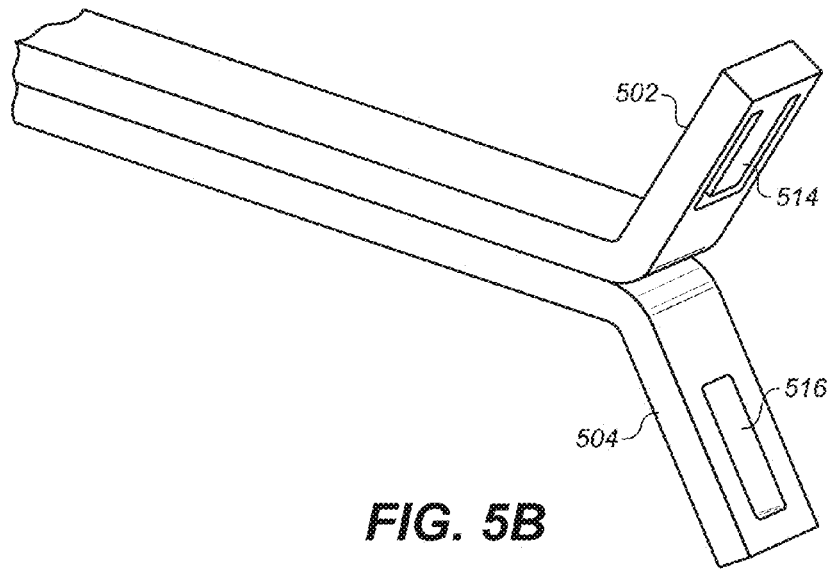
Figure 6:
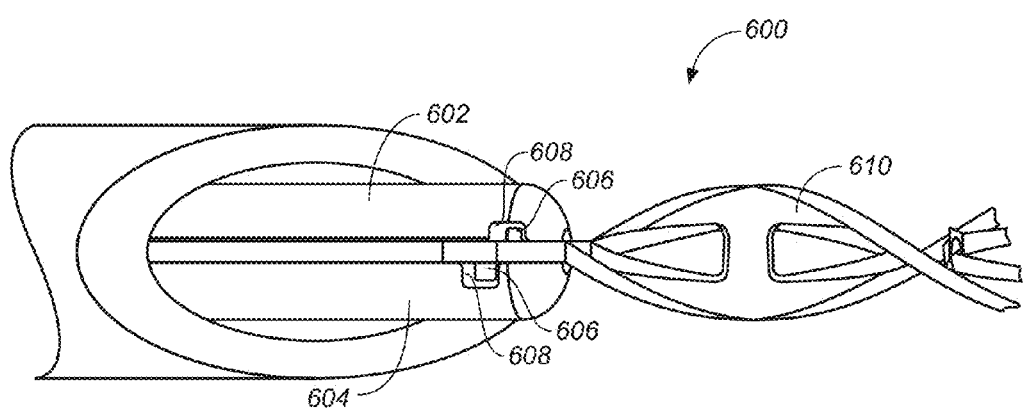
FIG. 6 shows a perspective view of an engagement mechanism for delivery of an illustrative ocular implant according to one variation.

In FIG. 5A, the engagement mechanism (500) comprises a first jaw (502) and a second jaw (504). In their closed configuration (as shown in FIG. 5A), the jaws (502, 504) are constrained within cannula (512) and hold an ocular device (506) comprising a support (508) and at least one fenestration (510). When the jaws (502, 504) are advanced out of cannula (512) they are no longer constrained, and thus take the form of their open configuration, as shown in FIG. 5B. Opening of the jaws (502, 504) releases ocular device (506) from the engagement mechanism (500). At least one tine (514) may be provided in the first jaw (502) and at least one aperture (516) may be provided in the second jaw (504) to help secure a fenestrated ocular device when the jaws are in their closed configuration. In FIG. 6, a variation of an engagement mechanism (600) is shown where a first jaw (602) and a second jaw (604) include both a tine (606) and an aperture (608) to help grasp a fenestrated ocular device (610).

Figure 7A:
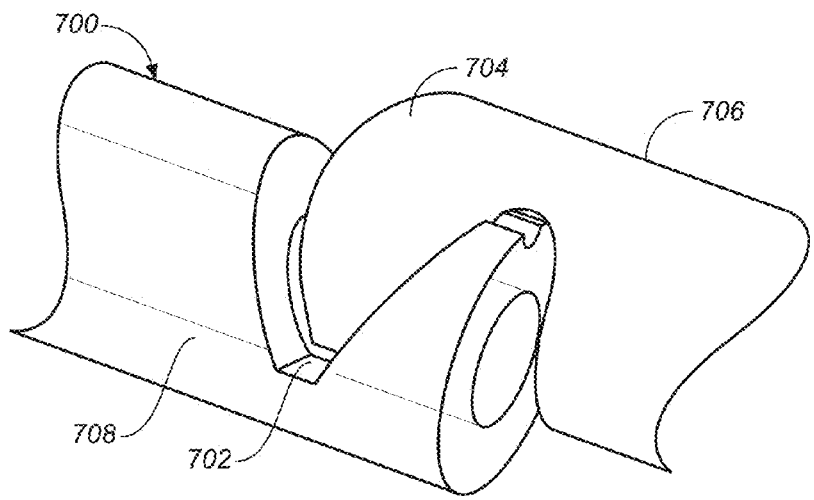
FIGS. 7A-7B show perspective views of engagement mechanisms for delivery of an illustrative ocular implant according to other variations.
Figure 7B:
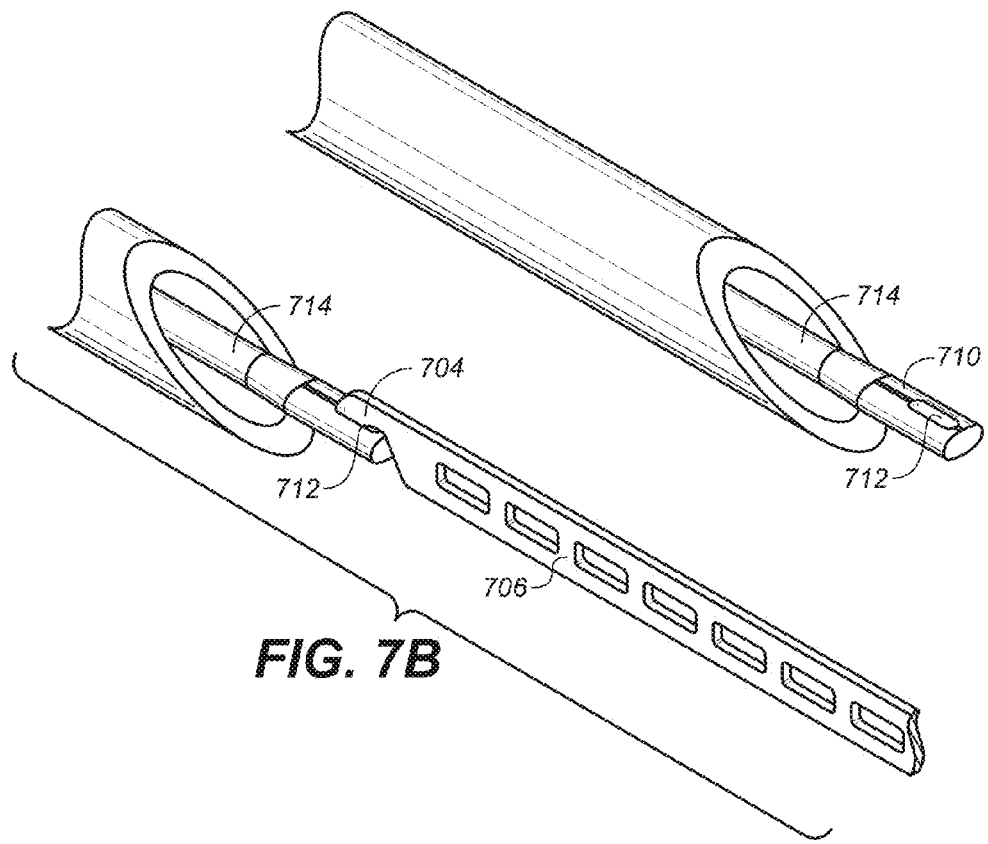

Referring to FIGS. 7A-7B, further exemplary engagement mechanisms are depicted. In FIG. 7A, engagement mechanism (700) comprises complementary mating elements. Specifically, engagement mechanism (700) includes a female element, notch (702) that is configured to interface with a complimentary male element (704), shown as a hook-like projection on the ocular device (706). Here the notch (702) may be fabricated at the end of a hypodermic tube (708) (which would serve as the positioning element). Instead of notch (702), the female element of the engagement mechanism (710) may include an opening (712), as shown FIG. 7B, which interfaces with male element (704) on the ocular device (706). In FIG. 7B, the positioning element (714) may be fabricated from a metal wire or rod and the opening (712) created via laser machining or other processes known in the art.

Figure 8A:
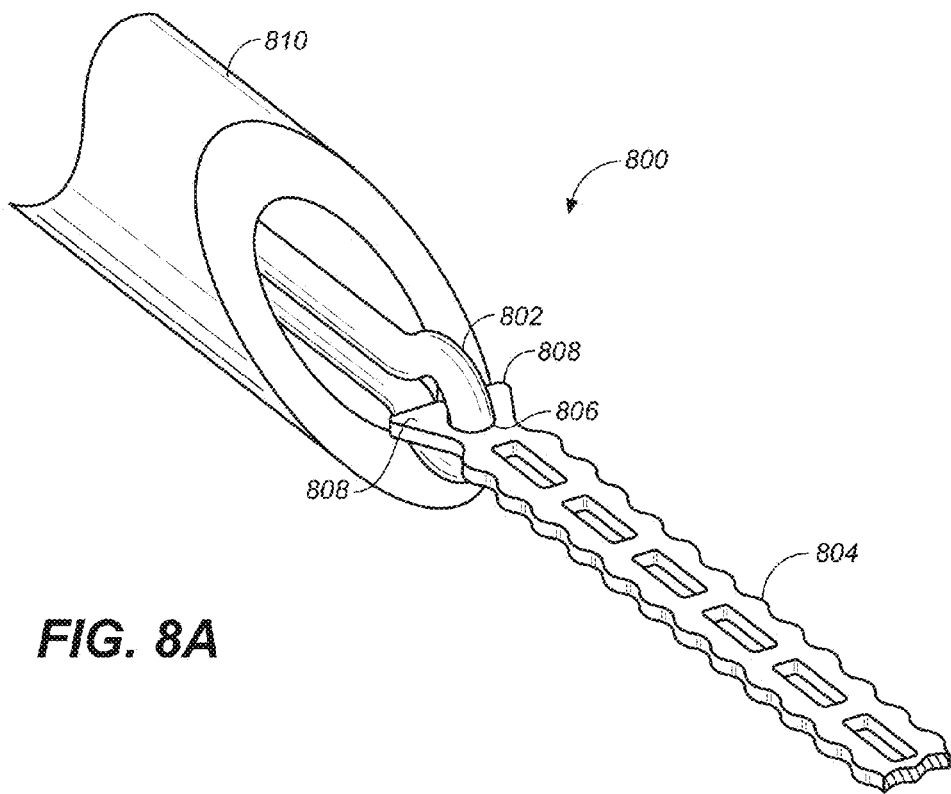
FIG. 8A-8B depict perspective views of an engagement mechanism for delivery of an illustrative ocular implant according to yet a further variation.
Figure 8B:
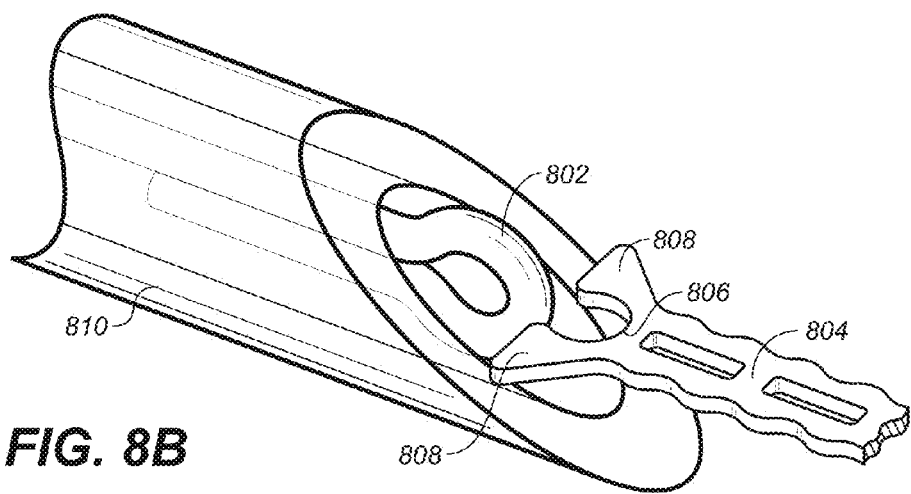

In other variations, the engagement mechanism may be configured as shown in FIGS. 8A and 8B. In those figures, engagement mechanism (800) comprises a looped portion (802). It may be beneficial to use this particular engagement mechanism with an ocular device (804) including a clasp (806) with arms or tabs (808) having a closed configuration and an expanded configuration. Similar to the variation shown in FIGS. 5A and 5B, tabs (808) are constrained in their closed configuration within the cannula (810) prior to advancement out of the cannula (810). In their constrained configuration, tabs (808) engage the looped portion (802) of the engagement mechanism (800) to prevent release of the ocular device (804) from the system. When the looped portion (802) of the engagement mechanism (800) is advanced sufficiently so that tabs (808) are no longer constrained by cannula (810), tabs (808) take on their expanded configuration to thus release the ocular device (804) from the looped portion (802) and into Schlemm's canal, as shown in FIG. 8B.

Figure 9:
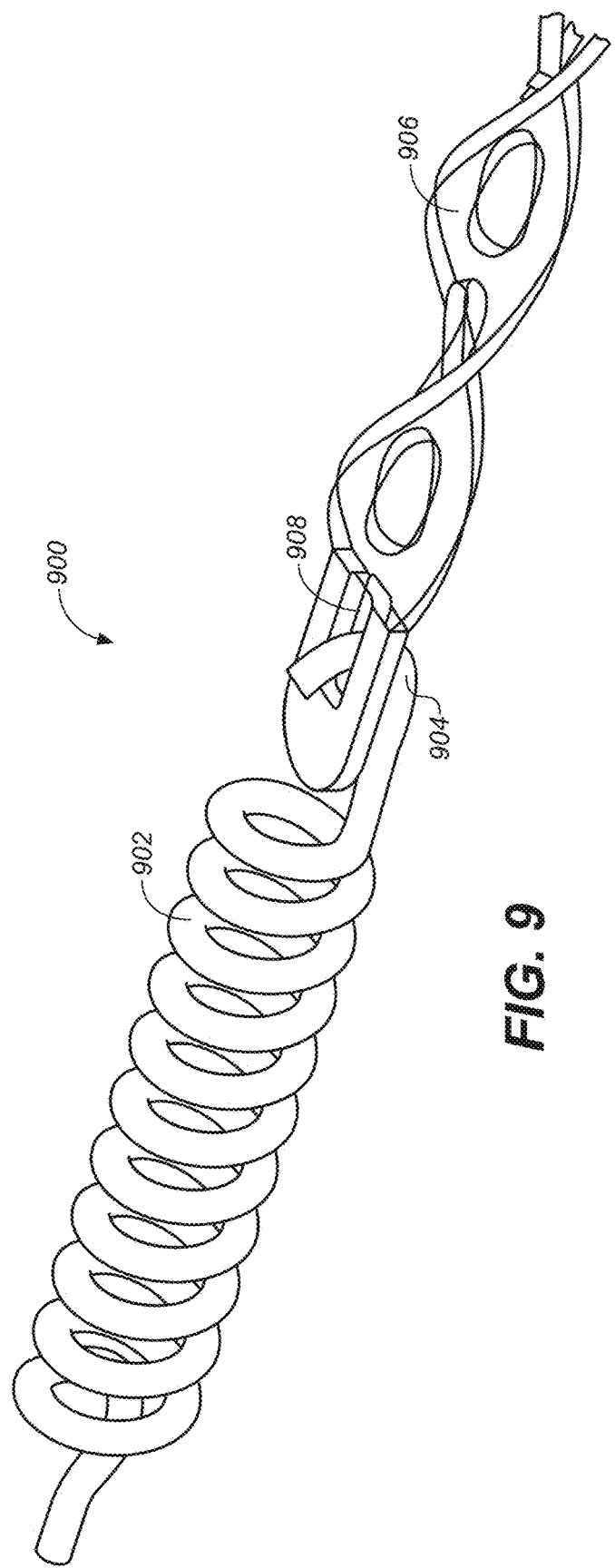
FIG. 9 depicts a perspective view of another exemplary engagement mechanism for delivery of an illustrative ocular implant.

Another exemplary engagement mechanism (900) is shown in FIG. 9 comprising a coiled portion (902) and a hook (904). When an ocular device (906) having at least one fenestration (908) (e.g., a proximal fenestration) is to be implanted, the hook (904) may be releasably engaged to the fenestration (908). The ocular device (906) may be disengaged from the hook by the application of gentle force on the coil (902) or by another component (not shown) that can be advanced over the coil (902) to push the device (906) off the hook (904). It may be advantageous to use the hook (904) when retraction of the ocular device (906) is desired.

The ocular delivery systems may further include a slidable positioning element coaxially disposed within the lumen of the cannula for controlled implantation of an ocular device within Schlemm's canal. The positioning element generally comprises a proximal end, a distal end, and an engagement mechanism at the distal end. The ocular device is generally releasably coupled to the engagement mechanism. The positioning element may be advanced to deploy an ocular device within the cannula into Schlemm's canal, or it may be retracted to help with positioning and/or repositioning of an ocular device, or disengagement of an ocular device from the engagement mechanism.

Some variations of the engagement mechanism include a proximal coiled portion and a distal hook. When an implant having at least one fenestration (e.g., a proximal fenestration) is to be implanted, the hook may be releasably engaged to the fenestration. The ocular device may be disengaged from the hook by the application of gentle force on the coil or by another component that can be advanced over the coil to push the device off the hook or by using shape memory materials that passively disengages when exiting the cannula. It may be advantageous to use the hook when retraction of the ocular device is desired. The surgeon may simply move the delivery system and engagement mechanism so that it disengages any fenestration or notch on the implant.

In another variation, the engagement mechanism includes opposing jaws. Here the engagement mechanism may include a first jaw and a second jaw, where the jaws have a closed configuration and an open configuration. The jaws may be used to grip and manipulate the ocular device, and releasably couple the ocular device to the positioning element. The jaws may be formed by splitting or bifurcating the distal end of a wire, e.g., by laser cutting. The grasping force of the jaws may be achieved by constraining the jaws within the cannula. The ocular device may be released once the jaws are advanced out of the cannula and expand. The jaws may also be pivotably connected. In yet another variation, the first jaw may include at least one tine, and the second jaw may include at least one aperture for receiving the tine when the jaws are in the closed configuration.

In further variations, the engagement mechanism comprises a looped portion. This variation of the engagement mechanism will typically be used with an ocular device comprising a spring-like clasp at its proximal end, where the clasp has a collapsed configuration and an expanded configuration. The clasp is generally fabricated in the expanded position. Thus, when a device having a clasp is disposed within the cannula, the first and second arms or tabs of the clasp may collapse around the looped portion of the engagement mechanism. Once the clasped portion of the device has exited the cannula, the arms or tabs may expand to release the ocular device from the looped portion.

Still another variation of the engagement mechanism includes a female to male interface. For example, the engagement mechanism may comprise a notch configured to interface with a complimentary mating element (e.g., a tab) on the ocular device. The notch (female component) may be formed within hypodermic tubing or may be made by creating a fenestration through the distal end of a positioning element made from a solid wire or element, and the tab or hook (male component) may formed as part of the ocular device and may be inserted into the fenestration or notch in the positioning element. With this configuration, the ocular device may be released from the positioning element as it is advanced out of the cannula either by the surgeon's manipulation or by shape setting of the positioning element that causes it to passively detach from the ocular device or both.

II. Kits

The delivery systems described herein may be placed in specialized packaging. The packaging may be designed to protect the systems, and in particular, to protect the cannula. It may be desirable for the packaging to prevent contact between the distal tip of the cannula and any other object or surface. In order to do so, the packaging may comprise one or more elements configured to secure a delivery system to the packaging at one or more locations proximal to the distal tip of the cannula. Securing the delivery system at at least two locations proximal to the distal tip of the cannula may be desirable to limit the ability of the delivery system to pivot relative to the packaging.

Figure 26A:
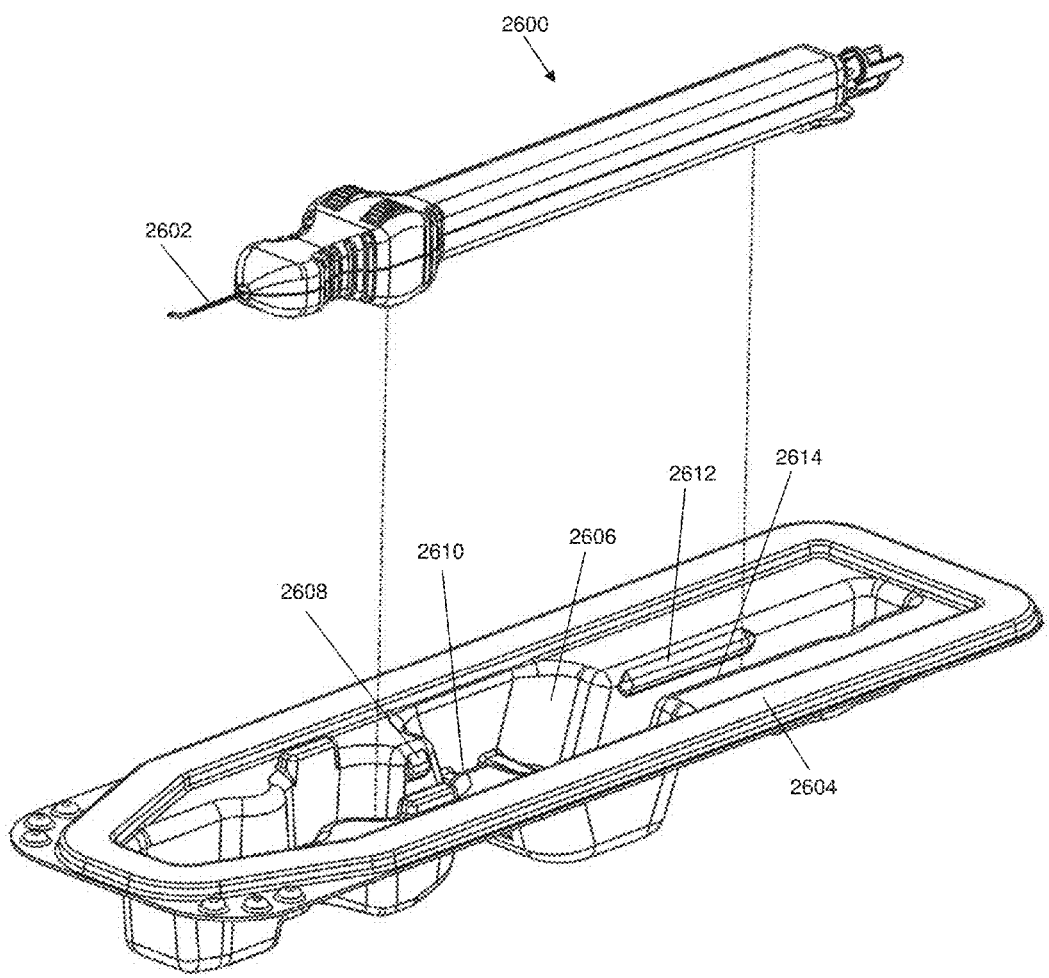
FIGS. 26A-26B show perspective views of an exemplary tray for a delivery system with a delivery system (FIG. 26A) and with a delivery system and loading tool (FIG. 26B).
Figure 26B:
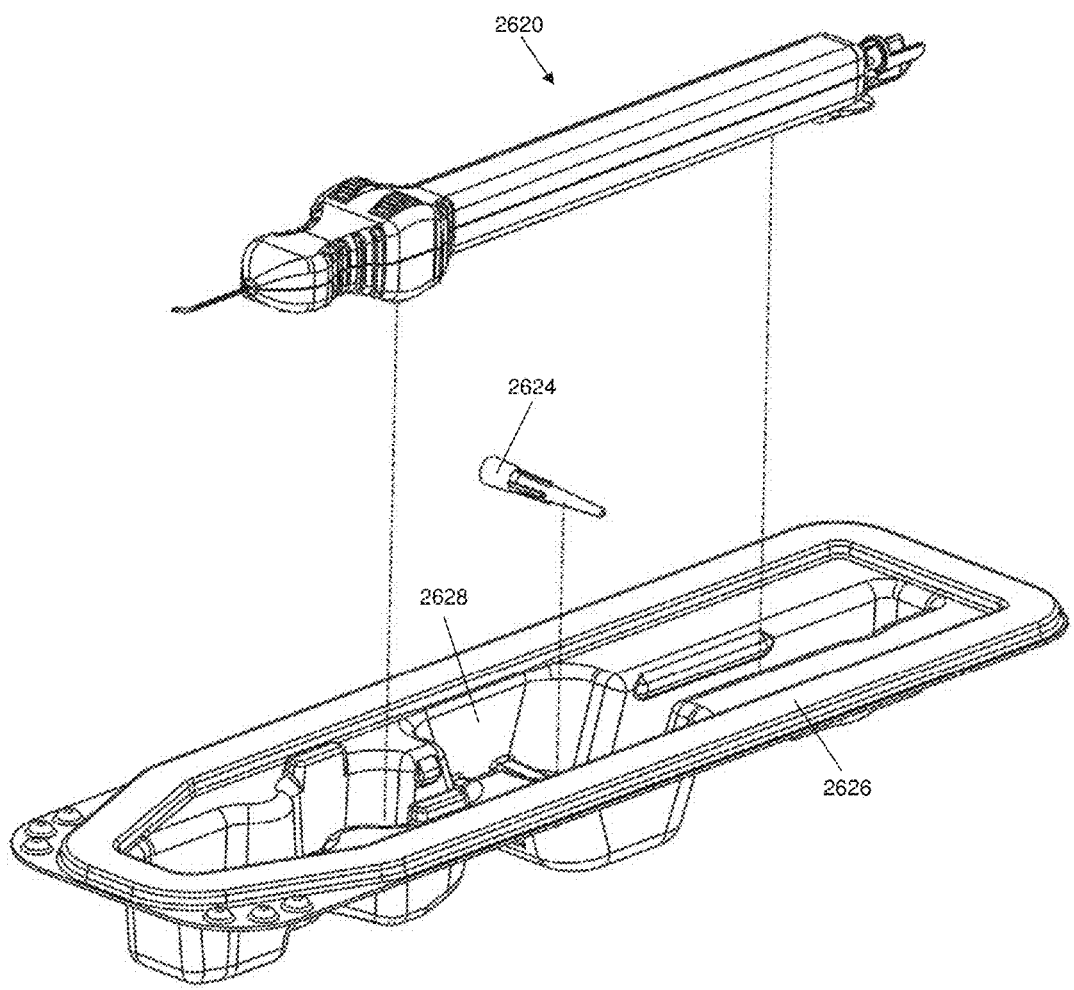
Figure 26C:
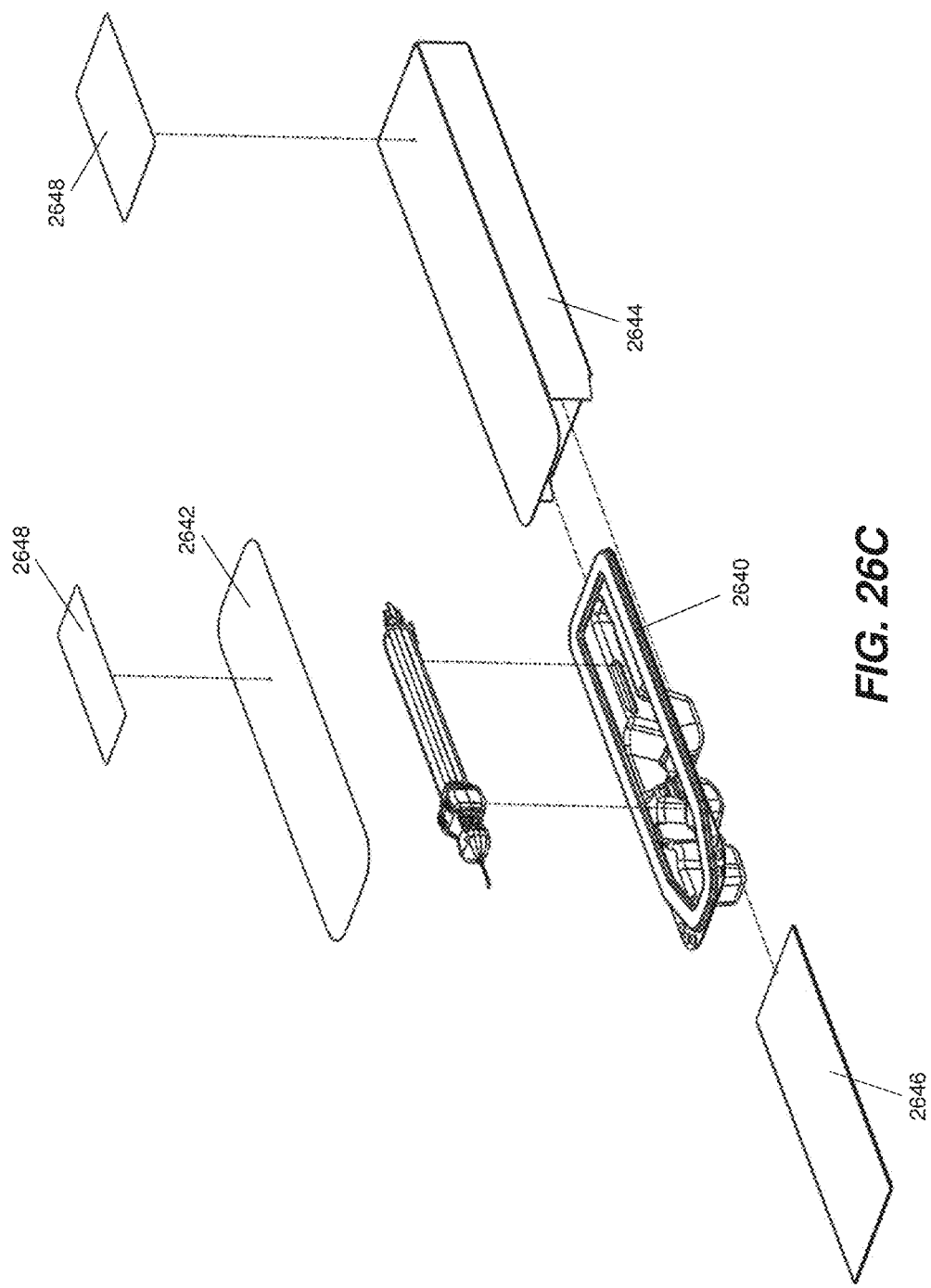
FIG. 26C shows an exploded view of an exemplary packaged kit.

In one exemplary variation, the packaging may comprise a tray comprising a recess having a shape generally corresponding to the shape of the delivery system and comprising one or more pinch points configured to secure the delivery system at locations proximal to the cannula. FIG. 26A shows an exemplary tray (2604) for a delivery system (2600). Tray (2604) may comprise a recess (2606) configured to receive the delivery system (2600). The tray (2604) may comprise first (2608) and second (2610) distal pinch points and first (2612) and second (2614) proximal pinch points configured to secure the delivery system (2600) within the recess (2606). When the delivery system (2600) is secured within the tray (2604), the cannula (2602) of the delivery system may be suspended such that the cannula is not in contact with the tray, and the pinch points may limit pivoting of the delivery system (2600) in a way that could cause the cannula (2602) to come into contact with the tray. The pinch points may be configured to safely secure the delivery system (2600) within the tray (2604), while also allowing a user to remove the delivery system from the tray in a controlled fashion. In variations in which the kits described here comprise additional components, the packaging may be designed to hold these additional components. For example, FIG. 26B shows an exemplary tray (2626) comprising a recess (2628) configured to hold a loading tool (2624) and a delivery system (2620). As shown in FIG. 26C, a tray (2640) may be configured to be sealed with a lid (2642) (e.g., heat sealed) and placed within a box (2644). The box (2644) may optionally further contain instructions for use (2646). The lid (2642) and/or box (2644) may optionally have labels (2648) affixed thereto.

It should be appreciated that the packaging may have other configurations that protect the distal tip of the cannula. For example, in another variation, the packaging may comprise a stiff planar sheet to which the delivery system may be attached in an orientation such that the cannula is not in contact with the planar sheet. The delivery system may be attached (e.g., via ties or other materials wrapped around the housing) at two or more points along the housing in order to prevent movement of the delivery system relative to the planar sheet. It may be desirable to protect the cannula on at least two sides; for example, a portion of the planar sheet near the cannula may be bent around the cannula to protect the cannula on at least two sides, or a second stiff planar sheet may be attached to the delivery system opposite the first planar sheet.

Figure 27A:
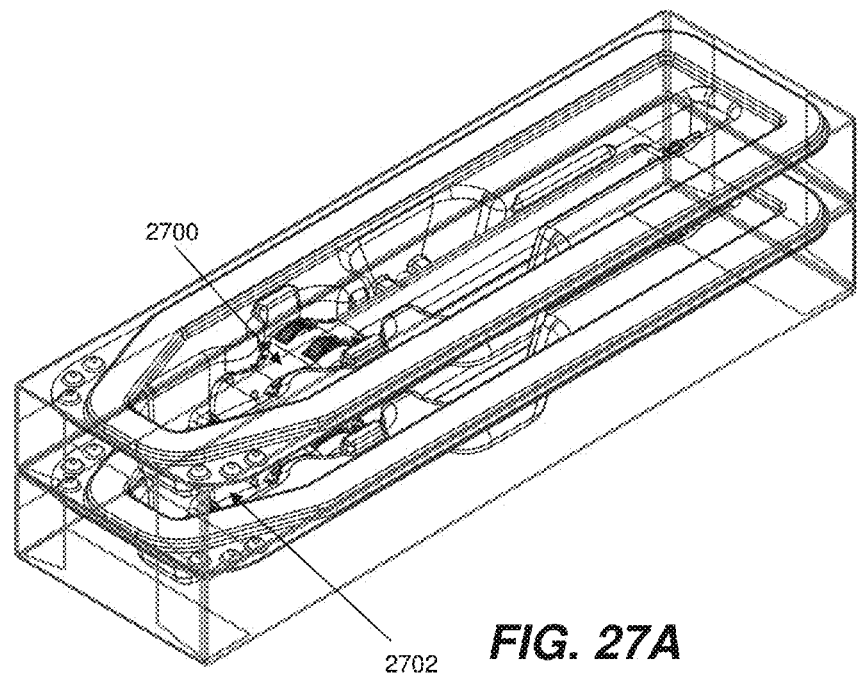
FIGS. 27A-27B show exemplary kits comprising multiple delivery systems.
Figure 27B:
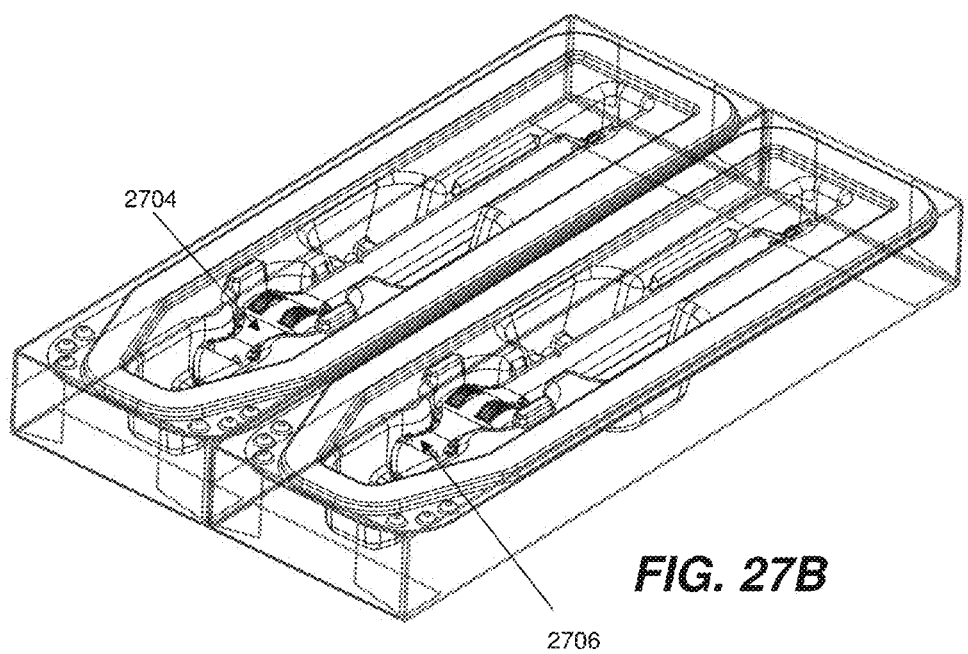

Some kits described herein may comprise multiple delivery systems. For example, a kit may comprise two delivery systems. In some variations, the kit may comprise two of the same system, such that, for example, the first delivery system may be used in a first eye of the patient and the second delivery system may be used in the second eye of the patient. In other variations, the kit may comprise two different systems. For instance, the first delivery system may be configured to deliver a fluid composition, and the second delivery system may not be configured to deliver a fluid composition, but may instead be configured to disrupt the trabecular meshwork using the elongate member. Kits comprising multiple systems may be packaged in any suitable way. For example, FIG. 27A shows a kit comprising two delivery systems (2700, 2702) in a stacked configuration (shown without outer packaging), and FIG. 27B shows a kit comprising two delivery systems (2704, 2706) in a side-by-side configuration (shown without outer packaging). Again, delivery systems (2700, 2702) may both be configured to deliver a fluid composition, may both be configured not to deliver a fluid composition (e.g., may be configured to deliver an elongate member to disrupt the trabecular meshwork), or one may be configured to deliver a fluid composition and the other may not. Similarly, delivery systems (2704, 2706) may both be configured to deliver a fluid composition, may both be configured not to deliver a fluid composition, or one may be configured to deliver a fluid composition and the other may not.

Some kits may comprise ocular implants in addition to one or more delivery systems as described herein. For example, a kit may comprise one or more devices configured to be implanted into Schlemm's canal, which may be generally configured to maintain the patency of Schlemm's canal without substantially interfering with transmural fluid flow across the canal. The kits may comprise one or more ocular implants such as, but not limited to, stents for placement in Schlemm's canal. In some variations, the ocular implants may be one or more of those disclosed in U.S. Pat. No. 7,909,789, which was previously incorporated by reference in its entirety, and U.S. Pat. No. 8,529,622, which was previously incorporated by reference in its entirety. In one variation, the device may comprise a twisted ribbon member comprising a double helix comprising a first elongated edge and a second elongated edge and a plurality of struts extending between the elongated edges in a direction substantially normal to a central longitudinal axis of the twisted ribbon member. The struts may define a plurality of fenestrations spaced along at least a portion of the length of the twisted ribbon member.

III. Methods

Methods for treating conditions of the eye and/or methods for implanting an ocular device, delivering a fluid composition into Schlemm's canal, and/or delivering a tool into Schlemm's canal using the systems described above are also provided. In some instances, treating conditions of the eye may result in increased aqueous humor drainage, reduced resistance to aqueous outflow, and/or reduced intraocular pressure. Some methods described herein may dilate Schlemm's canal, dilate the collector channels, and/or break any septae that may obstruct circumferential flow through Schlemm's canal. Dilation of Schlemm's canal may disrupt obstructed inner walls of the canal, stretch the trabecular meshwork, and/or increase the trabecular meshwork's porosity. This may improve the natural aqueous outflow pathway. The dilation may be performed by advancement of a tool (e.g., a slidable elongate member as described herein). Additionally or alternatively, the dilation may be performed by delivery of a fluid composition (e.g., a viscoelastic fluid as described herein). Additionally or alternatively, some methods described here may comprise performing a trabeculotomy to cut trabecular meshwork. Additionally or alternatively, some methods described here may comprise implanting an ocular device within Schlemm's canal. In some instances, the systems described herein may be used in performing ab-interno trabeculotomy, ab-interno transluminal trabeculotomy, clear corneal trabeculotomy, clear corneal transluminal trabeculotomy, ab-interno canaloplasty, and/or clear corneal canaloplasty. The delivery systems may also in some instances be used for lysing of anterior chamber synechiae, viscogonioplasty, assisting with intraocular lens exchange, levitating a dropped lens or foreign body, and/or repositioning of prolapsed iris tissue.

The methods are generally single-handed, single-operator controlled methods that are minimally invasive, e.g., they are tailored for an ab-interno procedure, which as previously mentioned, can be advantageous over the more invasive ab-externo approach. However, use of the ocular systems in an ab-externo method may be contemplated in some instances and thus, are not excluded here. The methods for delivering an ocular device or fluid, or for providing a disruptive force, may be used to treat or prevent glaucoma, pre-glaucoma, or ocular hypertension. When treating glaucoma, the methods may also be used in conjunction with a cataract surgery (before or after) using the same incision during the same session or at another time.

Some of the methods, described in more detail below, may comprise dilating Schlemm's canal and/or aqueous collector channels (e.g., with viscoelastic fluid) using the delivery systems described herein. Others of the methods, also described in more detail below, may comprise tearing or cutting the trabecular meshwork of Schlemm's canal. These methods may be carried out separately, or they may be combined into a single procedure. For example, in some instances a portion (e.g., half) of Schlemm's canal may be dilated (either using a fluid composition or a tool, or both, for example), and the trabecular meshwork of the same or a different portion of Schlemm's canal may be torn or cut, within the same eye. As another example, all of Schlemm's canal may be dilated, and then all or a portion of the trabecular meshwork may subsequently be torn or cut. This may be desirable, for example, in order to both dilate the collector channels and tear or cut the trabecular meshwork.

In some of these variations, dilation and tearing or cutting may be performed using a single delivery system, such as one described herein configured to deliver a fluid composition. For example, the elongate member of a delivery system configured to deliver a fluid composition may first be used to deliver a fluid composition to a portion of Schlemm's canal (e.g., about an 180 degree arc of the canal, about a 90 degree arc of the canal) as described herein, and subsequently to tear or cut the trabecular meshwork in the same portion of the canal as described herein. As another example, the elongate member of a delivery system configured to deliver a fluid composition may first be used to deliver a fluid composition to a portion of Schlemm's canal (e.g., about an 180 degree arc of the canal, about a 90 degree arc of the canal, etc.) and subsequently to tear or cut the trabecular meshwork in another portion of the canal (e.g., the other about-180 degree arc, another 90 degree arc, etc.). As yet another example, the elongate member of a delivery system configured to deliver a fluid composition may first be used to deliver fluid composition to all of Schlemm's canal (e.g., by delivering about 180 degrees of fluid composition in a first direction and then delivering about 180 degrees of fluid composition in a second direction), and then subsequently to tear or cut the full 360 degrees of trabecular meshwork (e.g., by tearing or cutting about 180 degrees of trabecular meshwork in a first direction and then tearing or cutting about 180 degrees of trabecular meshwork in a second direction).

In other variations, dilation and tearing or cutting may be performed using different delivery systems (e.g., the dilation may be performed using a delivery system configured to deliver a fluid composition, and the tearing or cutting may be performed using a delivery system not configured to deliver a fluid). As yet another example, in some instances dilation may be performed in one eye of a patient, while the trabecular meshwork is torn or cut in the other eye of the patient.

Procedures dilating Schlemm's canal and/or tearing or cutting the trabecular meshwork may also be combined with procedures delivering an ocular device (described in more detail herein), either in the same eye or in different eyes of the same patient. For example, all or a portion of Schlemm's canal may be dilated, followed by insertion of an ocular device. As another example, a portion of the trabecular meshwork may be torn or cut, while an ocular implant may be delivered to another portion of Schlemm's canal. As yet another example, a portion of Schlemm's canal may be dilated, while an ocular implant may be delivered to another portion of Schlemm's canal. As yet another example, an ocular implant may be delivered to a portion of Schlemm's canal, and then Schlemm's canal may be subsequently dilated to improve the function of the ocular implant.

Ocular Device Delivery

In general, the methods for implanting an ocular device within Schlemm's canal first include the step of creating an incision in the ocular wall (e.g., the sclera or cornea or corneoscleral limbus or junction) that provides access to the anterior chamber of the eye. As shown in the stylized depiction of an eye in FIG. 14, the cannula (1400) of the ocular delivery system is then advanced through the incision and at least partially across the anterior chamber (1402) to the trabecular meshwork (not shown). Schlemm's canal (i.e., the lumen of Schlemm's canal) (1404) is then accessed with the distal curved portion of the cannula (1406) and a slidable positioning element, (or, e.g., a slidable tool or guidewire), or elongate member (represented generically by element 1408) is advanced from the cannula to implant an ocular device within Schlemm's canal, perform a procedure within Schlemm's canal or on any of the neighboring trabeculocanalicular tissues, or deliver a fluid into the canal. However, in some instances, a elongate member may not be employed so that any fluid to be delivered is delivered through the cannula. In yet further variations, just the trabecular meshwork is punctured and the fluid composition is delivered without circumnavigation of Schlemm's canal.

As previously stated, in some variations the cannula may be configured to include a proximal end and a distal curved portion, where the distal curved portion has a proximal end, a distal end, and a radius of curvature defined between the ends. Here the cannula may also include a body and a distal tip having a bevel that directly engages the radius of curvature, e.g., it is contiguous with the radius of curvature. In other variations, Schlemm's canal may be accessed with a straight cannula (i.e., one not having a distal curved portion). The method may also include the step of flushing the system with fluid (e.g., to remove air from the system) and/or the step of irrigating the operative field to clear away blood or otherwise improve visualization of the field.

Any suitable ocular device that maintains the patency of Schlemm's canal or improves outflow of aqueous humor may be implanted by the systems described herein. For example, ocular devices that maintain the patency of Schlemm's canal without substantially interfering with fluid flow across, along, or out of the canal may be implanted. Such devices may comprise a support having at least one fenestration, as disclosed in U.S. Pat. Nos. 7,909,789, and 8,529,622, which were previously incorporated by reference in their entirety. Ocular devices that disrupt the juxtacanalicular trabecular meshwork or adjacent inner wall of Schlemm's canal may also be implanted. In addition to ocular devices made from metal or metal alloys, the use of sutures, modified sutures, modified polymers, polymeric filaments, or solid viscoelastic structures may be delivered. Fluid compositions such as saline, viscoelastic fluids, air, drug mixtures or solutions, and gas may also be delivered.

When a fluid composition is delivered into Schlemm's canal, the methods generally include the steps of creating an incision in the ocular wall (e.g., the sclera or cornea) that provides access to the anterior chamber of the eye; advancing a cannula of the ocular delivery system through the incision and at least partially across the anterior chamber to the trabecular meshwork; accessing Schlemm's canal with the cannula; and delivering the fluid composition into the canal using a elongate member slidable within the cannula lumen. The cannula may be configured to include a proximal end and a distal curved portion, where the distal curved portion has a proximal end, a distal end, and a radius of curvature defined between the ends. Here the cannula may also include a body and a distal tip having a bevel that directly engages the radius of curvature, e.g., it is contiguous with the radius of curvature. Further advantageous cannula features may also be included, which are described above. The method may also include the step of flushing the system with fluid (e.g., to remove air from the system) and/or the step of irrigating the operative field to clear away blood or otherwise improve visualization of the field.

When an ab-interno method is employed for implanting an ocular device, the method may include the following steps. The surgeon may first view the anterior chamber and trabecular meshwork (with underlying Schlemm's canal) using an operating microscope and a gonioscope or gonioprism. Using a 0.5 mm or greater corneal, limbal, or sclera incision, the surgeon may then gain access to the anterior chamber. A saline solution or viscoelastic composition may then be introduced into the anterior chamber to prevent its collapse. Here the saline solution or viscoelastic composition may be delivered through the delivery system cannula or by another mode, e.g., by infusion through an irrigating sleeve on the cannula. The surgeon, under direct microscopic visualization, may then advance the cannula of the delivery system through the incision towards the anterior chamber angle. When nearing the angle (and thus the trabecular meshwork), the surgeon may apply a gonioscope or gonioprism to the cornea to visualize the angle. The application of a fluid (e.g., a viscous solution or a viscoelastic composition as previously described) to the cornea and/or gonioscope or gonioprism may help to achieve good optical contact and negate total internal reflection thereby allowing visualization of the anterior chamber angle. As the surgeon visualizes the trabecular meshwork, the cannula may then be advanced so that the bevel of at the distal end of the curved distal portion of the cannula pierces the meshwork and is in communication with the lumen of Schlemm's canal. The surgeon may irrigate saline or a viscoelastic composition into the canal or into the anterior chamber to either prevent collapse of chamber, dilate Schlemm's canal, or wash away any blood that may obscure visualization of cannula and ocular device delivery. Next, when the ocular device is advanced to the extent desired by the surgeon, it is released from the engagement mechanism so that it can reside in Schlemm's canal. If repositioning of the ocular device is needed or desired, the surgeon may retract and/or reposition the ocular device using the positioning element of the delivery system. The surgeon may then withdraw the delivery system from the eye.

Other variations of the ab-interno method for implanting an ocular device include the use of an endoscope. Similar to the method above, access to the anterior chamber is first made by incising the cornea, limbus, or sclera. Again, this may be done in combination with cataract surgery in one sitting, either before or after cataract surgery, or independently. The anterior chamber may be infused with saline solution or a viscoelastic composition may be placed in the anterior chamber to prevent its collapse. The saline or viscoelastic may be delivered as a separate step or it may be infused with the elongate member of the delivery system, an irrigating sleeve on the elongate member or cannula, or with a separate infusion cannula. The surgeon, under direct microscopic visualization, then advances the endoscope through the incision and towards the angle and trabecular meshwork. As the surgeon visualizes the trabecular meshwork using the endoscope or any associated video display, the bevel of the cannula is advanced to pierce the meshwork. The ocular device is then advanced using the positioning element under endoscopic visualization. The surgeon may irrigate saline or a viscoelastic composition into the canal or into the anterior chamber to either prevent collapse of chamber, dilate Schlemm's canal, or wash away any blood that may obscure visualization of cannula and ocular device delivery. When the ocular device is advanced to the extent desired by the surgeon, it is released from the engagement mechanism so that it can reside in Schlemm's canal. If repositioning of the ocular device is needed or desired, the surgeon may retract and/or advance the ocular device using the positioning element of the delivery system. The surgeon may then withdraw the delivery system from the eye.

Fluid Composition Delivery

Some methods described herein may comprise delivering fluid composition into the eye, such as into Schlemm's canal. In some methods, an elongate member comprising a lumen may be advanced into Schlemm's canal and the fluid composition may be delivered via the elongate member. Both the elongate member and fluid delivery may dilate Schlemm's canal, and fluid delivery may additionally dilate the collector channels. With respect to the delivery of a fluid composition, the methods are similar to the implantation of an ocular device. However, instead of using a positioning element, the delivery system may employ a slidable elongate member to infuse a fluid composition into Schlemm's canal.

The fluid compositions may be delivered to dilate Schlemm's canal. The entire length of Schlemm's canal or a portion thereof may be dilated by the fluid. For example, at least 75%, at least 50%, at least 25%, at least 10% of the canal, or at least 1% of the canal may be dilated. The fluid compositions may also be delivered to treat various medical conditions of the eye, including but not limited to, glaucoma, pre-glaucoma, anterior or posterior segment neovascularization diseases, anterior or posterior segment inflammatory diseases, ocular hypertension, uveitis, age-related macular degeneration, diabetic retinopathy, genetic eye disorders, complications of cataract surgery, vascular occlusions, vascular disease, or inflammatory disease.

The surgeon may first view the anterior chamber and trabecular meshwork (with underlying Schlemm's canal) using an operating microscope and a gonioscope or gonioprism. Using a 0.5 mm or greater corneal, limbal, or sclera incision, the surgeon may then gain access to the anterior chamber. A saline solution or viscoelastic composition may then be introduced into the anterior chamber to prevent its collapse. Here the saline solution or viscoelastic composition may be delivered through the delivery system cannula or by another mode, e.g., by infusion through an irrigating sleeve on the cannula. The surgeon, under direct microscopic visualization, may then advance the cannula of the delivery system through the incision towards the anterior chamber angle. When nearing the angle (and thus the trabecular meshwork), the surgeon may apply a gonioscope or gonioprism to the cornea to visualize the angle. The application of a viscous fluid (e.g., a viscoelastic composition as previously described) to the cornea and/or gonioscope or gonioprism may help to achieve good optical contact and negate total internal reflection thereby allowing visualization of the anterior chamber angle. As the surgeon visualizes the trabecular meshwork, the cannula may then be advanced so that the bevel of at the distal end of the curved distal portion of the cannula pierces the meshwork and is in communication with the lumen of Schlemm's canal.

Next, a slidable elongate member coaxially disposed within the cannula lumen may be advanced into the canal under gonioscopic visualization. The elongate member may be advanced any suitable amount and direction about the canal. For example, the elongate member may be advanced between about 1 degree and about 360 degrees about the canal, between about 10 degrees and about 360 degrees about the canal, between about 150 and about 210 degrees about the canal, or any suitable distance, about 360 degrees about the canal, about 270 degrees about the canal, about 180 degrees about the canal, about 120 degrees about the canal, about 90 degrees about the canal, about 60 degrees about the canal, about 30 degrees about the canal, or about 5 degrees about the canal. In some variations, the elongate member may be advanced in two steps, e.g., first in a clockwise direction (e.g., about 180 degrees, about 90 degrees, etc.) and second in a counterclockwise direction (e.g., about 180 degrees, about 90 degrees, etc.) about the canal (e.g., to thereby achieve a 360 or 180 degree ab-interno viscocanalostomy or canaloplasty). Fluid may be injected upon advancement or retraction of the elongate member. Once the slidable elongate member has been positioned within the canal, a fluid composition, e.g., a viscoelastic solution, may be continuously or intermittently delivered through the lumen of the elongate member. The fluid composition may exit the lumen of the elongate member through its distal end (e.g., the through the distal tip), or through openings or fenestrations provided along its shaft, or a combination of both. The openings or fenestrations may be spaced along the axial length of the elongate member in any suitable manner, e.g., symmetrically or asymmetrically along its length. Other substances such as drugs, air, or gas may delivered be in the same manner if desired.

In some variations, the slidable elongate member may be repositioned by retraction or repeated advancement and retraction. In some variations of the method, the same or different incision may be used, but the delivery system cannula is employed to access and dilate Schlemm's canal from a different direction (e.g., counterclockwise instead of clockwise). Once a sufficient amount of fluid has been delivered, the surgeon may retract the slidable elongate member into the cannula and remove the delivery system from the eye. It should be appreciated that the cannulas described here may be specifically manufactured to comprise a dual-surface configuration at the distal tip (i.e., sharp and smooth surfaces), which may allow the elongate member to be advanced, repositioned, and/or retracted without severing it on the distal tip of the cannula. It should also be understood that these steps may be used alone or in combination with cataract surgery (in one sitting).

Some of the delivery systems described herein may be configured such that the cumulative amount of advancement and/or retraction of the slidable elongate member is limited. For example, as described above, after the elongate member is advanced and retracted a particular cumulative distance (e.g., about 39 mm to about 40 mm each of advancement and retraction, corresponding to the approximate circumference of Schlemm's canal; or about 78 mm to about 80 mm each of advancement and retraction, corresponding to approximately twice the circumference of Schlemm's canal; or any other suitable distance), it may no longer be able to be advanced. This advancement and retraction may occur over multiple advancement-retraction cycles. For example, the elongate member may be advanced about 20 mm, then retracted by about 20 mm, then advanced by about 20 mm, then retracted by about 20 mm. When the cumulative distance is limited to about 40 mm, after these two cycles of advancement and retraction, the elongate member may no longer be able to be advanced.

In some variations of the ab-interno method, the fluid composition may be delivered simultaneously with retraction of the elongate member (i.e., the fluid compositions may be delivered in a manner where retraction of a system component allows advancement of the fluid out of the system cannula). Referring again to FIGS. 11A-11C, linear gear (1108) is retracted in the direction of the arrow (FIG. 11B) so that reservoir (1102) becomes pressurized. Retraction can be accomplished by rotation of pinion gear mechanisms (1120). Once a sufficient amount of pressure has been created in the reservoir (1102) the fluid composition contained therein is injected through linear gear lumen (1114) and elongate member (1118) into Schlemm's canal. It should be understood that the ocular delivery systems may be configured so that the fluid compositions are delivered continuously, passively, automatically, or actively by the surgeon. The fluid compositions may also be delivered to the canal independent of the gear shaft movement with a pump or auxiliary plunger. In some variations, retraction of the elongate member may correspond to a fixed volume of fluid composition being delivered via the lumen of the elongate member. The fluid composition may be delivered via the distal opening of the lumen of the elongate member as it is retracted, and thus, the fluid may be evenly delivered throughout the portion of the canal through which the elongate member was advanced.

The fluid compositions that may be delivered by the ocular systems described herein include but are not limited to saline and viscoelastic fluids. The viscoelastic fluids may comprise hyaluronic acid, chondroitin sulfate, cellulose, derivatives or mixtures thereof, or solutions thereof. In one variation, the viscoelastic fluid comprises sodium hyaluronate. In another variation, the viscoelastic composition may further include a drug. For example, the viscoelastic composition may include a drug suitable for treating glaucoma, reducing or lowering intraocular pressure, reducing inflammation, fibrosis neovascularization or scarring, and/or preventing infection. The viscoelastic composition may also include agents that aid with visualization of the viscoelastic composition. For example, dyes such as but not limited to fluorescein, trypan blue, or indocyanine green may be included. In some variations, a fluorescent compound or bioluminescent compound is included in the viscoelastic composition to help with its visualization. In other variations, the system delivers the drug alone, without the viscoelastic composition. In this case, the drug may be loaded onto or into a sustained release biodegradable polymer that elutes drug over a period of weeks, months, or years. It is also contemplated that air or a gas could be delivered with the systems, as described herein.

Other variations of the ab-interno method for delivering a fluid composition include the use of an endoscope. Similar to the method described directly above, access to the anterior chamber is first made by incising the cornea, limbus, or sclera. Again, this may be done in combination with cataract surgery in one sitting, either before or after cataract surgery, or independently. The anterior chamber may be infused with saline solution or a viscoelastic composition may be placed in the anterior chamber to prevent its collapse. The saline or viscoelastic may be delivered as a separate step or it may be infused with the elongate member of the delivery system, an irrigating sleeve on the elongate member or cannula, or with a separate infusion cannula. The surgeon, under direct microscopic visualization, then advances the endoscope through the incision and towards the angle and trabecular meshwork. As the surgeon visualizes the trabecular meshwork via the endoscope or any associated display, the bevel of the cannula is advanced to pierce the meshwork. The elongate member is then advanced under endoscopic visualization. The elongate member may be advanced any suitable amount and direction about the canal. For example, the elongate member may be advanced between about 10 degrees to about 360 degrees about the canal, or it may be advanced in two steps, e.g., 180 degrees in a clockwise direction and 180 degrees in a counterclockwise direction about the canal (to thereby achieve a full 360 degree ab-interno viscocanalostomy). Once the elongate member has been positioned within the canal, a fluid composition, e.g., a viscoelastic fluid, may be continuously or intermittently delivered through the lumen of the elongate member. The fluid composition may exit the lumen of the elongate member through its distal end (e.g., the through the distal tip), or through openings or fenestrations provided along its shaft, or a combination of both. The openings or fenestrations may be spaced along the axial length of the elongate member in any suitable manner, e.g., symmetrically or asymmetrically along its length. Other substances such as drugs, air, or gas may be delivered in the same manner if desired. The elongate member may be repositioned by retraction or repeated advancement and retraction. In some variations of the method, the same or different incision may be used, but the delivery system cannula is employed to access and dilate Schlemm's canal from a different direction (e.g., counterclockwise instead of clockwise). Once a sufficient amount of fluid has been delivered, the surgeon may retract the slidable elongate member into the cannula and remove the delivery system from the eye.

Figure 28A:
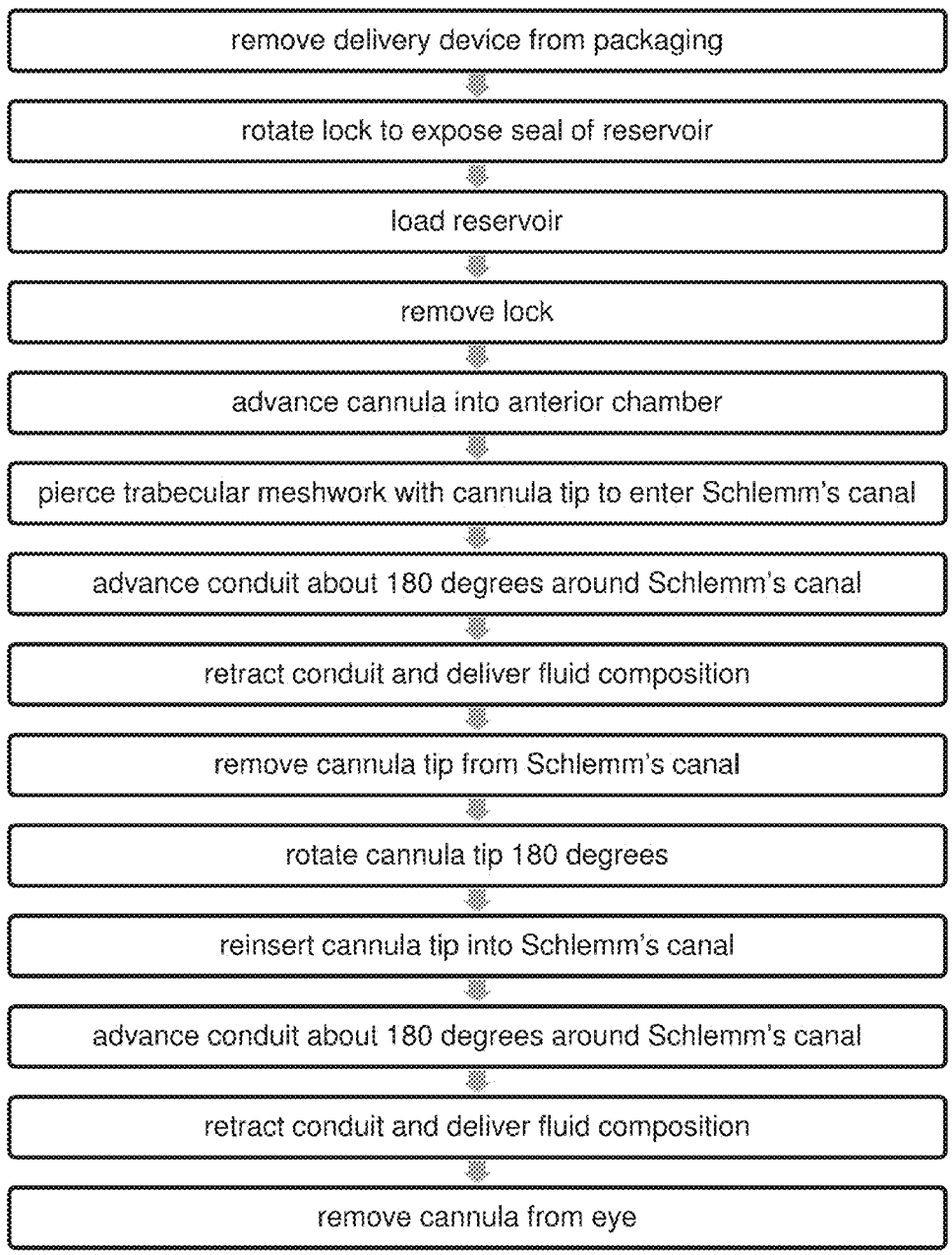
FIG. 28A is a flow-chart illustrating an exemplary method for delivering a fluid to Schlemm's canal.

One variation of the methods described here is illustrated in FIG. 28A-D, and may be carried out using a delivery system as described with respect to FIGS. 23A-23F. FIG. 28A shows a flow chart illustrating the method. The method shown there may allow for single-handed, manually operated delivery of fluid (e.g., viscoelastic fluid or gel) into Schlemm's canal via a slidable elongate member comprising a lumen (e.g., a microcatheter). The delivery of viscoelastic fluid may be metered, such that controlled, small amounts of viscoelastic can be delivered to the eye. The method may allow for catheterization and transluminal viscodilation of 360 degrees of Schlemm's canal using a single clear corneal incision for access. This may, for example, reduce intraocular pressure in patients with glaucoma (e.g., open-angle glaucoma).

First, the delivery system may be removed from its packaging. Next, the delivery system may be pre-loaded with viscoelastic fluid. A loading tool (e.g., a nozzle), which may be supplied with the delivery system in a kit, may be attached to a viscoelastic cartridge. Suitable commercially available viscoelastics include but are not limited to Healon™, HealonGV™, Amvisc™, and PROVISC™. The loading tool may then be flushed with viscoelastic. The lock on the proximal end of the delivery system may then be rotated (while remaining attached to the handle of the device device) to expose a proximal opening in the device. The nozzle may then be inserted into the proximal opening and viscoelastic fluid injected from the viscoelastic cartridge into the reservoir of the delivery system. It may be desirable to hold the delivery system and viscoelastic cartridge upright during injection. The viscoelastic fluid may be injected until viscoelastic flow from the distal tip of the cannula is visualized. The lock may then be removed from the delivery system.

To deliver viscoelastic fluid into the eye, the cannula may be advanced into the anterior chamber through an existing corneal or scleral incision. It may be desirable for the incision to be at least about 1 mm wide. The distal tip of the cannula may be used to pierce the trabecular meshwork to enter Schlemm's canal. The cannula may be held securely against the angle while the elongate member is advanced into Schlemm's canal. An exposed portion of one or more of the wheels of the drive assembly may be rotated proximally to advance the elongate member up to about 180 degrees around Schlemm's canal (about 18 mm, about 19 mm, about 20 mm, about 18 mm to about 20 mm, or about 15 mm to about 25 mm of circumferential canal travel). At this point, the elongate member may be fully extended, and the wheel may no longer be able to be rotated. During this procedure, direct microscopic or gonioscopic visualization of the cannula tip may be maintained, and the anterior chamber may be maintained with viscoelastic or continuous balanced salt solution infusion.

Figure 28B:
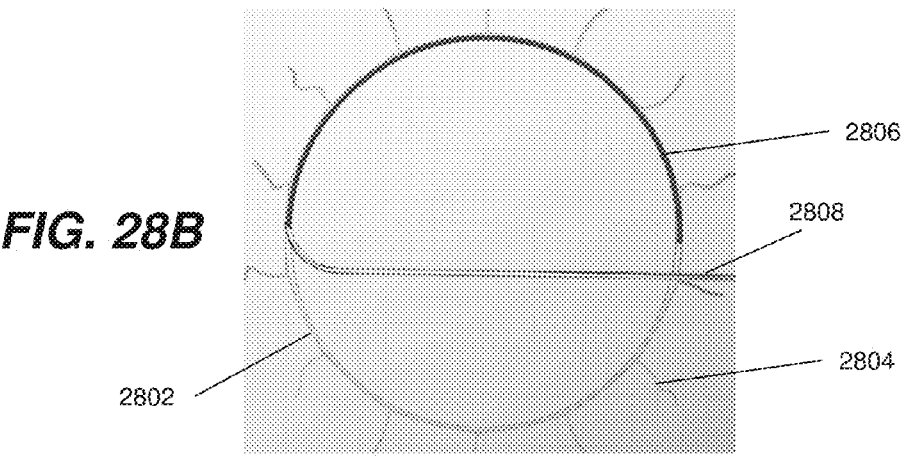
FIGS. 28B-D depict delivery of fluid as a slidable elongate member is retracted as part of the method of FIG. 28A.
Figure 28C:
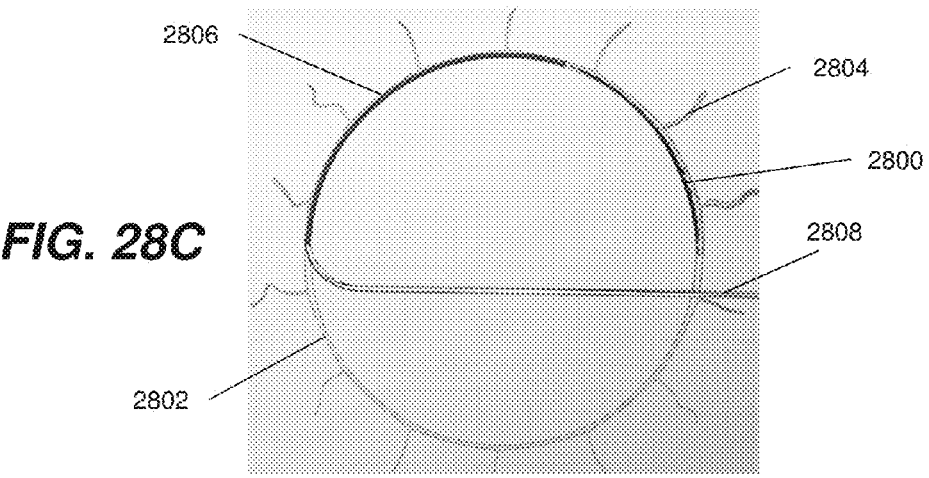
Figure 28D:
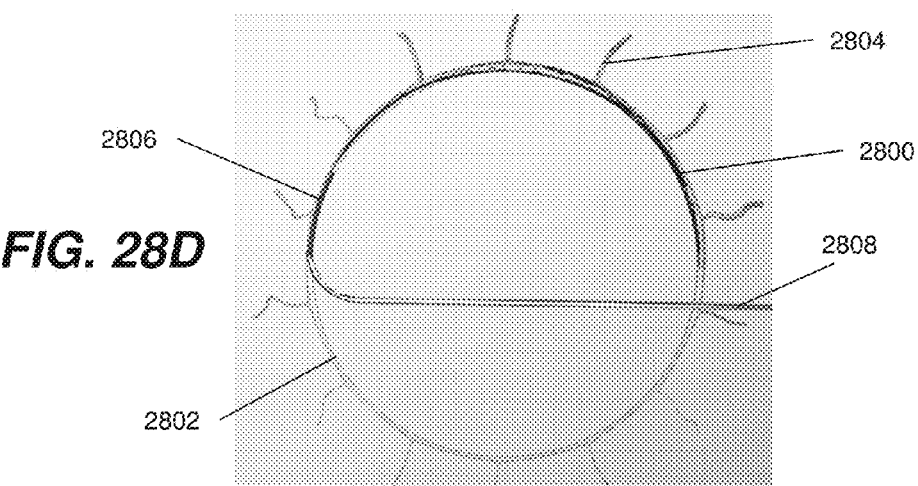

One or more wheels may then be rotated distally to retract the elongate member. As the elongate member is retracted, a specific predetermined volume of viscoelastic may be steadily delivered out of the lumen of the elongate member in a metered fashion, which may cause transluminal viscodilation of Schlemm's canal and/or collector channels. In some variations, full retraction of the elongate member results in the delivery of between about 2 µl and about 9 µl of viscoelastic fluid (e.g., about 4.5 µl of viscoelastic fluid). The wheels may be configured to be incrementally rotated with audible and/or tactile clicks at incremental rotation; in some cases, about 0.5 µl of viscoelastic fluid may be delivered with each click. The delivery of viscoelastic (2800) to Schlemm's canal (2802) and collector channels (2804) during retraction of the elongate member (2806) into the cannula (2808) is shown in FIGS. 28B-28D. As can be seen in FIGS. 28C-28D, the angle and length of delivery of viscoelastic (2800) to Schlemm's canal corresponds to the angle and length of advancement of the elongate member into the canal. In some instances, viscoelastic may be used to tamponade any blood reflux back into the anterior chamber.

Viscoelastic may then optionally be delivered to the other half of Schlemm's canal. The cannula tip may be removed from Schlemm's canal and the delivery system may be flipped, such that the cannula tip is rotated 180 degrees to face the opposite direction. In some instances, the delivery system may be flipped in the anterior chamber, without removing the cannula from the eye. In other instances, the delivery system may be removed from the eye, flipped, and reinserted into the incision. The cannula tip may then be reinserted into Schlemm's canal via the same incision in the trabecular meshwork, and advancement, retraction, and delivery of viscoelastic fluid as described above may be repeated to viscodilate the remaining 180 degrees of Schlemm's canal. The complete procedure may deliver between about 4 µl and about 18 µl of viscoelastic fluid in total to the eye (e.g., about 9 µl of viscoelastic fluid).

At the end of the procedure, the anterior chamber may be irrigated (e.g., with balanced salt solution) through the corneal wound (either manually or automated). A balanced salt solution or viscoelastic may be used to reform the anterior chamber as needed to achieve physiologic pressure and further tamponade any blood reflux from the collector channels back into the anterior chamber. If necessary, a suture may be used to seal the corneal or scleral incision. Postoperatively, an antibiotic or antiseptic, mydriatic agent, or a miotic agent, may be used as appropriate. For example, a miotic eye drop may be used for weeks or months to help prevent synechiae formation and angle closure.

More generally, in methods described herein, exemplary volumes of viscoelastic fluid that may be delivered may in some instances be between about 1 µl and about 200 µl, or in some instances be between about 1 µl and about 100 µl. In some instances, sufficient volumes to provide a disruptive force may range from about 1 µl to about 50 µl, from about 1 µl to about 30 µl, or from about 2 µl to about 16 µl. In one variation, a volume of about 4 µl is sufficient to disrupt Schlemm's canal and/or the surrounding tissues. In other variations, the volume of viscoelastic fluid sufficient to disrupt trabeculocanalicular tissues may be about 2 µl, about 3 µl, about 4 µl, about 5 µl, about 6 µl, about 7 µl, about 8 µl, about 9 µl, about 10 µl, about 11 µl, about 12 µl, about 13 µl, about 14 µl, about 15 µl, about 16 µl, about 17 µl, about 18 µl, about 19 µl, about 20 µl, about 25 µl, about 30 µl, about 35 µl, about 40 µl, about 45 µl, or about 50 µl.

Tissue disruption may occur by viscodilating excessively and intentionally with at least about 1 µl, at least about 2 µl, at least about 3 µl, at least about 4 µl, at least about 5 µl, at least about 6 µl, at least about 7 µl, at least about 8 µl, at least about 9 µl, at least about 10 µl, at least about 11 µl, at least about 12 µl, at least about 13 µl, at least about 14 µl, at least about 15 µl, at least about 16 µl, at least about 17 µl, at least about 18 µl, at least about 19 µl, or at least about 20 µl of viscoelastic fluid per 360 degree arc of the canal. In some variations, at least about 20 µl, at least about 25 µl, at least about 30 µl, at least about 35 µl, at least about 40 µl, at least about 45 µl, or at least about 50 µl of viscoelastic fluid may be delivered.

Depending on factors such as the type or severity of the condition being treated, the disruptive force may be generated to partially or completely destroy and/or remove the trabecular meshwork, and may be adjusted by varying the volume of viscoelastic fluid delivered. For example, 8 µl may be used to perforate or gently tear the meshwork, while 16 µl may be used to maximally cut or tear the meshwork. More specifically, about 1 to 2 µl may be used to dilate Schlemm's canal and collector channels; about 2 to 4 µl may be used to dilate Schlemm's canal and collector channels, and stretch juxtacanalicular tissues; and about 4 to 6 µl may be used for all the foregoing and for the creation of microtears or microperforations in the trabecular meshwork and juxtacanalicular tissues (further increasing porosity and outflow). A volume of about 8 to 16 µl may be used for all the foregoing and for substantial perforation/tearing of the trabecular meshwork and juxtacanalicular tissues. A volume of about 16 to 50 µl may be used for substantial or complete tearing or cutting of the trabecular meshwork.

Figure 16:
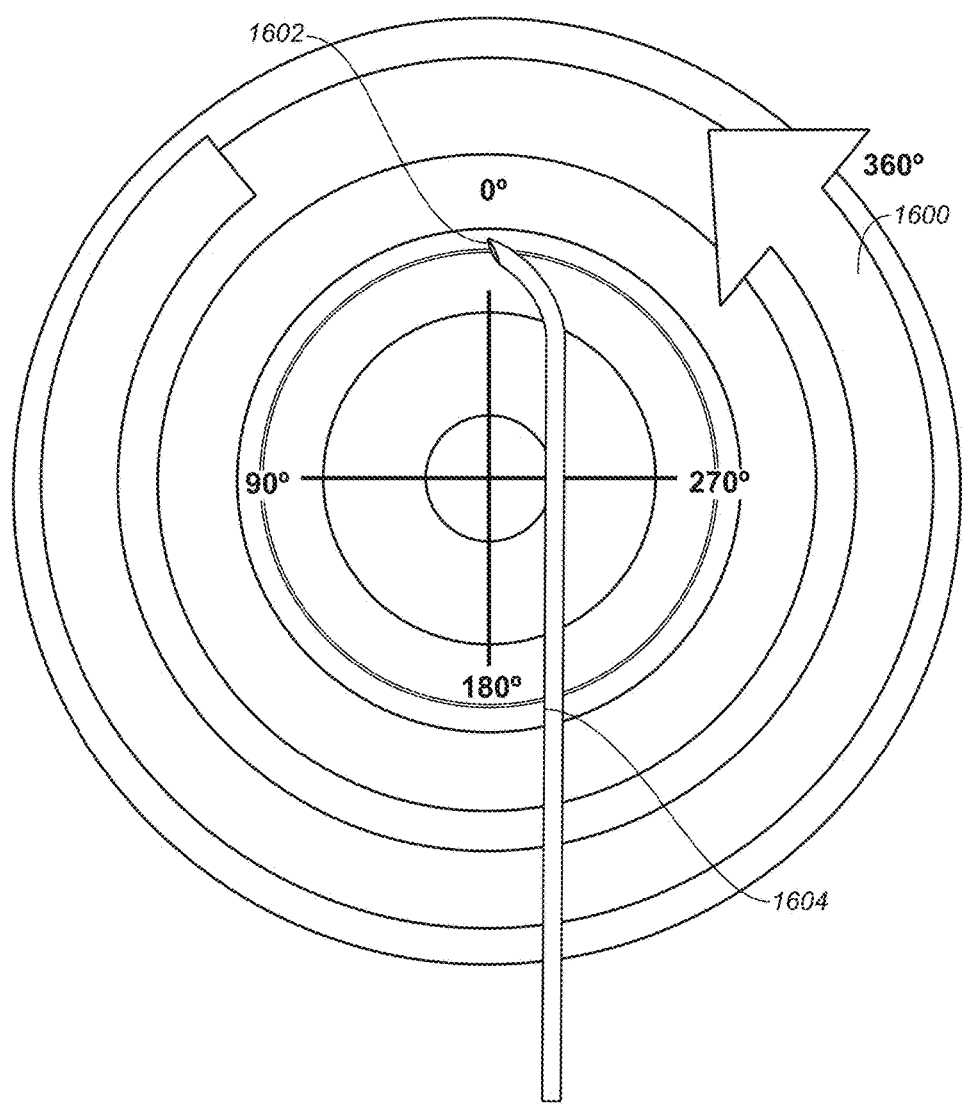
FIG. 16 is a stylized depiction of an ab-interno method of accessing Schlemm's canal from a single point, and delivering a viscoelastic fluid while advancing a fluid delivery elongate member along a 360 degree arc of the canal.
Figure 17:
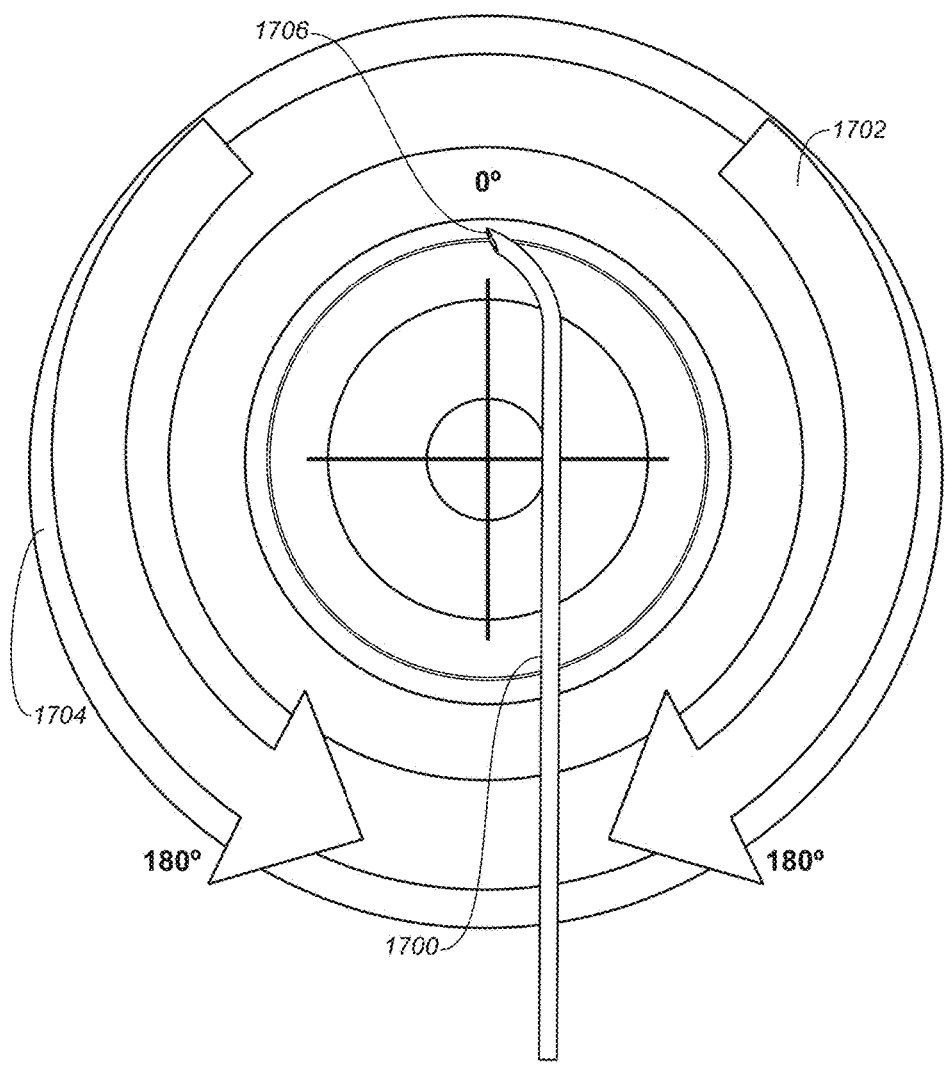
FIG. 17 is a stylized depiction of an ab-interno method of accessing Schlemm's canal from a single point, and delivering a viscoelastic fluid while advancing a fluid delivery elongate member in both the clockwise and counterclockwise directions along a 180 degree arc of the canal.

The total volume of viscoelastic fluid may be delivered along a 360 degree arc (1600) of Schlemm's canal during a single advancement from a single access point (1602) in the canal (e.g., as shown in FIG. 16) or withdrawal of the elongate member (1604), or along lesser degrees of arc in multiple advancements or withdrawals of the elongate member. For example, as shown in FIG. 17, a elongate member (1700) may be advanced along a 180 degree arc of the canal in both clockwise (1702) and counterclockwise (1704) directions to deliver fluid from, e.g., a single access point (1706) in the canal. Referring to FIGS. 16 and 17, an exemplary disruptive volume of between about 4 µl and about 18 µl may be delivered along a 360 degree arc of the canal while the elongate member is advanced from a single access point in the canal, or between about 2 µl and about 9 µl may be delivered along a 180 degree arc of the canal during two advancements (one in the clockwise direction and the other in the counterclockwise direction) of the elongate member from a single access point in the canal. More specifically, an exemplary disruptive volume may be about 9 jul delivered along a 360 degree arc of the canal, or about 4.5 µl delivered along a 180 degree arc of the canal during each of two advancements. The elongate member may access the canal from a single point or from multiple points.

Additionally, the fluid compositions may be delivered to restore the tubular anatomy of Schlemm's canal, to clear obstructions within the canal, to disrupt juxtacanalicular trabecular meshwork or the inner wall of Schlemm's canal within the canal, or to expand the canal. Here the delivery systems may include wires, tubes, balloons, instruments that deliver energy to the tissues, and/or other features to help with these methods. It is contemplated that glaucoma may be treated using such systems with additional features. The surface of these systems may also be roughened or have projections to further disrupt the inner wall of Schlemm's canal and juxtacanalicular trabecular meshwork to enhance aqueous humor outflow or permeability.

The viscoelastic fluid may be delivered while advancing the elongate member of a single-handed, single-operator controlled device from Schlemm's canal in the clockwise direction, counterclockwise direction, or both, or during withdrawal of the elongate member from Schlemm's canal. As previously stated, the viscoelastic fluid may be delivered to disrupt Schlemm's canal and surrounding trabeculocanalicular tissues. For example, the delivered viscoelastic fluid may cause disruption by dilating Schlemm's canal, increasing the porosity of the trabecular meshwork, stretching the trabecular meshwork, forming microtears or perforations in juxtacanalicular tissue, removing septae from Schlemm's canal, dilating collector channels, or a combination thereof. The elongate member may be loaded with the viscoelastic fluid at the start of an ocular procedure so that the fluid can be delivered by a single device. This is in contrast to other systems that use forceps or other advancement tool to advance a fluid delivery catheter into Schlemm's canal and/or devices containing viscoelastic fluid that are separate or independent from a delivery catheter or catheter advancement tool, and which require connection to the delivery catheter or catheter advancement tool during a procedure by an assistant while the delivery catheter or catheter advancement tool is held by the surgeon.

Tool Delivery

Prior to the introduction of goniotomy and trabeculotomy (both of which are typically used to treat an obstructed trabecular meshwork, often genetically-driven at a young age), congenital glaucoma uniformly resulted in blindness. Despite the invasiveness of goniotomy (which is performed ab-interno, but a sharp scalpel is used to cut 30-60 degrees of meshwork to improve outflow) and trabeculotomy (ab-externo method where deep scleral incisions unroof Schlemm's canal and the meshwork is cut with a probe), the procedures are viewed as being effective and have allowed many pediatric patients to possibly avoid an entire lifetime of blindness. In 1960, Burian and Smith each independently described trabeculotomy ab-externo. In this highly invasive ab-externo operation, the surgeon makes a deep scleral incision, finds Schlemm's canal, cannulates all 360 degrees of Schlemm's canal externally with a catheter or specially designed probe called a trabeculotome, and finally tensions both ends of the catheter or probe to the point where the trabeculotome cuts through the entire trabecular meshwork into the anterior chamber to improve drainage.

More recent attempts at decreasing the invasiveness of ab-externo trabeculotomy have been developed by NeoMedix, which commercializes a device called "Trabectome." The Trabectome attempts to make trabeculotomy easier by using an ab-interno approach. The instrument and methods involve removal of the trabecular meshwork ab-interno by electrocautery using an instrument that also provides infusion and aspiration. The disadvantages of the Trabectome are three-fold: 1) the device employs an energy-based mechanism to ablate trabecular meshwork, which is believed to cause inflammation and scarring in the eye, which in turn can adversely impact outflow and pressure; 2) the device/procedure is ergonomically limited—it requires a foot pedal and power cords to activate electrocautery and irrigation in addition to being limited to 60-120 degrees of meshwork therapy per corneal or scleral entry incision; and 3) because it involves energy-based ablation and irrigation, there is capital equipment required.

The methods (as well as systems and devices) described herein, including the method for providing a disruptive force to trabeculocanalicular tissues, may be highly suitable for ab-interno trabeculotomy and goniotomy given that they avoid the use of electrocautery, and are capable of advancing elongate members over larger degrees of arc of Schlemm's canal. When the systems and devices are tailored to provide a disruptive force to the trabeculocanalicular tissues, implant-free methods may be employed, e.g., by delivering a disruptive volume of viscoelastic fluid, advancing disruptive tools, e.g., cannulas, elongate members, catheters, etc., or both. In some instances, disruptive tools may comprise disruptive components on their distal portions. Exemplary disruptive components include, without limitation, notches, hooks, barbs, balloons, or combinations thereof. In other instances, the disruptive tools may not comprise disruptive components on their distal portions, and indeed may have atraumatic blunt distal portions. Exemplary atraumatic distal portions include, without limitation, parasol or dome shaped distal portions.

In some variations of the ab-interno trabeculotomy and goniotomy methods, the procedure includes advancing a cannula at least partially through the anterior chamber of the eye, entering Schlemm's canal at a single access point using the cannula, and delivering a volume of a viscoelastic fluid through a elongate member comprising a lumen and slidable within, and extendable from, the cannula, sufficient to disrupt the structure of Schlemm's canal and surrounding tissues to reduce intraocular pressure. Other methods that may be useful in treating conditions of the eye include the steps of entering Schlemm's canal using a elongate member extendable from a single-operator controlled handle, the handle comprising a fluid reservoir, and delivering a volume of a viscoelastic fluid from the fluid reservoir through the elongate member by increasing pressure within the fluid reservoir, where the volume of delivered viscoelastic fluid is sufficient to disrupt the structure of Schlemm's canal and surrounding tissues to reduce intraocular pressure. The disruptive volume may be between about 2 μl to about 16 μl. In one variation, the disruptive volume is about 4 μl of viscoelastic fluid. As previously stated, in some instances the disruptive volume may range anywhere between about 20 μl to about 50 μl. Methods based on fluid delivery are described in more detail above.

When fluids are not used, and only a disruptive tool is employed, the outer diameter of the elongate member or tool may be variously sized for disruption of tissues, analogous to how fluid volumes may be varied to vary the level of disruption. For example, an elongate member or tool having an outer diameter ranging from about 50 to about 100 microns may be advanced through the canal to slightly dilate the canal and break or remove septae obstructing circumferential canalicular flow. An elongate member or tool having an outer diameter ranging from about 100 to 200 microns may be employed to perform the foregoing, and may also to begin to stretch the trabecular meshwork and juxtacanalicular tissues. An elongate member or tool having an outer diameter ranging from about 200 to about 300 microns may be able to perform the above, but may also create microtears in the trabecular meshwork and juxtacanalicular tissues, and may maximally dilate the collector channels. An elongate member or tool having an outer diameter ranging from about 300 to about 500 microns may maximally disrupt the tissues and may create tears or perforations all along the trabecular meshwork and juxtacanalicular tissues. Additionally, the further the advancement of the elongate member or tool through the canal, the greater the efficacy of the procedure. For example, the elongate member or tool may be advanced out from the tip of the cannula and into the canal about a 30 degree arc of the canal (e.g., advanced about 3 to 4 mm out of the cannula), advanced about a 60 degree arc of the canal (e.g., advanced about 6 to 8 mm out of the cannula), advanced about a 90 degree arc of the canal (e.g., advanced about 10 mm out of the cannula), advanced about a 120 arc of the canal (e.g., advanced about 15 mm out of the cannula), advanced about a 180 degree arc of the canal (e.g., advanced about 20 mm out of the cannula), or advanced about a full 360 degrees of the canal (e.g., advanced about 36 to 40 mm out of the cannula), for maximal efficacy and maximal intraocular pressure reduction. In some variations, the elongate member may have a non-uniform outer diameter. For example, the elongate member may have a tapered outer diameter, such that the outer diameter increases from the distal to proximal end.

In some variations, the methods disclosed herein may include advancement of the elongate member (or a tool) between about a 5 degree arc of Schlemm's canal and about a 360 degree arc. In some variations, the methods may include advancement of the elongate member (or tool) about a 360 degree arc of Schlemm's canal, about a 270 degree arc of Schlemm's canal, about a 120 degree arc of Schlemm's canal, about a 180 degree arc of Schlemm's canal, or about a 90 degree arc of Schlemm's canal. In yet further variations, advancement of the elongate member (or a tool) may be about a 0 to 5 degree arc of Schlemm's canal, about a 30 degree arc of Schlemm's canal, or about a 60 degree arc of Schlemm's canal. Advancement may occur from a single access point in Schlemm's canal or from multiple access points in the canal. When a disruptive force is to be provided, it may be beneficial to advance the elongate member in both clockwise and counterclockwise directions about a 180 degree arc of Schlemm's canal from a single access point in the canal.

Depending on factors such as the type or severity of the condition being treated, the disruptive force may be generated to partially or completely destroy and/or remove the trabecular meshwork, and may be adjusted by varying the tool configuration. In some methods, the trabecular meshwork may be disrupted during advancement of the slidable elongate member. Customizing a body segment of the elongate member proximal to the tip with one or more notches, barbs, or balloons that catch the meshwork as the distal tip is being guided and advanced along Schlemm's canal could also be used, thereby disrupting, partially tearing, fully tearing, and/or removing trabecular meshwork upon advancement. Additionally, an implant with edges specifically designed to cut the meshwork could be used.

Figure 18A:
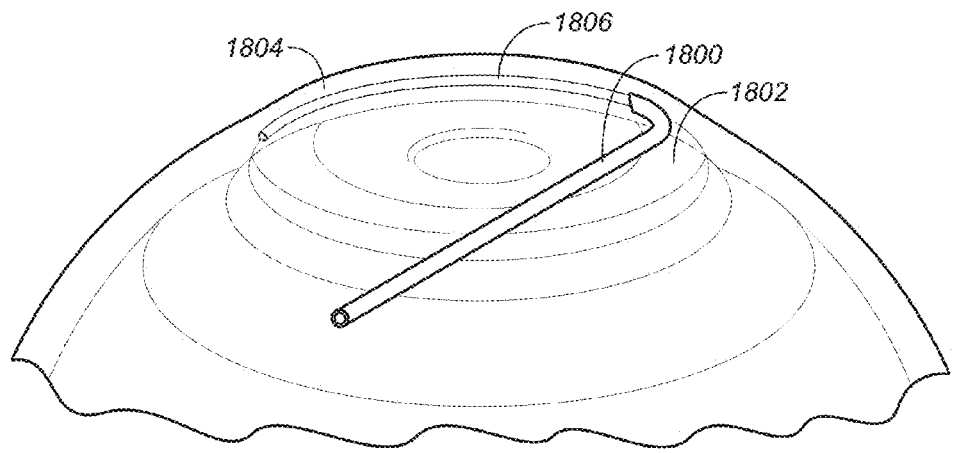
FIGS. 18A-18C illustrate an exemplary ab-interno method of cutting or tearing the trabecular meshwork.
Figure 18B:
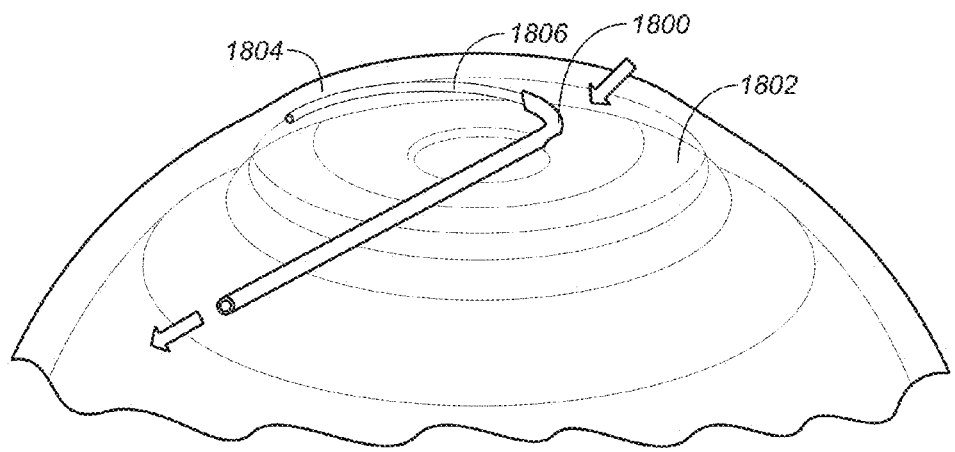
Figure 18C:
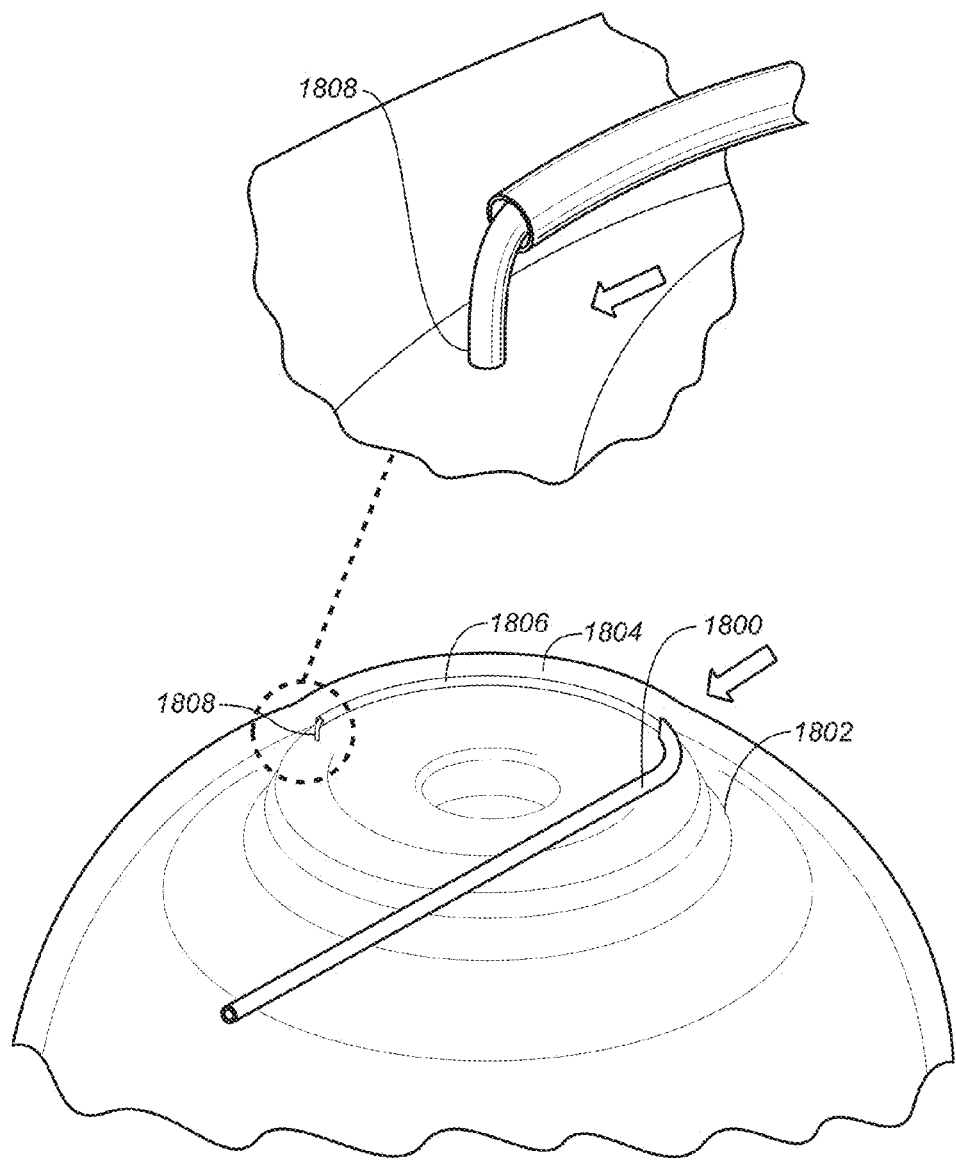

In yet other methods, the trabecular meshwork may be disrupted during retraction of the slidable elongate member. Still other methods for disrupting tissues may involve customizing the system (e.g., the elongate member, any catheters or wires, probe tips, etc.) to catch or grasp the meshwork upon retraction after complete advancement through the canal. This may be done using a wire with a bent tip, hook, notch, or barb on its end that is advanced through the lumen of the catheter that then snags the meshwork upon retraction, tearing it along its length or removing it altogether, or solely with a metal or polymer wire or suture (no catheter) whose tip (and/or body) is hooked, notched, or barbed in such a way that it can be advanced into Schlemm's canal without tearing the meshwork but snags the meshwork upon retraction, tearing the meshwork and/or removing it completely. Alternatively, as shown in FIG. 18C, the elongate member (1806) may be provided with a disruptive tool, e.g., a sharp-edged element (1808), that can cut or tear the trabecular meshwork while being retracted into the cannula (1800), which is held stationary. Exemplary sharp-edged elements may be a hook, wire, or any other suitable shape memory component that can extend from the cannula to tear, cut, or remove trabecular meshwork.

Another method for disrupting tissues may include using oversized elongate members (e.g., having an outside diameter of 300-500 microns) to tear the meshwork upon delivery, or inflating or expanding the elongate member once it has been fully advanced into Schlemm's canal to stretch, disrupt, rupture, or fully tear the meshwork. For example, a catheter/elongate member, probe, or wire (with or without a lumen) whose tip is 200-250 microns in outer diameter, but having a shaft that begins to flare outwards after 3 clock hours of Schlemm's canal (i.e., at about the 5 or 10 mm mark on the catheter/elongate member) up to about 300, up to about 400, or up to about 500 microns, may be used, so that as the tip advances comfortably within Schlemm's canal, the enlarged shaft trails behind and ruptures the trabecular meshwork as it is advanced.

In another method, cutting, destruction, removal, or the like of the trabecular meshwork may be accomplished by removing the cannula from the eye while leaving the elongate member in the canal, thereby tearing through the meshwork. Referring to FIG. 18A, a cannula (1800) may be inserted into the anterior chamber (1802) and Schlemm's canal (1804), and a tool (e.g., a slidable elongate member (1806)) may be advanced within the canal (1804). As shown in FIG. 18B, the cannula (1800) can be removed from the anterior chamber (1802) without retracting the elongate member (1806). This action by itself may tear the trabecular meshwork. As the cannula (1800) is removed from the anterior chamber (1802), the elongate member (1806) may begin tearing the trabecular meshwork from the point at which the cannula (1800) was inserted into Schlemm's canal (1804), and may continue tearing around the trabecular meshwork toward the distal end of the elongate member.

Figure 29A:
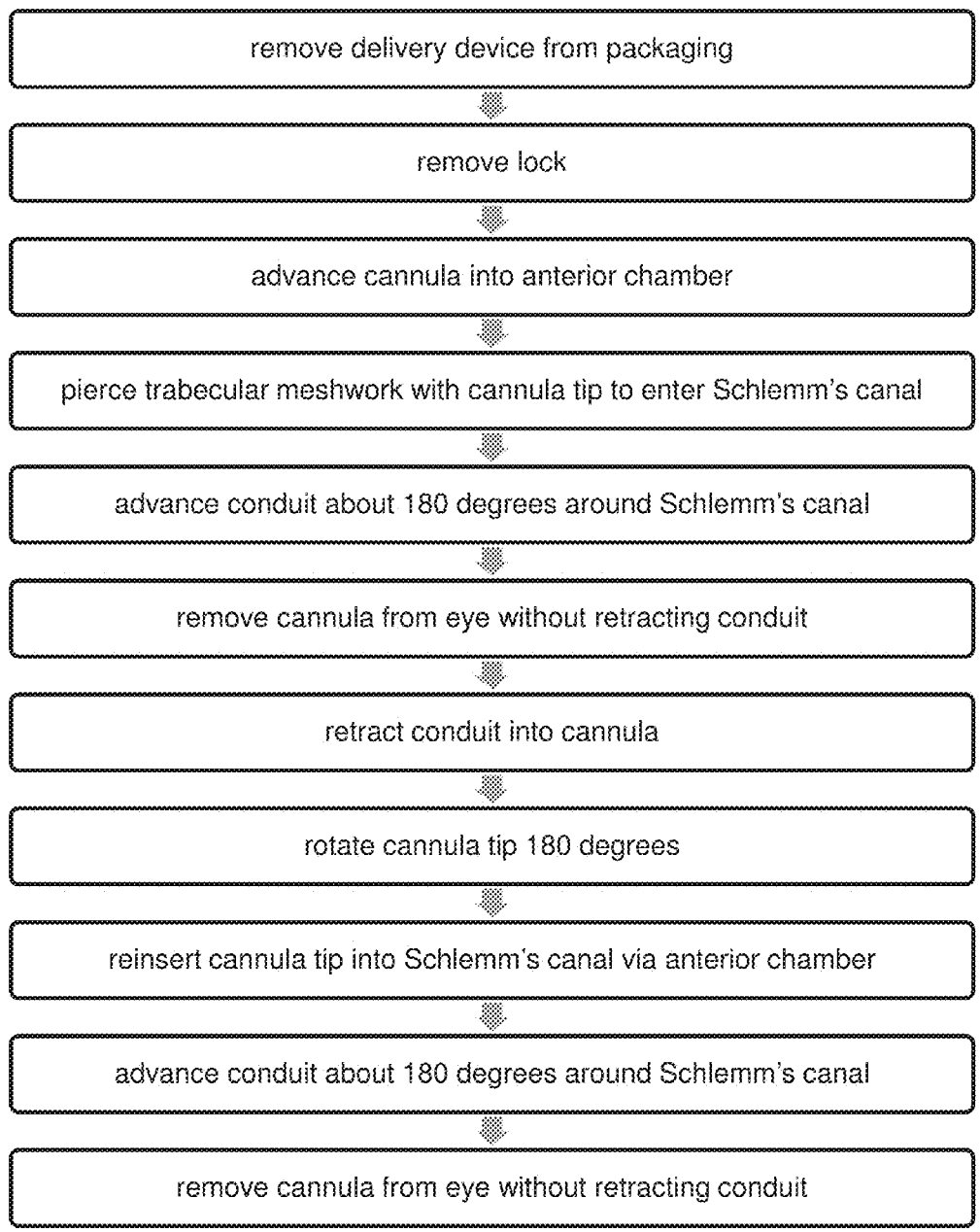
FIG. 29A is a flow-chart illustrating an exemplary method for disrupting trabecular meshwork.

A variation of the methods described here is illustrated in FIGS. 29A-29D, and may be carried out using a delivery system such as one described with respect to FIGS. 23A-23F. FIG. 29A shows a flow chart illustrating the method. The method may be used to access the trabecular outflow system using a single clear corneal incision, and may allow for transluminal trabeculotomy of up to 360 degrees. The method may use a flexible elongate member that may be advanced and retracted using a single-handed disposable manual instrument. First, the device may be removed from its packaging. The lock may then be removed from the delivery system. The cannula may be advanced into the anterior chamber through an existing corneal or scleral incision. It may be desirable for the incision to be at least about 1 mm wide. The distal tip of the cannula may be used to pierce the trabecular meshwork to enter Schlemm's canal. The cannula may be held securely against the angle while the flexible elongate member is advanced into Schlemm's canal. An exposed portion of one or more of the wheels may be rotated proximally to advance the flexible elongate member up to about 180 degrees around Schlemm's canal (about 20 mm of circumferential canal travel). At this point, the flexible elongate member may be fully extended, and the wheel may no longer be able to be rotated. During this procedure, direct microscopic or gonioscopic visualization of the cannula tip may be maintained, and the anterior chamber may be maintained with viscoelastic or continuous balanced salt solution infusion.

Figure 29B:
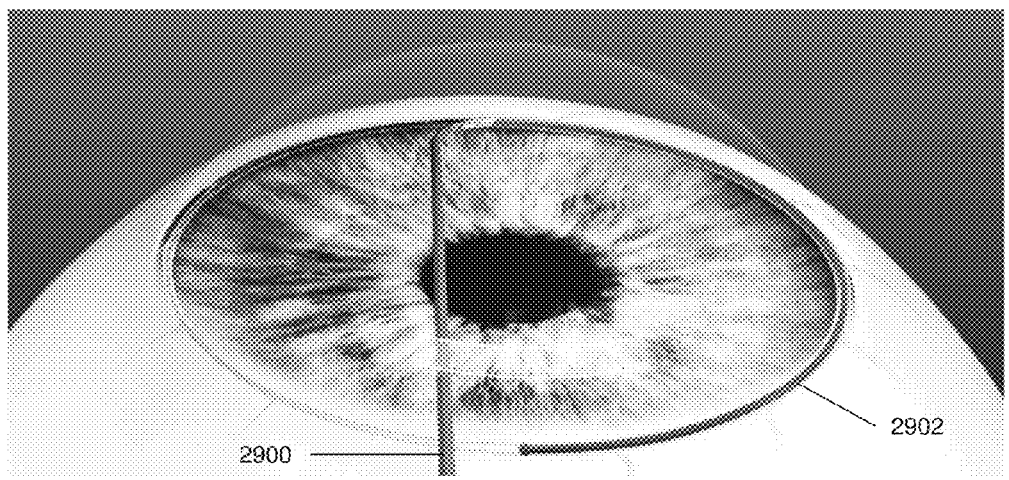
FIGS. 29B-D depict disruption of the trabecular meshwork as part of the method of FIG. 29A.
Figure 29C:
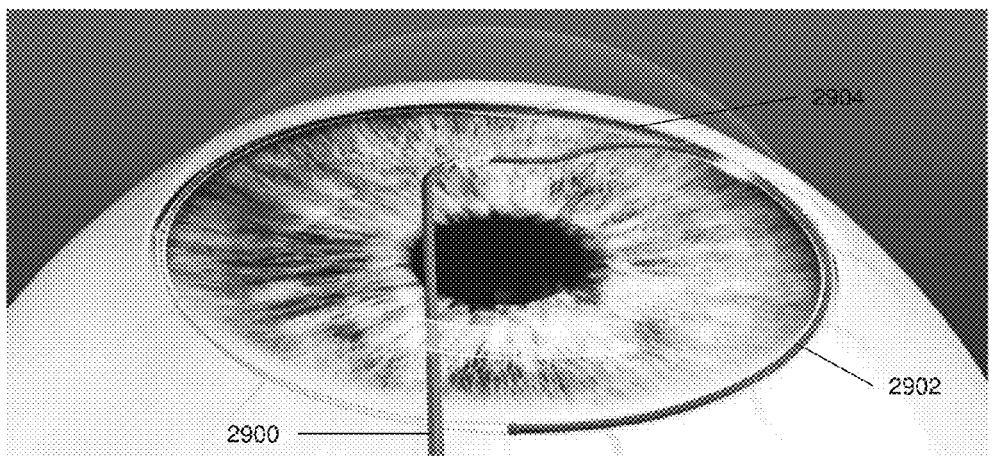
Figure 29D:
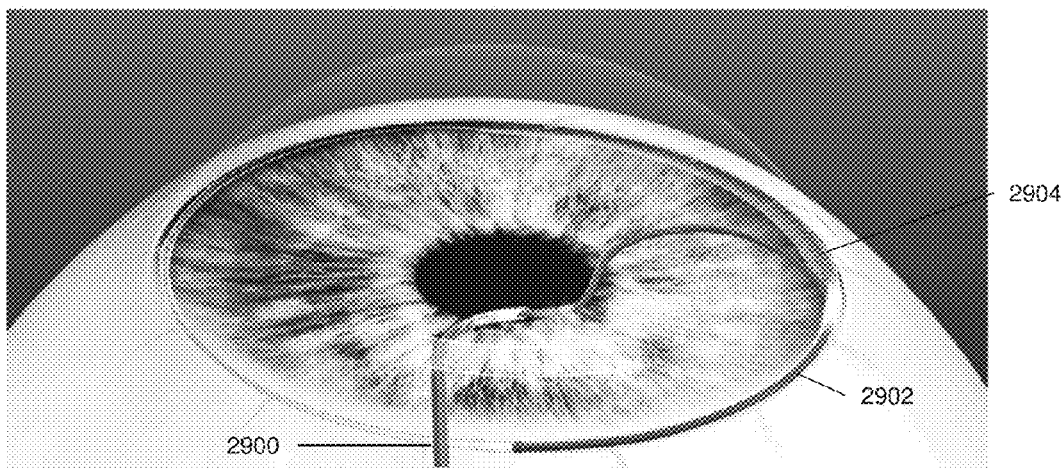

Once the flexible elongate member is advanced, the cannula may be removed from the eye through the incision without retracting the flexible elongate member. This may cause the flexible elongate member to cut through the trabecular meshwork. In some instances, it may be desirable to bias the distal tip of the cannula toward the trabecular meshwork being cut; this may in some instances help to prevent the flexible elongate member from slipping out of the canal during cannula removal. Removal of the cannula (2900) without retraction of the flexible elongate member (2902) to tear the trabecular meshwork (2904) is illustrated in FIGS. 29B-29D. As can be seen there, the elongate member (2902) transmits the force from removing the cannula (2900) into a force that tears the trabecular meshwork. Removal of the cannula (2900) results in an "unzipping" effect to tear the trabecular meshwork. That is, the trabecular meshwork is torn by the body of the elongate member (2902) from its proximal to distal end. First, force on the trabecular meshwork from the proximal end of the body of the elongate member (2902) causes the trabecular meshwork to tear near the insertion point of the cannula (2900). As the cannula (2900) continues to be withdrawn from the eye, as shown in FIGS. 29C and 29D, the body of the elongate member (2902) continues to tear through the trabecular meshwork, toward the distal tip of the elongate member. It should be noted that this method causes the trabecular meshwork to be progressively torn from a first location (the proximal end of the extended elongate member, near the insertion point of the cannula) to a second location (the distal end of the extended elongate member), as opposed to being cut or torn simultaneously along the distance from the first location to the second location. Furthermore, it should be noted that in this method each portion of the trabecular meshwork is not torn by a single feature of the elongate member (e.g., a distal end of the elongate member upon advancement or retraction); rather, each portion of the trabecular meshwork is torn by the portion of the elongate member adjacent to it after the elongate member has been advanced.

After the delivery system is fully removed from the eye, the flexible elongate member may be retracted back into the cannula by rotating one or more of the wheels distally. Once the flexible elongate member is fully retracted, the delivery system may be flipped, such that the cannula tip is rotated 180 degrees to face the opposite direction. The cannula tip may then be advanced into the anterior chamber through the corneal or scleral incision, and the distal tip may be advanced into the same entry into Schlemm's canal. The method described above may then be repeated on the second half of Schlemm's canal to cut through the trabecular meshwork. In some instances, viscoelastic may be used to tamponade any blood reflux back into the anterior chamber.

At the end of the procedure, the anterior chamber may be irrigated (e.g., with balanced salt solution) through the corneal wound (either manually or automated). A balanced salt solution or viscoelastic may be used to reform the anterior chamber as needed to achieve physiologic pressure and further tamponade any blood reflux from the collector channels back into the anterior chamber. If necessary, a suture may be used to seal the corneal or scleral incision. Postoperatively, an antibiotic or antiseptic, mydriatic agent, or a miotic agent, may be used as appropriate. For example, a miotic eye drop may be used for weeks or months to help prevent synechiae formation and angle closure.

In yet further methods, tissue disruption may be accomplished by the ab-interno delivery of a suture throughout Schlemm's canal, which is then sufficiently tensioned to stretch the canal, disrupt the trabecular meshwork, and/or tear through the meshwork ("ab-interno suture trabeculotomy"). Here a tool including a grasping element may be employed for pulling the distal suture tip inwards as the cannula is being withdrawn from the eye, severing all 360 degrees or a segment of the trabecular meshwork, or for tying the suture ends together to provide tension on the meshwork without necessarily tearing it.

Ab-Externo Approach

An ab-externo approach to implanting an ocular device or delivering a fluid composition may include additional or slightly different steps. For example, the creation of tissue flaps, suturing, etc., may be part of the ab-externo method. In general, the ab-externo method for implanting an ocular device may include the following steps. First, under microscopic visualization, conjunctiva is incised, a scleral flap is created and tissue is dissected to identify the ostia into Schlemm's canal. The anterior chamber may be separately infused with saline or may have a viscoelastic composition placed in it to prevent collapse of the anterior chamber angle. The operation may be done as a standalone procedure or in combination with cataract surgery in one sitting. It may also be done before the cataract surgery portion or after it.

Using the delivery system described herein, the cannula may be advanced into Schlemm's canal and the ocular device advanced using the positioning element under direct microscopic visualization or through a gonioscope or gonioprism. When the ocular device is advanced the desired amount, the surgeon may release the ocular device from the positioning element by actuating the engagement mechanism and remove the delivery system from the eye and operating field. The scleral wound may be self-sealing, or it may then be closed, using for example, sutures or tissue adhesive. If repositioning of the ocular device is needed or desired, the surgeon may retract and/or advance the ocular device using the positioning element of the delivery system.

With respect to the delivery of a fluid composition, the ab-externo method is similar to ab-interno delivery. However, instead of using a positioning element, the delivery system employs a slidable elongate member to infuse a fluid composition into Schlemm's canal. First, under microscopic visualization, conjunctiva is incised, a scleral flap is created and tissue is dissected to identify the ostia into Schlemm's canal. The anterior chamber may be separately infused with saline or may have a viscoelastic composition placed in it to prevent collapse of the anterior chamber angle. The operation may be done as a standalone procedure or in combination with cataract surgery in one sitting. It may also be done before the cataract surgery portion or after it.

Using the delivery system described herein, the cannula may be advanced into Schlemm's canal and a elongate member coaxially disposed within the cannula lumen may be advanced into the canal under gonioscopic visualization. Once the elongate member has been positioned within the canal, a fluid composition, e.g., a viscoelastic fluid, may be continuously or intermittently delivered through the elongate member. The fluid composition may exit the lumen of the elongate member through its distal end (e.g., the through the distal tip), or through openings or fenestrations provided along its shaft, or a combination of both. The openings or fenestrations may be spaced along the axial length of the elongate member in any suitable manner, e.g., symmetrically or asymmetrically along its length. Other substances such as drugs, air, or gas may be delivered in the same manner if desired. The elongate member may be repositioned by retraction or repeated advancement and retraction. The delivery system may then be removed from the eye.

The configuration of the ocular delivery system may be advantageous in many different respects. In one aspect, the delivery system is capable of being used in an ab-interno method of implanting an ocular device in Schlemm's canal or an ab-interno method of delivering a fluid composition or a tool into the canal. In another aspect, the delivery system cannula is configured to allow easy and atraumatic access to Schlemm's canal. Furthermore, the delivery system is configured in a manner that gives the surgeon greater freedom of use, all in a single instrument. For example, the handle of the system is configured so that it can be used with either side up (i.e., by flipping over the handle or rotating the cannula). Thus, the delivery system is designed to be used in a clockwise or counterclockwise direction with either hand and in either eye. For example, the delivery system is capable of being used with the right or left hand to access Schlemm's canal in a counterclockwise fashion, or used with the right left hand to access the canal in a counterclockwise fashion, in either eye. Thus, access to the canal from all four quadrants of the eye can be achieved. In yet a further respect, the delivery system comprises single-handed, single-operator controlled devices configured to provide a force sufficient to disrupt Schlemm's canal and surrounding tissues to improve flow through the trabeculocanalicular outflow pathway. The systems generally combine access cannulas, delivery elongate members, elongate member advancement mechanisms, disruptive tools, and viscoelastic fluids into a single device so that one person or one hand can advance the elongate member or tool, or deliver the fluid.

Methods of Manufacturing the Cannula

As mentioned above, the cannulas described here may be configured to both pierce the trabecular meshwork or other tissue, and reversibly deliver the elongate member without cutting, breaking, or otherwise damaging the elongate member. In order to accomplish this dual purpose, the cannulas may be manufactured to comprise distal ends with both sharp and dull or blunt portions. Generally, methods of manufacturing the cannulas described here may comprise creating a bevel at a distal tip of the cannula, sharpening the distal end of the distal tip to create a sharpened piercing tip, smoothing a portion of the distal tip of the cannula, and bending a portion of the cannula along a longitudinal axis of the cannula. In some variations, methods may also comprise acquiring a cannula of an appropriate working length, roughening an outer surface of the cannula, applying a protective covering to a portion of the distal tip, polishing a portion of the cannula, and cleaning the cannula.

Figure 19:
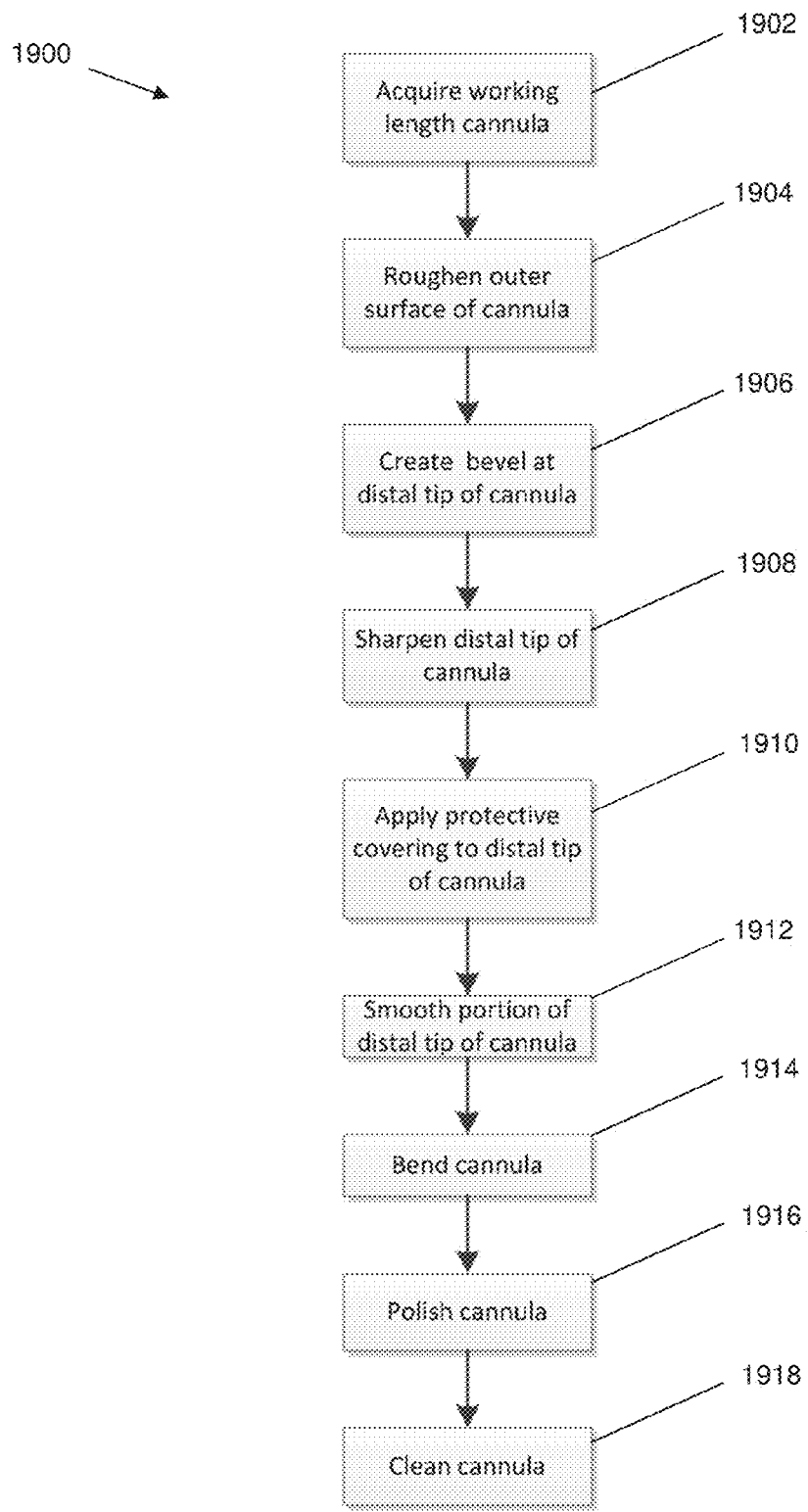
FIG. 19 is a flow-chart illustrating an exemplary manufacturing method for a cannula that may be used with the devices, systems, and methods described here.

FIG. 19 depicts an exemplary method of manufacturing a cannula for use with the devices, systems, and methods described here. As shown there, a method of manufacturing the cannula (1900) may comprise acquiring a cannula of an appropriate working length (1902), roughening an outer surface of the cannula (1904), creating a bevel at a distal tip of the cannula (1906), sharpening the distal tip of the cannula (1908), applying a protective covering to a portion of the distal tip of the cannula (1910), smoothing a portion of the distal tip of the cannula (1912), bending the cannula (1914), polishing the cannula (1916), and cleaning the cannula (1918). It should be appreciated that while the method steps in FIG. 19 are depicted in a particular order, many of the steps may be completed in a different order, and some of the steps may be optional all together, as is discussed in more detail below.

To begin the process, a cannula of a suitable working length may be acquired (1902). The cannulas may be purchased pre-cut to a desired working length, or the raw material used to create the cannulas, for example, stainless steel hypodermic tubing, may be purchased in bulk quantities and cut to the appropriate length during the cannula manufacturing process. The cannulas may be examined for damage or other visual defects upon acquisition and throughout the manufacturing process. In some variations, the working length (i.e., a length suitable for handling the cannula during manufacturing) may correspond to the final desired length of the cannula. In other variations, for ease of manufacturing for example, the working length may be longer than the desired length, and the cannula may be cut or shortened to the final desired length at any point during the manufacturing process (e.g., by cutting the proximal end of the cannula), including as the last step of the process. Exemplary working lengths include, but are not limited to, between about 50 mm and about 70 mm, between about 40 mm and about 90 mm, and more specifically, about 60 mm.

The proximal end of the cannula may be cut, treated, and/or finished at any time during the manufacturing process. In some instances, the proximal end of the cannula may be square cut (i.e., cut substantially perpendicular to the longitudinal axis of the cannula). The edges of the proximal end may be smoothed or rounded using any suitable method, for example, by media blasting. This smoothing of the proximal end of the cannula may prevent cutting, tearing, or otherwise damaging the elongate member. For example, smoothing the proximal end may remove any sharp edges or jagged surfaces therefrom, and may remove any debris or deposits remaining in the proximal end of the lumen from the cutting process. The proximal end of the cannula may be inspected after smoothing, and if sharp or serrated edges remain, the proximal end may be further smoothed.

In some variations, an outer surface of the cannula may optionally be roughened (1904) or texturized, which may assist in adhering the cannula to the handle. For example, in some instances, a proximal or central portion of an outer surface of the cannula may be abrasively blasted to create a textured or rough surface to which adhesive may be applied. Abrasively blasting an outer surface of the cannula may increase the surface area of the abrasively blasted portions, which may provide for better adhesion between the handle and the cannula.

As described above, the distal end of the cannula may be beveled. The bevel may be created (1906) by cutting or grinding the distal end of the cannula at an angle relative to the longitudinal axis of the cannula. More specifically, the bevel may be installed such that it traverses and is transverse to the lumen of the cannula. FIG. 3 depicts a side view of a cannula (300) comprising a bevel (312) at its distal tip (306). The bevel (312) may comprise an angle (A) between about 5 degrees and about 85 degrees. As mentioned above, the angle (A) may be important to properly puncture the trabecular meshwork and access Schlemm's canal without damaging other surrounding tissue, and/or to adequately visualize advancement and retraction of the elongate member. In some variations, the angle (A) may be about 5, 10, 15, 20, 25, 30, 35, 40, 45, 50, 55, 60, 65, 70, 75, 80, or 85 degrees. In some variations, the angle (A) may be between about 23 degrees and about 27 degrees. In some of these variations, the angle (A) may be about 25 degrees.

FIG. 20 depicts a perspective view of a distal tip (2002) of a cannula (2000) after a bevel has been created. As shown, the beveled distal tip (2002) now comprises a proximal end (2008) and a distal end (2010). Additionally, creating the bevel at the distal tip (2002) may elongate the opening (2012) at the distal tip (2002) creating an elliptical, rather than circular, shaped opening. Thus, beveling the distal tip (2002) may yield an elliptical shaped lumen opening that is angled such that the top of the elliptical opening is closer to the proximal portion of the cannula than the bottom of the elliptical opening. Also shown in FIG. 20 are inner and outer circumferential edges (2004, 2006).

Although installing the bevel may create sharp edges, and in some instances, a sharp distal tip, it may be desirable to further sharpen a portion of the distal tip of the cannula to achieve easier access into Schlemm's canal with higher precision. Accordingly, in some instances, after the bevel has been created, the distal tip may be further sharpened (1908) to create a sharpened piercing tip that may further assist in piercing the trabecular meshwork. The distal tip may be sharpened using any suitable means, for example, by grinding or otherwise removing a portion of the external surface and/or a portion of the outer circumferential edge of the distal end of the distal tip of the cannula. To minimize unwanted sharp edges that may damage the elongate member, it may be desirable to maintain as much of the wall thickness at the distal tip as possible, and to ensure that the thickness of the wall is uniform. It may also be beneficial to prevent cannula material or other sharpening byproducts from forming, building-up, adhering to, or otherwise being deposited on an internal surface of the cannula in the lumen. Such materials may become debris create raised or sharp surfaces or edges that may cut or damage the elongate member when the delivery system is in use.

FIGS. 21A and 21B depict perspective and front views, respectively, of a variation of a distal tip (2100) of a cannula comprising both a bevel (2102) and a sharpened piercing tip (2114). The distal tip (2100) also comprises a proximal end (2108), a distal end (2110), inner and outer circumferential edges (2104, 2106), and a lumen opening (2112). The sharpened piercing tip (2114) may be created by grinding the distal end (2110) of the distal tip (2100), thereby creating two angled surfaces (2116) that converge to form a sharp point. The angled surfaces (2116) may be formed at any suitable angle that results in a sharpened piercing tip (2114). For example, in some instances, the angle surfaces (2116) may have an angle (B) relative to the longitudinal axis of the distal tip (2100) of about 20, 25, 30, 35, 40, 45, or 50 degrees, between about 25 and about 50 degrees, or between about 37.5 and about 42.5 degrees. Accordingly, in some variations, the angle between the two angled surfaces (2116) may be between about 50 and about 100 degrees. It should be appreciated that although the distal tip (2100) is depicted with two angled surfaces, a distal tip with a single angled surface may also be used.

Turning back to FIG. 19, the method for manufacturing the cannula (1900) may further comprise smoothing a portion of the distal tip (1912) of the cannula. In variations in which the distal tip of the cannula is sharpened, as described above with respect to FIGS. 21A and 21B, the method may further comprise applying a protective covering (1910) over the sharpened portion of the distal tip, for example, the distal end of the sharpened piercing tip (2114) and/or the angled surfaces (2116), prior to smoothing the distal tip (1912). In variations in which the distal tip is not sharpened after it is beveled, it may still be desirable to apply a protective covering over the distal end of the distal tip (as described with respect to FIG. 20 above). Applying a protective covering may help to maintain the sharp edge(s) during smoothing.

As mentioned above, the distal tip of the cannula may be configured to both pierce tissue, and to deliver a elongate member. The elongate member itself may be susceptible to being pierced, cut, severed, or otherwise damaged by the cannula. In order to protect the elongate member, it may be important to smooth or deburr the surfaces and/or edges of the distal tip of the cannula that the elongate member may contact. For example, referring again to FIGS. 21A and 21B, in some variations, a portion of the inner and/or outer circumferential edges (2104, 2106), the surface between the edges (2118), and/or the internal and/or external surfaces of the cannula adjacent to the opening (2112), may be smoothed. This may even out and/or dull these edges and surfaces. For example, it may be desirable to smooth a portion of the inner circumferential edge (2104) at the proximal or distal end (2108, 2110) of the distal tip (2100), or to smooth the entire inner circumferential edge. In some instances, a portion of the outer circumferential edge (2106) may also be smoothed while maintaining the sharp edges of the distal tip (e.g., the sharpened piercing tip). For example, a portion of the outer circumferential edge (2106) may be smoothed at the proximal end (2108) of the distal tip (2100), or the entire outer circumferential edge (2106), up to the angled surfaces (2116) may be smoothed. Additionally, it may be desirable to smooth or deburr the surface between the edges (2118) and/or the internal or external surface of the cannula adjacent to the opening (2112) at the proximal end (2108) or distal end (2110) of the distal tip (2100), or circumferentially around the opening (2112).

Portions of the distal tip (2100) of the cannula may be deburred, smoothed, evened, rounded, dulled, or the like, using any suitable mechanism. For example, smoothing portions of the distal tip of the cannula may comprise mechanical and/or manual deburring, abrasive or soda media blasting, sanding, grinding, wire brushing, laser ablating, polishing (e.g., electropolishing), a combination thereof, or the like.

Turning back to FIG. 19, the method of manufacturing a cannula (1900) may further comprise bending a distal portion of the cannula (1914) to form the distal curved portion described above. Bending the catheter may properly orient the distal tip such that it may atraumatically puncture the trabecular meshwork. Referring back to FIG. 3, in some variations, the distal portion of the cannula may be bent such that the sharpened piercing tip is located along the outer radius (322) of the curved cannula. In some instances, the distal portion of the cannula may be bent to an angle between about 100 and about 125 degrees, about 115 and about 125 degrees, or to about 118 degrees relative to an external surface of a proximal portion of the cannula.

The distal portion of the cannula may be bent using any suitable mechanical or manual bending process. It may be important to select a bending process that does not alter the cross-sectional size and shape of the cannula during the bending process. Additionally, it should be appreciated that the cannula may be bent at any point in the manufacturing process, and bending need not occur after the distal tip of the cannula is smoothed, as depicted in the method (1900) in FIG. 19.

The method of manufacturing a cannula (1900) may optionally comprise polishing (1916) all or a portion of the cannula, for example, the distal tip of the cannula. In variations in which the cannula is polished, polishing the cannula (1916) may remove debris, markings, indentations, grooves, or the like, left on the surfaces of the cannula. These markings may be remnants from any part of the manufacturing process, and specifically may be from creating the bevel at the distal tip of the cannula (1906), sharpening the distal tip of the cannula (1908), and/or smoothing a portion of the distal tip of the cannula (1912). Polishing the cannula (1916) may be especially useful in variations in which smoothing a portion of the distal tip of the cannula (1912) comprises a process that generally leaves debris or markings behind, for example, laser ablation. Polishing the cannula (1916) may be completed using any suitable method, for example, electropolishing, staged media blasting using media with increasing grain size, or the like.

If desired, the cannula may be cleaned (1918) prior to its installation into the delivery systems described here. For example, in some variations, the cannula may be passivated to remove iron oxide or other contaminants. In some instances, the cannula may be passivated using an acid like, for example, nitric oxide. In other variations, the cannula may be cleaned using cleansers, ultrasonic baths, or any other suitable cleaning process.

The cannula and/or the assembled delivery system may be sterilized, for example, using gamma irradiation. The gamma irradiation dose range may be, for example, between 25-40 kGy. Other irradiation energies may be used for sterilization, for example e-beam irradiation. Alternative sterilization methods include gas sterilization, for example ethylene oxide gas sterilization. In variations in which all or a portion of the systems are reusable, as described herein, these portions may be sterilized and reused. For example, in variations in which the handle is reusable and the cannula and elongate member are disposable, after use the used cannula and elongate member may be removed, the handle sterilized, and a new cannula and elongate member attached to the sterile handle.

While the inventive devices, systems, kits, and methods have been described in some detail by way of illustration, such illustration is for purposes of clarity of understanding only. It will be readily apparent to those of ordinary skill in the art in light of the teachings herein that certain changes and modifications may be made thereto without departing from the spirit and scope of the appended claims.

The invention claimed is:

1. A method for treating conditions of the eye using a device comprising a fluid assembly coupled to a linear gear via a linkage, a housing, a plunger, and an elongate member comprising a lumen, wherein the fluid assembly comprises a reservoir, and wherein the plunger comprises a lumen that fluidly connects the reservoir to the lumen of the elongate member, a proximal end that is located slidably within the reservoir, and a distal end that is fixedly attached to the linear gear, comprising:
  advancing the elongate member into Schlemm's canal by moving the linear gear and the fluid assembly together relative to the housing, wherein the linkage maintains a fixed distance between the fluid assembly and linear gear during advancement of the elongate member; and
  retracting the elongate member and simultaneously delivering a fluid composition out of a distal opening of the lumen by moving the linear gear relative to the linkage, the fluid assembly, and the housing to decrease a distance between the fluid assembly and the linear gear, such that the plunger moves proximally within the reservoir to increase the length of the plunger within the reservoir and displace fluid composition within the reservoir.

2. The method of claim 1, wherein retracting the elongate member and delivering the fluid composition are both actuated by rotation of a wheel.

3. The method of claim 1, wherein the elongate member is advanced a first length around Schlemm's canal, and wherein the fluid composition is delivered the same first length around Schlemm's canal.

4. The method of claim 1, wherein the elongate member is advanced about 180 degrees around Schlemm's canal in a first direction.

5. The method of claim 4, further comprising:
advancing the elongate member about 180 degrees around Schlemm's canal in a second direction; and
retracting the elongate member and simultaneously delivering a fluid composition out of the distal opening of the lumen.

6. The method of claim 1, wherein the linear gear is coupled to a wheel, and wherein rotation of the wheel in a first direction moves the linear gear and the fluid assembly relative to the housing.

7. The method of claim 6, wherein rotation of the wheel in a second, opposite direction moves the linear gear relative to the linkage and the fluid assembly.

8. The method of claim 1, wherein the device further comprises a lock configured to restrict movement of the fluid assembly relative to the housing prior to use.

9. The method of claim 8, further comprising disengaging the lock to allow movement of the fluid assembly relative to the housing.

10. The method of claim 1, wherein the fluid assembly moves distally, but not proximally, relative to the housing.

11. The method of claim 1, wherein the fluid assembly moves distally relative to the housing during advancement of the elongate member and is fixed relative to the housing during retraction of the elongate member.

12. The method claim 11, wherein the housing comprises teeth that allow the fluid assembly to move distally relative to the housing during advancement of the elongate member and fix the fluid reservoir relative to the housing during retraction of the elongate member.

13. The method of claim 1, further comprising:
advancing the elongate member into Schlemm's canal by moving the linear gear and the fluid assembly together relative to the housing a second time; and
retracting the elongate member and simultaneously delivering additional fluid composition out of the distal opening of the lumen by moving the linear gear relative to the linkage, the fluid assembly, and the housing a second time.

14. The method of claim 13, wherein advancing the elongate member into Schlemm's canal moves the fluid assembly distally to a first position, and wherein re-advancing the elongate member into Schlemm's canal moves the fluid assembly from the first position distally to a second position.

15. The method of claim 14, wherein advancing the elongate member into Schlemm's canal moves the fluid assembly distally from an initial position to the first position, and the second position is a distal-most position of the fluid assembly, wherein the distance between the initial position and the second position determines a fixed cumulative amount of extension and retraction of the elongate member.

16. The method of claim 14, wherein the distance between the initial position and the second position determines a fixed cumulative volume of fluid composition for delivery.

17. The method of claim 14, wherein the fluid assembly remains in the first position during reaction of the elongate member.

18. The method of claim 14, wherein the fluid assembly has a maximum travel distance, and wherein moving the fluid assembly distally to the first position moves the fluid assembly half of its maximum travel distance.

19. The method of claim 4, wherein between about 2 microliters and about 9 microliters of the fluid composition are delivered to Schlemm's canal.

20. The method of claim 19, wherein about 4.5 microliters of the fluid composition are delivered to Schlemm's canal.

21. The method of claim 1, wherein the elongate member is advanced about 360 degrees around Schlemm's canal.

22. The method of claim 4, wherein about 10 microliters of the fluid composition are delivered to Schlemm's canal.

23. The method of claim 5, wherein about 20 microliters of the fluid composition are delivered to Schlemm's canal in total.

24. The method of claim 1, further comprising tearing or cutting the trabecular meshwork.

25. The method of claim 24, wherein the trabecular meshwork is torn by the elongate member.

26. The method of claim 25, wherein the trabecular meshwork is torn by the body of the elongate member.

* * * * *